US012779035B2

(12) United States Patent
Schrepfer et al.

(10) Patent No.: US 12,779,035 B2
(45) Date of Patent: Nov. 3, 2026

(54) TRANSPLANTED CELL PROTECTION VIA INHIBITION OF POLYMORPHONUCLEAR CELLS

(71) Applicant: The Regents of the University of California, Oakland, CA (US)

(72) Inventors: Sonia Schrepfer, Burlingame, CA (US); Tobias Deuse, Burlingame, CA (US)

(73) Assignee: The Regents of the University of California, Oakland, CA (US)

( * ) Notice: Subject to any disclaimer, the term of this patent is extended or adjusted under 35 U.S.C. 154(b) by 996 days.

(21) Appl. No.: 17/792,133

(22) PCT Filed: Jan. 14, 2021

(86) PCT No.: PCT/US2021/013499

§ 371 (c)(1),
(2) Date: Jul. 11, 2022

(87) PCT Pub. No.: WO2021/146471

PCT Pub. Date: Jul. 22, 2021

(65) Prior Publication Data

US 2023/0058557 A1 Feb. 23, 2023

Related U.S. Application Data

(60) Provisional application No. 63/003,264, filed on Mar. 31, 2020, provisional application No. 62/961,636, filed on Jan. 15, 2020.

(51) Int. Cl.

| | |
|---|---|
| ***A61K 39/39*** | (2006.01) |
| ***A61K 31/165*** | (2006.01) |
| ***A61K 31/513*** | (2006.01) |
| ***A61K 31/52*** | (2006.01) |
| ***A61K 31/5377*** | (2006.01) |
| ***A61K 31/573*** | (2006.01) |
| ***A61K 35/545*** | (2015.01) |
| ***A61K 38/13*** | (2006.01) |
| ***A61K 38/17*** | (2006.01) |
| ***A61K 39/395*** | (2006.01) |
| ***A61P 11/00*** | (2006.01) |

(52) U.S. Cl.

CPC ........ *A61K 39/3955* (2013.01); *A61K 31/165* (2013.01); *A61K 31/513* (2013.01); *A61K 31/52* (2013.01); *A61K 31/5377* (2013.01); *A61K 31/573* (2013.01); *A61K 35/545* (2013.01); *A61K 38/13* (2013.01); *A61K 38/177* (2013.01); *A61K 38/1774* (2013.01); *A61P 11/00* (2018.01)

(58) Field of Classification Search

None

See application file for complete search history.

(56) References Cited

U.S. PATENT DOCUMENTS

| | | | |
|---|---|---|---|
| 4,427,777 | A | 1/1984 | Goldstein |
| 4,609,627 | A | 9/1986 | Goldstein |
| 5,606,042 | A | 2/1997 | Smith et al. |
| 5,633,130 | A | 5/1997 | Smith et al. |
| 5,731,426 | A | 3/1998 | Smith et al. |
| 5,786,464 | A | 7/1998 | Seed |
| 5,849,287 | A | 12/1998 | Greenberger et al. |
| 6,099,857 | A | 8/2000 | Gross |
| 6,114,148 | A | 9/2000 | Seed |
| 6,184,017 | B1 | 2/2001 | Smith et al. |
| 6,682,728 | B1 | 1/2004 | Finkel et al. |
| 7,355,012 | B2 | 4/2008 | Pastan |
| 7,413,904 | B2 | 8/2008 | Gold et al. |
| 7,541,034 | B1 | 6/2009 | Fitzgerald |
| 7,982,011 | B2 | 7/2011 | Pastan |
| 8,236,771 | B2 | 8/2012 | Cicciarelli et al. |
| 8,697,359 | B1 | 4/2014 | Zhang |
| 8,771,945 | B1 | 7/2014 | Zhang |
| 8,795,965 | B2 | 8/2014 | Zhang |
| 8,796,443 | B2 | 8/2014 | Khvorova et al. |
| 8,865,406 | B2 | 10/2014 | Zhang |

(Continued)

FOREIGN PATENT DOCUMENTS

| | | |
|---|---|---|
| CA | 3003150 | 5/2017 |
| CN | 102459575 A | 5/2012 |

(Continued)

OTHER PUBLICATIONS

Gorczynski et al., Clin Exp Immunol 2001, 126:220-229 (Year: 2001).*

Shankar et al., Genome engineering of induced pluripotent stem cells to manufacture natural killer cell therapies, Stem Cell Res. Ther., 11(1):234 (2020).

Silva et al., From Mononumeric to Homodimeric Endonucleases and Back: Engineering Novel Specificity of LAGLIDADG Enzymes, J. Mol. Biol., 361:744-754 (2006).

Silva et al., Meganucleases and Other Tools for Targeted Genome Engineering: Perspectives and Challenges for Gene Therapy, Current Gene Therapy, 11:11-27 (2011).

Simsek et al., "Rapid Rh D Genotyping by Polymerase Chain Reaction-Based Amplification of DNA," Blood, 85 (10):2975-2980 (1995).

(Continued)

*Primary Examiner* — Stacy B Chen

(74) *Attorney, Agent, or Firm* — Kaplan IP Law, P.C.; Jonathan M. Kaplan

(57) ABSTRACT

The invention provides, for the first time, strategies to inhibit the killing of transplanted cells by activated polymorphonuclear cells (PMNs) of the recipient. Multiple different modes for PMN inhibition are provided and one or more agents effectively utilized every mode of action. The combination of two or more of those agents with different modes of action synergistically improved the efficacy of PMN inhibition without exerting toxic side effects on the survival of the target cells. The cells may be pluripotent cells, including hypoimmune pluripotent cells (HIP), ABO blood type O Rhesus Factor negative HIP cells (HIPO−), or derivatives thereof. The cells may also be alpha 1 antitrypsin (A1AT) secreting cells.

15 Claims, 32 Drawing Sheets

Figure 1:
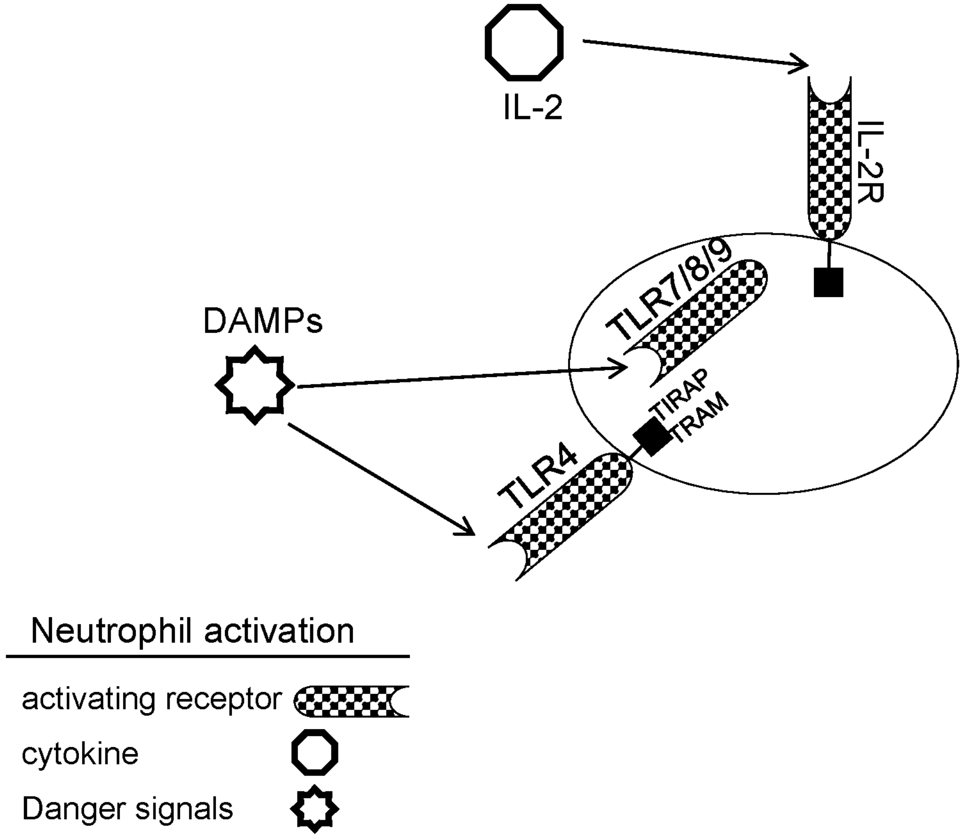

Specification includes a Sequence Listing.

(56) References Cited

U.S. PATENT DOCUMENTS

| | | | |
|---|---|---|---|
| 8,871,445 B2 | 10/2014 | Cong | |
| 8,889,356 B2 | 11/2014 | Zhang | |
| 8,895,308 B1 | 11/2014 | Zhang | |
| 8,906,616 B2 | 12/2014 | Zhang | |
| 8,927,280 B2 | 1/2015 | Melton | |
| 8,932,814 B2 | 1/2015 | Cong | |
| 8,945,839 B2 | 2/2015 | Zhang | |
| 8,993,233 B2 | 3/2015 | Zhang | |
| 8,999,641 B2 | 4/2015 | Zhang | |
| 9,157,062 B2 | 10/2015 | Chen | |
| 9,683,215 B2 | 6/2017 | Melton | |
| 10,011,847 B2 | 7/2018 | Aranda et al. | |
| 10,047,340 B2 | 8/2018 | West | |
| 10,287,606 B2 | 5/2019 | Valamehr et al. | |
| 10,294,492 B2 | 5/2019 | Martinez et al. | |
| 10,730,944 B2 | 8/2020 | Giurleo | |
| 11,026,975 B2 | 6/2021 | Zhou | |
| 11,162,079 B2 | 11/2021 | Schrepfer et al. | |
| 12,221,622 B2 | 2/2025 | Schrepfer et al. | |
| 2003/0077249 A1 | 4/2003 | Bebbington | |
| 2004/0053836 A1 | 3/2004 | Mayer-Kuckuk et al. | |
| 2004/0053936 A1 | 3/2004 | Akiyama et al. | |
| 2005/0048069 A1 | 3/2005 | Gorczynski et al. | |
| 2006/0084142 A1 | 4/2006 | Heinrich et al. | |
| 2006/0246074 A1 | 11/2006 | Halle et al. | |
| 2007/0224176 A1 | 9/2007 | Brink | |
| 2007/0274967 A1 | 11/2007 | Cao | |
| 2008/0095784 A1 | 4/2008 | Graziano et al. | |
| 2010/0135992 A1* | 6/2010 | Rother .................... | A61P 13/12 424/130.1 |
| 2010/0272812 A1 | 10/2010 | Arroyo et al. | |
| 2011/0286980 A1 | 11/2011 | Brenner | |
| 2012/0282174 A1 | 11/2012 | Weissman et al. | |
| 2013/0046015 A1 | 2/2013 | Axtell et al. | |
| 2014/0142161 A1 | 5/2014 | Flotte et al. | |
| 2014/0341899 A1 | 11/2014 | Dinarello et al. | |
| 2016/0139124 A1 | 5/2016 | Newman et al. | |
| 2016/0151465 A1 | 6/2016 | Slawin et al. | |
| 2016/0176969 A1 | 6/2016 | Bernett | |
| 2016/0230143 A1 | 8/2016 | Chen et al. | |
| 2016/0256495 A1 | 9/2016 | Cho et al. | |
| 2016/0348073 A1 | 12/2016 | Meissner | |
| 2017/0073674 A1 | 3/2017 | Maeder | |
| 2017/0313759 A1 | 11/2017 | Batuwangala | |
| 2017/0314015 A1 | 11/2017 | Friedland | |
| 2018/0000969 A1 | 1/2018 | Gunther et al. | |
| 2018/0112179 A1 | 4/2018 | Wu | |
| 2018/0155717 A1 | 6/2018 | Valamehr et al. | |
| 2019/0201548 A1 | 7/2019 | Kahvejian et al. | |
| 2019/0264177 A1 | 8/2019 | Kahvejian et al. | |
| 2019/0270818 A1 | 9/2019 | Yachi et al. | |
| 2019/0282618 A1 | 9/2019 | Rosen et al. | |
| 2019/0376045 A1 | 12/2019 | Schrepfer et al. | |
| 2020/0109364 A1 | 4/2020 | Dipersio | |
| 2020/0172620 A1 | 6/2020 | Chen | |
| 2020/0246381 A1 | 8/2020 | Zhou | |
| 2020/0299349 A1 | 9/2020 | Garcia et al. | |
| 2020/0339699 A1 | 10/2020 | Li | |
| 2020/0354673 A1 | 11/2020 | Schrepfer | |
| 2020/0354684 A1 | 11/2020 | Schrepfer et al. | |
| 2021/0029271 A1 | 1/2021 | Kiser et al. | |
| 2021/0030818 A1 | 2/2021 | Ghannoum | |
| 2021/0292715 A1 | 9/2021 | Schrepfer et al. | |
| 2021/0308183 A1 | 10/2021 | Schrepfer et al. | |
| 2022/0049004 A1 | 2/2022 | Zhang et al. | |
| 2022/0049227 A1 | 2/2022 | Schrepfer et al. | |
| 2022/0213434 A1 | 7/2022 | Schrepfer et al. | |
| 2022/0347215 A1 | 11/2022 | Deuse | |
| 2023/0058557 A1 | 2/2023 | Schrepfer et al. | |
| 2023/0348862 A1 | 11/2023 | Schrepfer et al. | |
| 2024/0043803 A1 | 2/2024 | Deuse | |
| 2024/0091274 A1 | 3/2024 | Deuse | |
| 2024/0139341 A1 | 5/2024 | Deuse | |
| 2024/0325536 A1 | 10/2024 | Deuse | |
| 2025/0032544 A1 | 1/2025 | Deuse | |
| 2025/0268949 A1 | 8/2025 | Deuse | |
| 2025/0283051 A1 | 9/2025 | Schrepfer et al. | |

FOREIGN PATENT DOCUMENTS

| | | | | |
|---|---|---|---|---|
| CN | 108048484 | A | 5/2018 |
| CN | 110093351 | A | 8/2019 |
| EP | 2080809 | B1 | 2/2012 |
| GB | 2211504 | A | 7/1989 |
| WO | 1997/015664 | | 5/1997 |
| WO | WO9715664 | A1 | 5/1997 |
| WO | 1999023210 | | 5/1999 |
| WO | WO9923210 | A1 | 5/1999 |
| WO | 2001011011 | A2 | 2/2001 |
| WO | WO02102997 | A2 | 12/2002 |
| WO | 2003050247 | A2 | 6/2003 |
| WO | 2003100018 | A2 | 12/2003 |
| WO | 2004042346 | A2 | 5/2004 |
| WO | 2006002438 | A2 | 1/2006 |
| WO | 2007133811 | A2 | 11/2007 |
| WO | 2009124404 | A1 | 10/2009 |
| WO | 2010/104949 | | 9/2010 |
| WO | WO201014180 | A2 | 12/2010 |
| WO | 2011100567 | A1 | 8/2011 |
| WO | WO2011146862 | A1 | 11/2011 |
| WO | 2012/079000 | | 6/2012 |
| WO | 2012112576 | A1 | 8/2012 |
| WO | 2012/138927 | | 10/2012 |
| WO | 2012/163805 | | 12/2012 |
| WO | 2013/040557 | | 3/2013 |
| WO | WO2013158292 | A1 | 10/2013 |
| WO | 2014/025828 | | 2/2014 |
| WO | 2014/154553 | | 10/2014 |
| WO | 2014165663 | A1 | 10/2014 |
| WO | 2015134877 | A1 | 9/2015 |
| WO | 2015164740 | A1 | 10/2015 |
| WO | WO201516740 | A1 | 10/2015 |
| WO | 2015/184203 | | 12/2015 |
| WO | 2016/030414 | | 3/2016 |
| WO | 2016034679 | A1 | 3/2016 |
| WO | WO2016073955 | A2 | 5/2016 |
| WO | 2016/126608 | | 8/2016 |
| WO | 2016144984 | A1 | 9/2016 |
| WO | 2016146262 | A1 | 9/2016 |
| WO | WO2016142532 | A1 | 9/2016 |
| WO | 2016/183041 | | 11/2016 |
| WO | WO2016183041 | A2 | 11/2016 |
| WO | WO2017039445 | A1 | 3/2017 |
| WO | 2017/058753 | | 4/2017 |
| WO | WO2017064084 | A1 | 4/2017 |
| WO | 2017075276 | A2 | 5/2017 |
| WO | WO2017079673 | A1 | 5/2017 |
| WO | 2017127755 | A1 | 7/2017 |
| WO | 2017/058850 | | 8/2017 |
| WO | 2017/134306 | | 8/2017 |
| WO | 2017/165862 | | 9/2017 |
| WO | 2017179021 | A1 | 10/2017 |
| WO | 2017/194699 | | 11/2017 |
| WO | 2018/028647 | | 2/2018 |
| WO | 2018/132783 | | 7/2018 |
| WO | WO2018132783 | A1 | 7/2018 |
| WO | 2018148183 | A1 | 8/2018 |
| WO | 2018/170096 | | 9/2018 |
| WO | 2018/175390 | | 9/2018 |
| WO | 2018170046 | A1 | 9/2018 |
| WO | 2018183705 | A1 | 10/2018 |
| WO | 2018/213337 | | 11/2018 |
| WO | WO2018227286 | A2 | 12/2018 |
| WO | 2019/006072 | | 1/2019 |
| WO | 2019/032661 | | 2/2019 |
| WO | 2019045775 | A1 | 3/2019 |
| WO | 2019/084531 | | 5/2019 |
| WO | 2019084388 | A1 | 5/2019 |
| WO | 2019097083 | A1 | 5/2019 |
| WO | 2020018615 | A2 | 1/2020 |
| WO | WO2020018615 | A1 | 1/2020 |
| WO | WO2020018620 | A1 | 1/2020 |
| WO | 2020/060924 | | 3/2020 |

(56) References Cited

FOREIGN PATENT DOCUMENTS

| | | | |
|---|---|---|---|
| WO | 2020168317 | A2 | 8/2020 |
| WO | 2020/231882 | | 11/2020 |
| WO | 2020223535 | A1 | 11/2020 |
| WO | 2020231882 | A2 | 11/2020 |
| WO | 2020/257412 | | 12/2020 |
| WO | 2021/022223 | | 2/2021 |
| WO | 2021/041316 | | 3/2021 |
| WO | 2021/072328 | | 4/2021 |
| WO | 2021/146222 | | 7/2021 |
| WO | 2021146222 | A1 | 7/2021 |
| WO | 2021146471 | A2 | 8/2021 |
| WO | 2021/222285 | | 11/2021 |
| WO | 2021076427 | A1 | 4/2022 |

OTHER PUBLICATIONS

Smith et al., "A combinatorial approach to create artificial homing endonucleases cleaving chosen sequences," Nucleic Acids Res. 34(22) e149: 1-12 (2006).
Smith T. et al., In situ programming of leukaemia-specific T cells using synthetic DNA nanocarriers, Nature Nanotechnology, 12(8):813-820 (2017).
Stoddard, "Homing endonuclease structure and function," Quarterly Reviews of Biophysics, Cambridge University Press, 1-47 (2005).
Strecker, J. et al., Engineering of CRISPR-Cas12b for human genome editing, Nat. Commun., 10(1):212 (2019).
Strecker, J. et al., RNA-guided DNA insertion with CRISPR-associated transposases, Science, 365(6448):48-53 (2019).
Sussman et al., Isolation and Characterization of New Homing Endonuclease Specificities at Individual Target Site Positions, J. Mol. Biol., 342:31-41 (2004).
Szczepek et al., Structure-based redesign of the dimerization interface reduces the toxicity of zinc-finQer nucleases, Nature Biotech., 25(7): 1-28 (2007).
Tachibana, "Beyond CRISPR: What's current and upcoming in genome editing," Science, 1481-1483, www.sciencemag.org/featums/20"I 9/09ibeyond-crispr-what-s-current-andur2coming-genome-editing, (2019).
Themeli et al., Generation of tumor-targeted human T lymphocytes from induced pluripotent stem cells for cancer therapy, Nature Biotechnology, 31(10): 928-933 (2013).
Themeli et al., New Cell Sources for T Cell Engineering and Adoptive Immunotherapy, Cell Stem Cell, 16(4): 357-366 (2015).
Top, D. et al., Liposome reconstitution of a minimal protein-mediated membrane fusion machine, Embo J., 24 (17):2980-2988 (2005).
UniProtKB/Swiss-Prot: 029980.2, RecName: Full=MHC class I polypeptide-related sequence B; Short=MIC-B; Flags: Precursor, 11 pages, (2024).
UniProtKB/Swiss-Prot: 029983.1, RecName: Full=MHC class I polypeptide-related sequence A; Short=MIC-A; Flags: Precursor, 17 pages, (2024).
Van Roey et al., Catalytic domain structure and hypothesis for function of GIY-YIG intron endonuclease I-Tevl, Nature Struct. Biol., 9(11):806-811 (2002).
Vignali, D.A.A. et al., How regulatory T cells work, Nat. Rev. Immunol., 8(7):523-532 (2008).
Wang, B. et al., Generation of hypoimmunogenic T cells from genetically engineered allogeneic human induced pluripotent stem cells, Nat. Biomed. Eng., 5(5):429-440 (2021).
Wilbie, D. et al., Delivery Aspects of CRISPR/Cas for in Vivo Genome Editing, Acc. Chem. Res., 52(6): 1555-1564 (2019).
Wood et al., Targeted Genome Editing Across Species Using ZFNs and TALENs, Science, 333(6040):307 (2011).
Wu et al., Multimerization of chimeric anti-CD20 single-chain Fv-Fc fusion protein is mediated through variable domain exchange, Protein Engineering, 14(12):1025-1033 (2001).
Xu, C. et al., Cardiac bodies: a novel culture method for enrichment of cardiomyocytes derived from human embryonic stem cells, Stem Cells Dev., 15(5):631-639 (2006).
Yamamoto et al., "Molecular genetic basis of the histo-blood group ABO system," Nature, 345:229-233 (1990).
Yan, W.X. et al., Functionally diverse type V CRISPR-Cas systems, Science, 363(6422):88-91 (2019).
Yazawa et al., Immunotherapy using unconjugated CD19 monoclonal antibodies in animal models for B lymphocyte malignancies and autoimmune disease, Proc. Natl. Acad. Sci. USA, 102(42): 15178-15183 (2005).
Yuan, M. et al., A highly conserved cryptic epitope in the receptor binding domains of SARSCOV-2 and SARS-COV, Science, 368(6491 ):630-633 (2020).
Zeng et al., Generation of 'Off-the-Shelf' Natural Killer Cells from Peripheral Blood Cell-Derived Induced Pluripotent Stem Cells, Stem Cell Reports, 9:1796-1812 (2017).
Zetsche, B. et al., Cpf1 is a single RNA-guided endonuclease of a class 2 CRISPR-Cas system, Cell, 163 (3):759-771 (2015).
Zhang C. et al., Engineering CAR-T cells, Biomarker Research, 5:22 (2017).
Zhang, Efficient construction of sequence-specific TAL effectors for modulating mammalian transcription, Nature Biotech., 29(2):149-153 (2011).
Zhang, Q. et al., The microprotein Minion controls cell fusion and muscle formation, Nat. Commun., 8:15664 (2017).
Zhao et al., A phase 1, open-label study of LCAR-B38M, a chimeric antigen receptor T cell therapy directed against B cell maturation antigen, in patients with relapsed or refractory multiple myeloma, J. Hematol. Oncol., 11 (1): 141 (2018).
Zhu et al., An improved method to produce clinical scale natural killer cells from human pluripotent stem cells, Methods Mol Biol., 2048:107-119 (2019).
Bouguermouh et al. "CD47 Expression on T Cell Is a Self-Control Negative Regulator of Type 1 Immune Response," The Journal of Immunology, Jun. 15; 180(12): 8073-82, 2008.
Maeda et al. "Regeneration of CD8ab T Cells from T-cell-Derived iPSC Imprats Potent Tumor Antigen-Specific Cytotoxicity," Cancer Research, vol. 76, No. 23, pp. 6839-6850, 2016.
Nishimura et al., Generation of Rejuvenated Antigen-Specific T Cells by Reprogramming to Pluripotency and Redifferentiation, Cell Stem Cell, 12, 114-126, Jan. 3, 2013.
Vermeer et al. "Radiation-induced loss of cell surface CD47 enhances immune-mediated clearance of human papillomavirus-positive cancer," Int J Cancer. Jul; 133(1): 120-9, 2013.
Jha et al. Efficient Differentiation of Cardiomyocytes from Human Pluripotent Stem Cells with Growth Factors, Methods Mol Biol. 2015 ; 1299: 115-131.
Sharma et al. Derivation of Highly Purified Cardiomyocytes from Human Induced Pluripotent Stem Cells Using Small Molecule-modulated Differentiation and Subsequent, Glucose Starvation, J. Vis Exp. 2015.
Shiba et al. hESC-Derived Cardiomyocytes Electrically Couple and Suppress Arrhythmias in Injured Hearts, Nature 489(7415): 322-5, 2012.
Si-Tayeb et al. Highly Efficient Generation of Human Hepatocyte-Like Cells from Induced Pluripotent Stem Cells, Hepatology 51:297-305, 2010.
Smith & Waterman. Comparison of Biosequences, Adv. Appl. Math. 2:482, 1981.
Takahashi et al. Induction of Pluripotent Stem Cells from Mouse Embryonic and Adult Fibroblast Cultures by Defined Factors, Cell 126:663-676, 2006.
Vegas et al. Long term Glycemic Control Using Polymer Encapsulated, Human Stem-Cell Derived B-cells in Immune Competent mice, Nat Med. 22(3): 306-311, 2016.
Woltjen et al. piggyBac transposition reprograms fibroblasts to induced pluripotent stem cells, Nature 458 (7239): 766-770, 2009.
Zhou et al. Adenoviral Gene Delivery Can Reprogram Human Fibroblasts to Induced Pluripotent Stem Cells, Stem Cells 27 (11): 2667-74, 2009.
Zhou et al. Generation of Induced Pluripotent Stem Cells Using Recombinant Proteins, Cell Stem Cell 8:381-384, 2009.

(56) References Cited

OTHER PUBLICATIONS

Ellis et al. Regenerative medicine and cell-based approaches to restore pancreatic function, Nature Reviews, vol. 14, 612-628, 2017.
Fiers et al., Complete nucleotide sequence of SV40 Dna, Nature 273: 113-120, 1978.
Greenaway P. J. et al. Human cytomegalovirus DNA: BamHI, EcoRI and Pst I restriction endonuclease cleavage maps, Gene 18: 355-360, 1982.
Huang et al. Differentiation of human embryonic stem cells into smooth muscle cells in adherent monolayer culture, Biochem Biophys Res Commun 351(2)321-7, 2006.
Nakagawa et al. Generation of induced pluripotent stem cells without Myc from mouse and human fibroblasts, Nature Biotechnology 26:101-106, 2007.
Shiba et al. Allogeneic transplantation of iPS cell-derived cardiomyocytes regenerates primate hearts, Nature 538 (7625):388-391, 2016.
Snykers et al., Hepatic Differentiation of Mesenchymal Stem Cells: In Vitro Strategies, Methods Mol Biol 698:305-314, 2011.
Hawksworth et al., "Enhancement of red blood cell transfusion compatibility using CRISPR-mediated erythroblast gene editing," EMBO Mol Med, vol. 10, No. 6, Apr. 26, 2018.
PCT Search Report and Written Opinion for PCT/US2020/032272, dated Oct. 30, 2020.
PCT Search Report and Written Opinion for PCT/US2020/039220, dated Oct. 30, 2020.
Murata, Y et al. "Anti-human SIRPa antibody is a new tool for cancer immunotherapy," Cancer Science, vol. 109, pp. 1300-1308, 2018.
Nath, PR, CD47 Expression in natural killer cells regulates homeostasis and modulates immune response to lymphocytic choriomeningitis virus, Front Immunol vol. 9, 2018.
Pan, YF, Signal Regulatory Protein a is associated with tumor-polarized macrophages phenotype switch and plays a pivotal role in tumor progression. Hepatology, vol. 58 No. 2, 2013.
Focosi et al. Effect of Induced Pluipotent Stem Cell Technology in Blood Banking, Stem Cells Translational Medicine, 5:269-274, 2016.
Seltsam et al. Systematic analysis of the ABO gene diversity within exons 6 and 7 by PCR screening reveals new ABO alleles, Transfusion, 43:428-439, 2003.
Han et al. Generation of hypoimmunogenic human pluripotent stem cells, published online Apr. 30, 2019, PNAS, 116:10441-10446, May 2019.
Westhoff, Haabb, 52nd Annual Meeting, Apr. 9-10, 2019, Creating customized red cell reagents from iPSC cells accessed at http://www.haabb.org/images/06_HAA_cultured_RBCS_as_reagents_Connie__Westhoff.pdf accessed on Oct. 28, 2020.
Li et al. How far are stem-cell-derived erythrocyts from the clinical arena?, BioScience, Aug. 2013, vol. 63 No 8, pp. 632-643.
Lowry et al. Generation of human induced pluripotent stem cells from dermal fibroblasts, PNAS, 105:2883-2888, 2008.
Mallon et al. Comparison of the molecular profiles of human embryonic and induces pluripotentstem cells of isogenic origin, Stem Cell Research, 12:376-386, 2014.
Reijo et al. Gene expression profiles of human inner cell mass cells and embryonic stem cells, Differentiation, vol. 78, pp. 18-23, 2009.
Reubinoff et al. Embryonic stem cell lines from human bastocysts: somatic differentiation in vitro, Nature Biotechnology, vol. 18, pp. 399-404, Apr. 2000.
Thomson et al., Embryonic Stem Cell Lines Derived from Human Blastocysts, Science 282, 1145, 1998.
Breimer et al. Glycosphingolipids of human embryonic stem cells, Glycoconj J (2017) 34:713-723, Published online 2016.
Lee et al. Evaluation of 28 Human Embryonic Stem Cell Lines for Use as Unrelated Donors in Stem Cell Therapy: Implications of HLA and ABO Genotypes, Cell Transplantation, vol. 19, pp. 1383-1395, 2010.
Romagnuolo et al. Human Embryonic Stem Cell-Derived Cardiomyocytes Regenerate the Infarcted Pig Heart but Induce Ventricular Tachyarrhythmias, Stem Cell Reports (2019), https://doi.org/10.1016/j.stemcr.2019.04.005.
Taylor et al. Immunological considerations for embryonic and induced pluripotent stem cell banking, Phil. Trans. R. Soc. B (2011) 366, 2312-2322.
Mllartay et al. HLA antigens on peripheral red blood cells: analysis by flow cytofluorometry using monoclonal antibodies, Tissue Antigens (1985) 26, 12-19.
PCT Search Report and Written Opinion dated Mar. 17, 2021 issued in PCT Application No. PCT/US2020/055120.
PCT Search Report and Written Opinion dated Jul. 22, 2021 issued in PCT Application No. PCT/US2021/013499.
PCT Search Report and Written Opinion dated Aug. 10, 2022, issued in PCT/US2022/022368.
Absolute Antibody, "Antibody Effector Functions", Absolute Antibody, Web. Retrieved Online [Jun. 22, 2022]. <URL:https://absoluteantibody.com/antibody-resources/antibody-overview/antibody-effector-functions/>. Mar. 1, 2021.
Catro-Dopico. "FC Receptors in Solid Organ Transplantation" 284-293. Current Transplant Reports. Web. Retrieved Online [22.06.2022]. <URL:https://www.ncbi.nim.nih.gov/pmc/articles/PMC5107199/pdf/40472_2016_Article_116.pdf>. Oct. 3, 2016.
Kim et al. Rh D blood group conversion using transcription activator-like effector nucleases. Nature Communications 6: 7451, pp. 1-13, (2015).
Jaiswal et al. CD47 is up-regulated on circulating hematopoietic stem cells and leukemia cells to avoid phagocytosis. Cell 23: 138:271-285, (2009).
Yamamoto et al. Genomic Organization of human histo-blood group ABO genes. Glycobiology vol. 5, pp. 51-58, (1995).
Liu. CRISPR-Cas9-mediated multiplex gene editing in CAR-T cells. Cell Research 27, 154-157, (2017).
Zheng et al. Concise Review: One Stone for Multiple Birds: Generating Universally Compatible Human Embryonic Stem Cells. Stem Cells.34:2269-2275, 2016.
Lee et al. Generation of Human Pluripotent Stem Cell-derived Endothelial Cells and Their Therapeutic Utility. Current Cardiology Reports, 20:45, 2018.
Chen et al. Harnessing cell pluripotency for cardiovascular regenerative medicine. Nature Biomedical Engineering, Vo. 2, pp. 392-398, 2018.
Hosoya et al. Preparation of pancreatic B-cells from human iPS cells with small molecules. Islets, 4:3, pp. 249-252, 2012.
Paluch et al. "Immune Checkpoints as Therapeutic Targets in Autoimmunity," Frontiers in Immunology, vol. 9, Article 2306, pp. 1-11,Oct. 8, 2018.
PCT Search Report and Written Opinion for PCT/US2023/018189 dated Sep. 11, 2023.
Zhu et al. "Engineered human pluripotent stem cell-derived natural killer cells: the next frontier for cancer immunotherapy," Blood Science, vol. 1, No. 1, pp. 4-11, Aug. 1, 2019.
Bagnis et al. "A genetic strategy to control expression of human blood group antigens in red blood cells generated in vitro," Transfusion, vol. 49, pp. 967-976, 2009.
Regateiro et al. TGF-B in transplantation tolerance, Current Opinion in Immunology, 23: 660-669, 2011.
Sehn, "Insertions and Deletions (Indels)," Clinical Genomics, Chapter 9, pp. 129-150, 2015.
Teraoka et al. Expression of Recipient CD47 on Rat Insulinoma Cell Xenografts Prevents Macrophage-Mediated Rejection through SIRPa Inhibitory Signaling in Mice, Plos One 8(3) Mar. 2013.
Ueda et al. Pluripotent stem cells as a source for T cell research and clinical application, Jpn. J. Clin. Immunol., 38(2) 101-108 (2015).
Moberg et al. "Neutrophilic granulocytes are the predominant cell type infiltrating pancreatic islets in contact with ABO-compatible blood," Clinical and Experimental Immunology, 142: 125-131, 2005 (oa dtd Oct. 10, 24).
Verhoeff et al. "Evaluating the Potential for ABO-incompatible Islet Transplantion: Expression of ABH Antigens on Human Pancreata, Isolated Islets and Embryonic Stem Cell-derived Islets," Transplantation, 107(4): e98-e108, Apr. 1, 2023 (oa dtd Oct. 10, 24).

(56) References Cited

OTHER PUBLICATIONS

Dean (Dean L. Blood Groups and Red Cell Antigens [Internet]. Bethesda (MD): National Center for Biotechnology Information (US); Chapter 7, The Rh blood group, 2005 (oa dtd Oct. 10, 24).
Dean (Dean L. Blood Groups and Red Cell Antigens [Internet]. Bethesda (MD): National Center for Biotechnology Information (US); Chapter 5, The ABO blood group, 2005.
Lee et al. "Down-regulation of MHC class I expression in human neuronal stem cells using viral stealth mechanism," Biochemical and biophysical research communications 326,4 (2005): 825-835.
Blazar et al. "CD47 (Integrin-associated Protein) Engagement of Dendritic Cell and Macrophage Counterreceptors Is Required to Prevent the Clearance of Donor Lymphohematopoietic Cells," J. Exp. Med. Vol. 194, No. 4, pp. 541-549, (2001).
Anzalone, A.V. et al., Search-and-replace genome editing without double-strand breaks or donor DNA, Nature, 576 (7785): 149-157 (2019).
Arce et al., "Molecular Cloning of RhD cDNA Derived From a Gene Present in RhDPositive, But Not RhD-Negative Individuals," Blood, 82(2):651-655 (1993).
Arnould et al., Engineering of Large Nos. of Highly Specific Homing Endonucleases that Induce Recombination on Novel DNA Targets, J. Mol. Biol., 1-16 (2005).
Asgari et at, Differentiation and Transplantation of Human Induced Pluripotent Stem Cell-derived Hepatocyte-like Cells, Stem Cell Rev, DOI 10.1007/s12015-011-9330-y, 2011.
Atsavapranee, E.S. et al., Delivery technologies for T cell gene editing: Applications in cancer immunotherapy, EBioMedicine, 67:103354 (2021 ).
Bang et al., HA22 (R490A) Is a Recombinant Immunotoxin with Increased Antitumor Activity without an Increase in Animal Toxicity, Clin. Cancer Res., 11 : 1545-1550 (2005).
Bejcek et al., Development and Characterization of Three Recombinant Single Chain Antibody Fragments (scFvs) Directed against the CD19 Antigen1, Cancer Res. 55:2346-2351 (1995).
Berg and Shi, The Galvanization of Biology: A Growing Appreciation for the Roles of Zinc, Science, 271:1081-1085 (1996).
Bernareggi et al., Development of innate immune cells from human pluripotent stem cells, Exp. Hematol., 71:13-23 (2019).
Bitinaite et al., Fokl dimerization is required for DNA cleavage, Proc. Natl. Acad. Sci. USA 95:10570-10575 (1998).
Blazar et al., Strategies to Inhibit Alloantibody Production in Alloprimed Murine Recipients of Hematopoietic Stem Cell Grafts, Am. J. Transplant, 15(4):931-941 (2015).
Boch, TALEs of genome targeting, Nature Biotech. 29(2): 135-136 (2011).
Callard et al., CD19 regulation of human B cell responses. B cell proliferation and antibody secretion are inhibited or enhanced by ligation of the CD19 surface glycoprotein depending on the stimulating signal used, J. Immunology, 148(10): 2983-2987 (1992).
Carpenter et al., B-cell Maturation Antigen Is a Promising Target for Adoptive T-cell Therapy of Multiple Myeloma, Clin. Cancer Res., 19(8):2048-2060 (2013).
Carroll, D., Genome Engineering With Zinc-Finger Nucleases, Genetics Society of America, 188:773-782 (2011).
Cermak et al., Efficient design and assembly of custom TALEN and other TAL effectorbased constructs for DNA targeting, Nucl. Acids Res. 39(12): e82 1-11 (2011).
Chen et al., Directed evolution of homing endonuclease I-Seel with altered sequence specificity, Protein Ena. Des. Sel., 22(4):249-256 (2009).
Chevalier et al., Design, Activity, and Structure of a Highly Specific Artificial Endonuclease, Malec. Cell, 10:895-905 (2002).
Chevalier, B.S. and B.L. Stoddard, Homing endonucleases: structural functional insight into the catalysts of intron/intein mobility, Nucleic Acids Res., 29(18): 3757-3774 (2001).
Choulika et al., Inducation of Homologous Recombination in Mammalian Chormosomes by Using the I-Seel System of Saccharomyces cerevisiae, Mol. Cell. Biol., 15(4): 1968-1973 (1995).
Coffin et al., "The Interactions of Retroviruses and their Hosts," Retroviruses, Cold Spring Harbor Laboratory Press, 11 pages (1997).
Cohen-Tannoudji et al., I-Seel-Induced Gene Replacement at a Natural Locus in Embryonic Stem Cells, Mol. Cell. Biol., 18(3): 1444-1448 (1998).
Cronican, J.J. et al., Potent delivery of functional proteins into Mammalian cells in vitro and in vivo using a supercharged protein, ACS Chem. Biol., 5(8):747-752 (2010).
Dai, H. et al., Bispecific CAR-T cells targeting both CD19 and CD22 for therapy of adults with relapsed or refractory B cell acute lymphoblastic leukemia, J. Hematol. Oneal., 13(1):30 (2020).
Dang, Y. et al., Optimizing sgRNA structure to improve CRISPR-Cas9 knockout efficiency, Genome Biol., 16:280 (2015).
De Rie et al., Regulatory Role of CD19 Molecules in B-Cell Activation and Differentiation, Cell. Immunol., 118:368-381 (1989).
Deuse et al., Hypoimmunogenic derivatives of induced pluripotent stem cells evade immune rejection in fully immunocompetent allogeneic recipients, Nature Biotechnology, 37:252-258 (2019).
Donoho et al., Analysis of Gene Targeting and Intrachromosomal Homologous Recombination Stimulated by Genomic Double-Strand Breaks in Mouse Embryonic Stem Cells, Mol. Cell. Biol, 18(7): 4070-4078 (1998).
Doyon et al., Directed Evolution and Substrate Specificity Profile of Homing Endonucleases I-Seel, J. Am. Chem. Soc., 128:2477-2484 (2006).
Doyon et al., Enhancing zinc-finger-nuclease activity with improved obligate heterodimeric architectures, Nature Methods, 8(1):74-79 (2011).
Elliott et al., Gene Conversion Tracts from Double-Strand Break Repair in Mammalian Cells, Mol. Cell. Biol., 18 (1):93-101 (1998).
Ensembl ID No. ENSG00000175164.16, ABO, alpha 1-3-N-acetylgalactosaminyltransferase and alpha 1-3-galactosyltransferase, 2 pages, (2024).
Ensembl ID No. ENSG00000187010.21, RHD, RH blood group D antigen, 2 pages, (2024).
Ensembl ID No. ENSG00000196776, CD47 molecule, 1 page, (2024).
Ensembl ID No. ENST00000328664.9, RHD-201, RH blood aroup D antigen, 1 page, (2024).
Ensembl ID No. ENST00000342055.9, RHD-202, RH blood Qroup D antigen, 1 page, (2024).
Ensembl ID No. ENST00000357542.8, RHD-203, RH blood aroup D antigen, 1 page, (2024).
Ensembl ID No. ENST00000417538.6, RHD-204, RH blood Qroup D antigen, 1 page, (2024).
Ensembl ID No. ENST00000423810.6, RHD-206, RH blood Qroup D antigen, 1 page, (2024).
Ensembl ID No. ENST00000454452.6, RHD-207, RH blood aroup D antigen, 1 page, (2024).
Ensembl ID No. ENST00000538324.2, ABO-202, alpha 1-3-Nacetylgalactosaminyltransferase and alpha 1-3-galactosyltransferase, 1 page, (2024).
Ensembl ID No. ENST00000568195.5, RHD-209, RH blood Qroup D antigen, 1 page, (2024).
Ensembl ID No. ENST00000611156.4, ABO, alpha 1-3-N-acetylgalactosaminyltransferase and alpha 1-3-galactosyltransferase, 1 page, (2024).
Ensembl ID No. ENST00000622561.4, RHD-210, RH blood group D antigen, 1 paqe, (2024).
Ensembl ID No. ENST00000648012.1, RHD-211, RH blood group D antigen, 1 page, (2024).
Epinat et al., A novel engineered meganuclease induces homologous recombination in yeast and mammalian cells, Nucleic Acids Res. 31(11):2952-2962 (2003).
Freedman et al., Normal cellular counterparts of B cell chronic lymphocytic leukemia, Blood, 70(2): 418-427 (1987).
Friedman et al., Effective Targeting of Multiple B-Cell Maturation Antigen-Expressing Hematological Malignances by Anti-B-Cell Maturation Antigen Chimeric Antigen Receptor T Cells, Hum. Gene Ther. 29(5):585-601 (2018).

(56) References Cited

OTHER PUBLICATIONS

Fujioka, Y. et al., A novel membrane glycoprotein, SHPS-1, that binds the SH2-domain containing protein tyrosine phosphatase SHP-2 in response to mitogens and cell adhesion, Mol. Cell. Biol., 16(12):6887-6899 (1996).
Li et al. "Adipose tissue-derived mesenchymal stem cell-based liver gene delivery," Journal of Hepatology, Elsevier, Amsterdam, NL, vol. 54, No. 5, pp. 930-938, Jul. 28, 2010.
Grube et al. "ABO blood group antigen mismatch has an impact on outcome after allogeneic peripheral blood stem cell transplantation," Clinical Transplantation, Munksgaard, Copenhagen DK, vol. 30, No. 11, pp. 1457-1465, Oct. 3, 2016.
Shokrgozar et al. "ABO Blood Grouping Mismatch in Hematopoietic Stem Cell Transplantation and Clinical Guides," International Journal of Hematology-Oncology and Stem Cell Research, Jul. 27, 2018.
Hu et al. "Inhibition of polymorphonuclear cell averts cytotoxicity against hypoimmune cells in xenotransplantation," Nature Communications, vol. 16, No. 1, Apr. 18, 2025.
Herbrich et al. "Overexpression of CD200 is a Stem Cell-Specific Mechanism of Immune Escape in AML," Blood, vol. 136, No. Supplement 1, pp. 14-15, Nov. 5, 2020.
Van Rees Dieke J et al. "Immunoreceptors on neutrophils," Seminars in Immunology, W.B. Saunders Company, Pa, US, vol. 28, No. 2, pp. 94-108, Mar. 11, 2016.
Tavakkoli et al. "Do preclinical studies suggest that CD99 is a potential therapeutic targeet in acute myeloid leukemia and the myelodysplastic syndromes?", Expert Opinion on Therapeutic Targets, vol. 22, No. 5, pp. 381-383. Apr. 20, 2018.
Garver et al. "Clonal Gene Therapy: Transplanted Mouse Fibroblast Clones Express Human alpha1-Antitrypsin Gene in Vivo," Science, vol. 237, No. 4816, pp. 762-764, Aug. 14, 1987.
PCT Search Report and Written Opinion dated Jul. 22, 2021, for PCT Application No. PCT/US2021/013499.
U.S. Appl. No. 62/915,601, filed Oct. 15, 2019.
Borel et al., Editing out five Serpina1 paralogs to create a mouse model of genetic emphysema. Proc Natl Acad Sci USA 115:2788-2793 (2018).
Matzinger. Tolerance, danger, and the extended family. Rev. Immunol. 12:991-1045 (1994).
Steevels TA., Signal inhibitory receptor on leukocytes-1 (SIRL-1)negatively regulates the oxidative burst in humanphagocytes. Eur J Immunol. 43(5): 1297-308 (2013).
Stefanska J. Apocynin: Molecular Aptitudes. Mediators Inflamm. 2008:106507 (2008).
Von Nussbaum F., Freezing the Bioactive Conformation to Boost Potency: The Identification of BAY 85-8501, a Selective and Potent Inhibitor of Human Neutrophil Elastase for Pulmonary Diseases. Chem. Med. Chem. 10:1163-73 (2015).
Ang et al. A Roadmap for Human Liver Differentiation from Pluripotent Stem Cells. Cell Rep. Feb. 2, 20180;22 (8):2190-2205.
Bargehr et al. Epicardial cells derived from human embryonic stem cells augment cardiomyocyte-driven heart regeneration. Nat Biotechnol. Aug. 2019;37(8): 895-906.
Barrera et al. CD47 overexpression is associated with decreased neutrophil apoptosis/phagocytosis and poor prognosis in non-small-cell lung cancer patients. Br J Cancer. Jul. 2, 20175;117(3):385-397.
Cham et al. Immunotherapeutic Blockade of CD47 Inhibitory Signaling Enhances Innate and Adaptive Immune Responses to Viral Infection. Cell Rep. Apr. 1, 20204;31(2): 107494.
Daher et al. Outlook for New CAR-Based Therapies with a Focus on CAR NK Cells: What Lies Beyond CAR-Engineered T Cells in the Race against Cancer. Cancer Discov. Jan. 2021; 11(1):45-58.
Forrester et al. Good news-bad news: the Yin and Yang of immune privilege in the eye. Front Immunol. Nov. 2, 20127:3:338.
Globig et al. The B1-adrenergic receptor links sympathetic nerves to T cell exhaustion. Nature. Oct. 2023;622 (7982):383-392.
Hatherley et al. Structures of CD200/CD200 receptor family and implications for topology, regulation, and evolution. Structure. May 7, 2013;21(5):820-32.
He et al. Defined tumor antigen-specific T cells potentiate personalized TCR-T cell therapy and prediction of immunotherapy response. Cell Res. Jun. 2022;32(6):530-542.
Li et al. Strength of CAR signaling determines T cell versus ILC differentiation from pluripotent stem cells. Cell Rep. Mar. 2, 20238;42(3): 112241.
Mansilla-Soto et al. HLA-independent T cell receptors for targeting tumors with low antigen density. Nat Med. Feb. 2022;28(2):345-352.
Pavan et al. A cloaked human stem-cell-derived neural graft capable of functional integration and immune evasion in rodent models. Cell Stem Cell. May 1, 2025;32(5): 710-726.
Ruella et al. Induction of resistance to chimeric antigen receptor T cell therapy by transduction of a single leukemic B cell. Nat Med. Oct. 2018; 24(10): 1499-1503.
Schietinger et al. Tumor-Specific T Cell Dysfunction Is a Dynamic Antigen-Driven Differentiation Program Initiated Early during Tumorigenesis. Immunity. Aug. 1, 20166;45(2): 389-401.
Shafer et al. Cancer Therapy With TCR-Engineered T Cells: Current Strategies, Challenges, and Prospects. Front Immunol. Mar. 3, 2022:13:835762.
Zhang et al. CD47 decline in pancreatic islet cells promotes macrophage-mediated phagocytosis in type I diabetes. World J Diabetes. Jun. 1, 20205;11(6):239-251.
Goodyear. Stanford University. Pilot Study of alpha1-antitrypsin to Treat Neuromyelitis Optica Relapses (A1AT for NMO), ClinicalTrials.gov, 2014.
Polverino E. Chest. The Role of Neutrophil Elastase Inhibitors in Lung Diseases. 152(2):249-262 (2017).
Watz H., Pulm. Pharmacol. Ther. Safety and efficacy of the human neutrophil elastase inhibitor BAY 85-8501 for the treatment of non-cystic fibrosis bronchiectasis: A randomized controlled trial. 2019;56:86-93 (2019).
Greenaway et al., Human cytomegalovirus DNA: BamHI, EcoRI and Pstl restriction endonuclease cleavaQe maps, Gene, 18:355-360 (1982).
Guo et al., Directed Evolution of an Enhanced and Highly Efficient Fokl Cleavage Domain for Zinc Finger Nucleases, J. Mol. Biol. 400:96-107 (2010).
Haft, D.H. et al., A guild of 45 CRISPR-associated (Gas) protein families and multiple CRISPR/Cas subtypes exist in prokaryotic aenomes, PLoS Comput. Biol., 1 (6):e60 (2005).
Herbst et al., B-Cell Depletion In Vitro and In Vivo with an Afucosylated Anti-CD19 Antibody, J. Pharmacol. Exp. Ther., 335:213-222 (2010).
Ho et al., In Vitro Antibody Evolution Targeting Germline Hot Spots to Increase Activity of an Anti-CD22 Immunotoxin, J. Biol. Chem., 280(1):607-617 (2005).
Hockemeyer et al., Genetic engineering of human ES and iPS cells using TALE nucleases, Nat. Biotechnol., 29 (8):731-734 (2011).
Hsu et al., "DNA targeting specificity of RNA-guided Cas9 nucleases," Nature Biotechnology, 31 (9): 827-832 (2013).
International Search Report and Written Opinion received in International Application No. PCT/US2021/013140, mailed Jun. 21, 2021.
International Search Report for PCT/US2022/074846, filed Aug. 11, 2022, 5 pages, (mailed Aug. 28, 2023).
Invitation to Pay Additional Fees for PCT/US2022/074846, filed Aug. 11, 2022, 3 pages, (mailed May 22, 2023).
Iriguchi et al., A clinically applicable and scalable method to regenerate T-cells from iPSCs for off-the-shelf T-cell immunotherapy, Nature Communications, 12:430:1-15 (2021).
Jinek, M. et al., A programmable dual-RNA-guided DNA endonuclease in adaptive bacterial immunity, Science, 337 (6096): 816-821 (2012).
Kansas and Tedder, Transmembrane signals generated through MHC class II, CD19, CD20, CD39, and CD40 antigens induce LFA-1-dependent and independent adhesion in human B cells through a tyrosine kinase-dependent pathway, J. Immunol., 147:4094-4102 (1991).

(56) References Cited

OTHER PUBLICATIONS

Katoh, M. et al., Exploitation of the interaction of measles virus fusogenic envelope proteins with the surface receptor CD46 on human cells for microcell-mediated chromosome transfer, BMC Biotechnol., 10:37 (2010).
Kim et al., Hybrid restriction enzymes: Zinc finger fusions to Fok I cleavage domain, Proc. Natl. Acad. Sci. USA, 93:1156-1160 (1996).
Klompe, S.E. et al., Transposon-encoded CRISPR-Cas systems direct RNA-guided DNA intearation, Nature, 571 (7764):219-225 (2019).
Knorr et al., "Clinical-Scale Derivation of Natural Killer Cells From Human Pluripotent Stem Cells for Cancer Therapy," Stem Cells Transl Med. 2:274-283 (2013).
Lacoste et al., "An Efficient and Reversible Transposable System for Gene Delivery and Lineage-Specific Differentiation in Human Embryonic Stem Cells," Cell Stem Cell, 5:332- 342 (2009).
Lam, N. et al., Anti-BCMA chimeric antigen receptors with fully human heavy-chain-only antigen recognition domains, Nat. Commun., 11 (1 ):283 (2020).
Lavillette, D. et al., The envelope glycoprotein of human endogenous retrovirus type W uses a divergent family of amino acid transporters/cell surface receptors, J. Viral., 76( 13) :6442-6452 (2002).
Leavitt et al., Human Immunodeficiency Virus Type 1 Integrase Mutants Retain In Vitro Integrase Activity yet Fail To Integrate Viral DNA Efficiently during Infection, J. Virol., 70(2): 721-728 (1996).
Lewis et al., "Passage through Mitosis Is Required for On co retroviruses but Not for the Human Immunodeficiency Virus," J. Virol.. 68(1):510-516 (1994).
Liu et al., Context-dependent DNA recognition code for C2H2 zinc-finger transcription factors, Bioinformatics 24 (17): 1850-1857 (2008).
Meeker et al., A Unique Human B Lymphocyte Antigen Defined by a Monoclonal Antibody, Hybridoma, 3(4):305-320 (1984).
Miller et al., A Tale nuclease architecture for efficient genome editing, Nat. Biotechnol., 29(2): 143-148 (2011).
Mitani, Y. et al., In vivo myomaker-mediated heterologous fusion and nuclear reprogramming, Faseb J., 31 (1):400-411 (2017).
Mohamed et al., "Allelic variance among ABO blood group genotypes in a population from the western region of Saudi Arabia," Blood Res., 15(4):274-278 (2016).
Moon et al., "Recent advances in the CRISPR genome editing tool set," Experimental & Molecular Medicine, 51:130 (2019).
Moscou et al., A Simple Cipher Governs DNA Recognition by TAL Effectors, Science, 326: 1501 (2009).
Naldini et al., "Efficient transfer, integration, and sustained long-term expression of the transgene in adult rat brains injected with a lentiviral vector," Proc. Natl. Acad. Sci. USA, 93: 11382-11388 (1996).
National Blood Transfusion Committee, "The appropriate use of group O D negative red cells," NHS, hltgs://wwwJransfusionguidelines.orq/documenl-library/docurnents/nbtcaggmr2riale-use-of-cn•oug-o-d-neoative-rnd-cells-final-Qdf, 1-8 (2019).
NCBI Reference Sequence: NC_000009.11. Homo sapiens chromosome 9, GRCh37.p13 Primary Assembly, 3 pages, (2013).
NCBI Reference Sequence: NG_007494.1, Homo sapiens Rh blood group D antigen (RHD), RefSeaGene (LRG 796) on chromosome 1, 20 pages, (2024).
Nesbitt, R.L., Targeted Intracellular Therapeutic Delivery Using Liposomes Formulated with Multifunctional Fast Proteins, Paper 388, 126 paaes, (2012).
Ni et al., Hematopoietic and Nature Killer Cell Development from Human Pluripotent Stem Cells, Methods Mol. Biol., 1029:33-41 (2013).
Nicholson et al., Construction and Characterisation of a Functional CD19 Specific Single Chain Fv Fragment for Immunotherapy of B Lineage Leukaemia and Lymphoma, Mol. Immun., 34(16-17): 1157-1165 (1997).
Nightingale et al., "Transient Gene Expression by Nonintegrating Lentiviral Vectors," Mol. Ther., 13:1121-1132 (2006).
Pezzutto et al., CD19 Monoclonal Antibody HD37 Inhibits Anti-Immunoglobulin-Induced B Cell Activation and Proliferation1, J. Immunol., 138(9):2793-2799 (1987).
Podbilewicz, B., Virus and cell fusion mechanisms, Annu. Rev. Cell Dev. Biol., 30:111-139 (2014).
Puchta et al., Homologous recombination in plant cells is enhanced by in vivo induction of double strand breaks into DNA by a site-specific endonuclease, Nuc. Ac. Res., 21(22):5034-5040 (1993).
Puchta et al., Two different but related mechanisms are used in plants for the repair of genomic double-strand breaks by homologous recombination, Proc. Natl. Acad. Sci. USA, 93:5055-5060 (1996).
Quinn, M.E. et al., Myomerger induces fusion of non-fusogenic cells and is required for skeletal muscle development, Nat. Commun., 8:15665 (2017).
Ran, F.A. et al., In vivo genome editing using Staphylococcus aureus Cas9, Nature, 520(7546): 186-191 (2015).
Rouet et al., Introduction of Double-Strand Breaks into the Genome of Mouse Cells by Expression of a Rare-Cutting Endonuclease, Mol. Cell. Biol., 14(12):8096-8106 (1994).
Sapir, A. et al., Viral and developmental cell fusion mechanisms: conservation and diveraence, Dev. Cell., 14 (1 ): 11-21 (2008).
Sargent et al., Repair of Site-Specific Double-Strand Breaks in a Mammalian Chromosome by Homologous and Illegitimate Recombination, Mol. Cell. Biol., 17(1 ):267-77 (1997).
Seligman et al., Mutations altering the cleavage specificity of a homing endonuclease, Nucleic Acids Res., 30 (17):3870-3879 (2002).
Seltsam et al., "The nature of diversity and diversification at the ABO locus," Blood, 102(8):3035-3042, (2003).
Sera et al., Rational Design of Artificial Zinc-Finger Proteins Using a Nondegenerate Recognition Code Table, Biochemistry, 41:7074-7081 (2002).
Sha, H. et al., Chimaeric antigen receptor T-cell therapy for tumour immunotherapy, Bioscience Reports, 37:1-12 (2017).
PCT Search Report and Written Opinion for PCT/US2018/013688, dated May 25, 2018.
Rong, Zhili et al. "An Effective Approach to Prevent Immune Rejection of Human ESC-Derived Allografts," Cell Stem Cell, vol. 14, No. 1, pp. 121-130, Jan. 2014.
Lu, Pengfei et al. "Generating Hypoimmunogenic Human Embryonic Stem Cells by the Disruption of Beta 2-Microglobulin," Stem Cell Reviews, vol. 9, No. 6, pp. 806-813, Aug. 2013.
Barclay, Neil et al. "The Interaction Between Signal Regulatory Protein Alpha and CD47: and Structure, Function, and Therapeutic Target," Annual Review of Immunology, vol. 32, No. 1, pp. 25-50, Mar. 2014.
PCT Search Report and Written Opinion for PCT/US2019/042123, dated Nov. 1, 2019.
Xiang, Yr et al. "Eating" Cancer Cells by Blocking CD47 Signaling: Cancer Therapy by Targeting the Innate Immune Checkpoint, Cancer Transl Med, 3(6): 200-8 (2017).
Deuse, T et al. Hypoimmunogenic derivatives of induced pluripotent stem cells evade immune rejection in fully immunocompetent allogeneic recipients, Nature Biotechnology, vol. 37, No. 3, pp. 252-258 (2019).
PCT Search Report and Written Opinion for PCT/US2019/042117, dated Jan. 7, 2020.
Wang et al. Targeted Disruption of the B2-Microglobulin Gene Minimizes the Immunogenicity of Human Embryonic Stem Cells, Stem Cells Translational Medicine, 4:1234-1245 (2015).
Xu, Ling et al. The use of suicide gene systems in vascular cells in vitro, Cell Research 8, 73-78 (1998).
Lakshmipathy, Uma et al. Pluripotent Stem Cells Methods and Protocols, Spring Protocols, Humana Press (2013).
Barese, Cecilia N. et al. Thymidine Kinase Suicide Gene-mediated Ganciclovir Ablation of Autologous Gene-modified Rhesus Hematopoiesis, Molecular Therapy vol. 20. No. 10 (2012).
Wu, Chuanfeng et al. Development of an inducible caspase-9 safety switch for pluripotent stem cell-based therapies, Molecular Therapy—Methods & Clinical Development, 1, 14053 (2014).

(56) References Cited

OTHER PUBLICATIONS

Di Stasi, Antonio et al. Inducible Apoptosis as a Safety Switch for Adoptive Cell Therapy, The New England Journal of Medicine, 365:1673-83 (2011).
Tey, Siok-Keen et al. Inducible Caspase 9 Suicide Gene to Improve the Safety of Allodepleted T Cells after Haploidentical Stem Cell Transplantation, Biology of Blood and Marrow Transplantation, 13:913-924 (2007).
U.S. Appl. No. 62/698,941, filed Jul. 17, 2018.
U.S. Appl. No. 62/698,965, filed Jul. 17, 2018.
U.S. Appl. No. 62/698,973, filed Jul. 17, 2018.
U.S. Appl. No. 62/698,978, filed Jul. 17, 2018.
U.S. Appl. No. 62/698,981, filed Jul. 17, 2018.
U.S. Appl. No. 62/698,984, filed Jul. 17, 2018.
Abraches et al. Neural Differentiation of Embryonic Stem Cells In Vitro: A Road Map to Neurogenesis in the Embryo, PLoS One 4(7), 2009.
Adhikary, S. & Eilers, M., Transcriptional Regulation and Transformation By Myc Proteins, Nat. Rev. Mol. Cell Biol. 6:635-645, 2005.
Altschul et al., Basic Local Alignment Search Tool, J. Mol. Biol. 215:403-410, 1990.
Asgari et al., Differentiation and Transplantation of Human Induced Pluripotent Stem Cell-derived Hepatocyte-like Cells, Stem Cell Rev, DOI 10.1007/s12015-011-9330-y, 2011.
Burridge et al., A Universal System for Highly Efficient Cardiac Differentiation of Human Induced Pluripotent Stem Cells That Eliminates Interline Variability, PLoS One, 6(4):18293, 2011.
Chong et al. Human Embryonic Stem Cell-Derived Cardiomyocytes Regenerate Non-Human Primate Hearts, Nature 510(7504):273-7, 2014.
Cowan, C. A. et al. Derivation of Embryonic Stem-Cell Lines from Human Blastocysts, New England J. Med. 350:13, 2004.
Dang, D. T. et al. The biology of the mammalian Krüppel-like family of transcription factors, Int. J. Biochem. Cell Biol. 32:1103-1121, 2000.
Diecke et al. Novel codon-optimized mini-intronic plasmid for efficient, inexpensive, and xeno-free induction of pluripotency, Sci Rep. 5:8081, 2015.
Doudna and Charpentier. The new frontier of genome engineering with CRISPR-Cas9, Science 346, 2014.
Gornalusse et al. HLA-E-expressing pluripotent stem cells escape allogeneic responses and lysis by NK cells, Nature Biotech, 35(8):765-772, 2017.
Huangfu, et al. Induction of pluripotent stem cells by defined factors is greatly improved by small molecule compounds, Nature Biotechnol. 26 (7): 795, 2008.
Kamao et al. Characterization of Human Induced Pluripotent Stem Cell-Derived Retinal Pigment Epithelium Cell Sheets Aiming for Clinical Application, Stem Cell Reports 2:205-18, 2014.
Kattman et al. Stage-Specific Optimization of Activin/Nodal and BMP Signaling Promotes Cardiac Differentiation of Mouse and Human Pluripotent Stem Cell Lines, Cell Stem Cell 8:228-240, 2011.
Kawamura et al. Cardiomyocytes Derived from MHC-Homozygous Induced Pluripotent Stem Cells Exhibit Reduced Allogeneic Immunogenicity in MHC-Matched Non-human Primates, Stem Cell Reports 6(3): 312-320, 2016.
Kurmann et al. Regeneration of thyroid function by transplantation of differentiated pluripotent stem cells, 17(5): 527-542, 2015.
Liu et al. Efficient Differentiation ofMouse Embryonic Stem Cells into Insulin-Producing Cells, Exp. Diabetes Res, vol. 2012, Article ID 201295, 2012.
Liu et al., Human ESC-Derived Cardiomyocytes Restore Function in Infarcted Hearts of Non-Human Primates, Nat. Biotechnol. 36(7):597-605, 2018.
Loh et al. Mapping the pairwise choices leading from pluripotency to human bone, heart and other mesoderm cell-types, Cell, 166(2): 451-467, 2016.
Mandai et al. Autologous Induced Stem-Cell-Derived Retinal Cells for Macular Degeneration, New England Journal of Medicine, 376:1038-46, 2017.
Muraro et al. A Single-Cell Transcriptome Atlas of the Human Pancreas, Cell Systems 3, 385-394, 2016.
Needleman & Wunsch, A General Method Applicable to the Search for Similarities in the Amino Acid Sequence of Two Proteins, J. Mol. Biol. 48:443, 1970.
Pagliuca et al. Generation of Functional Human Pancreatic b Cells In Vitro, Cell 159, 428-439, 2014.
Pearson & Lipman, Improved tools for biological sequence comparison, Proc. Nat'l. Acad. Sci. USA 85:2444, 1988.
Pettinato et al. Scalable Differentiation of Human iPSCs in a Multicellular Spheroid-based 3D Culture into Hepatocyte-like Cells through Direct Wnt/β- catenin Pathway Inhibition, Scientific Reports | 6:32888 | DOI: 10.1038/srep32888, 2016.
Prasain et al. Differentiation of human pluripotent stem cells to cells similar to cord-blood endothelial colony-forming cells, Nat Biotechnol. 32(11): 1151-1157, 2014.
Ryan et al. POU domain family values: flexibility, partnerships, and developmental codes, Genes Dev. 11:1207-1225, 1997.
Saljo et al. HLA and Histo-Blood Group Antigen Expression in Human Pluripotent Stem Cells and their Derivatives, Scientific Reports. 13072: 1-14, 2017.
Seki et al. Methods of induced pluripotent stem cells for clinical application, World J. Stem Cells 7(1): 116-125, 2015.
Paluch, Christopher et al. Immune Checkpoints as Therapeutic Targets in Autoimmunity, Frontiers in Immunology, vol. 9, Article 2306, Oct. 2018.
PCT Search Report and Written Opinion dated Sep. 11, 2023 for PCT/US2023/018189.
Milone et al. Chimeric Receptors Containing CD137 Signal Transduction Domains Mediate Enhanced Survival of T Cells and Increased Antileukemic Efficacy In Vivo. Molecular Therapy, vol. 17, No. 8, 1453-1464, 2009.
Themeli et al. Generation of tumor-targeted human T lymphocytes from induced pluripotent stem cells for cancer therapy. Nature Biotechnology, vol. 31, No. 10, 2013.
Romanski et al. CD19-CAR engineered NK-92 cells are sufficient to overcome NK cell resistance in B-cell malignancies. J. Cell. Mol.Med. Vol 20, No. 7, pp. 1287-1294, 2016.
Chen et al. Functional disruption of human leukocyte antigen II in human embryonic stem cell. Biol Res 48:59, 2015.
Mohit et al. Biological delivery approaches for gene therapy: Strategies to potentiate efficacy and enhance specificity. Molecular immunology, 56(4), 599-611, 2013.
Kim et al. Association of CD47 with Natural Killer Cell-Mediated Cytotoxicity of Head-and-Neck Squamous Cell Carcinoma Lines, Tumor Biology, vol. 29, pp. 28-34, 2008.
De Pelsmaeker et al. Porcine NK cells display features associated with antigen-presenting cells, Journal of Leukocyte Biology, GB, vol. 103, No. 1, pp. 129-140, 2017.
Bian et al. Cd47-Sirp[alpha] interaction and IL-10 constrain inflammation-induced macrophage phagocytosis of healthy self-cells, Proceedings of the National Academy of Sciences, vol. 113, No. 37, 2016.
Li et al. Human iPSC-Derived Natural Killer Cells Engineered with Chimeric Antigen Receptors Enhance Anti-tumor Activity, Cell Stem Cell, Amsterdam, Nl, vol. 23, No. 2, pp. 181-192, 2018.
Ray et al. CRISPRed Macrophages for Cell-Based Cancer Immunotherapy, Bioconjugate Chemistry, US, vol. 29, No. 2, pp. 445-450, 2018.
Chao et al. The CD47-SIRPa Pathway in Cancer Immune Evasion and Potential Therapeutic Implications. NIH Public Access Author Manuscript, pp. 1-13, 2012.
Weiskopf et al. Cancer immunotherapy targeting the CD47/SIRP[alpha] axis, European Journal of Cancer, Elsevier, Amsterdam NL, vol. 76, pp. 100-109, 2017.
European Supplementary Search report dated Oct. 23, 2023 for EP Application No. 20876819.2.
U.S. Appl. No. 62/846,399, filed May 10, 2019.
U.S. Appl. No. 62/855,499, filed May 31, 2019.

(56) References Cited

OTHER PUBLICATIONS

Olsson et al. Universal red blood cells-enzymatic conversion of blood group A and B antigens, Transfusion Clinique et Biologique 11: 33-39, 2004.
Pettinato et al. Scalable Differentiation of Human iPSCs in a Multicellular Spheroid-based 3D Culture into Hepatocyte-like Cells through Direct Wnt/B- catenin Pathway Inhibition, Scientific Reports | 6:32888 | DOI: 10.1038/srep32888, 2016.
Davis, Patricia M. et al. “Abatacept Binds to the Fc Receptor CD64 But Does Not Mediate Complement-Dependent Cytotoxicity or Antibody-Dependent Cellular Cytotoxicity,”The Journal of Rheumatology, vol. 34, No. 11, pp. 2204-2210 (2007).
Deuse et al., “Hypoimmunogenic derivatives of induced pluripotent stem cells evade immune rejection in fully immunocompetent allogeneic recipients”, Nature Biotechnology, Feb. 18, 2019, vol. 37, No. 3, p. 252-258.
Brown et al., “Integrin-associated protein (CD47) and its ligands”, Trends in Cell Biology, Mar. 1, 2001, vol. 11, No. 3, p. 130-135, DOI: 10.10.
EP Extended Search Report and Opinion for EP Application No. 25165433.1 dated Jul. 2, 2025.
Torres-Duran et al. “Alpha-1 antitrypsin deficiency: outstanding questions and future directions,” Orphanet Journal of Rare Diseases, vol. 13, No. 1, Dec 1, 2018.
Tamir et al. “Stem cell-based therapy for [alpha]1-antitrypsin deficiency,” Stem Cell Research & Therapy, vol. 3, No. 1, Mar. 1, 2012.
Kosuke et al. “Targeted gene correction of alpha; 1-antitrypsin deficiency in induced pluripotent stem cell,” Nature, vol. 478, No. 7369, Oct. 12, 2011.
Chiuchiolo et al. “Gene Therapy for Alpha-1 Antitrypsin Deficiency Lung Disease,” Annals of the American Thoracic Society, vol. 13, No. supplement 4, Aug. 1, 2016.
Gruntman. “Alpha-1 Antitrypsin Deficiency Protocol Therapeutics: Gene Therapy for Alpha-1 Antitrypsin Deficiency,” Retrieved from the Internet: URL:https://link.springer.com/protolo/10.1007/978-1-4939-7163-3_27. Jan. 1, 2017.

* cited by examiner

TRANSPLANTED CELL PROTECTION VIA INHIBITION OF POLYMORPHONUCLEAR CELLS

I. CROSS REFERENCE TO RELATED APPLICATIONS

This application is the U.S. National Phase Application of PCT/US2021/013499 filed Jan. 14, 2021 and claims priority under 35 U.S.C. § 119 (e) to U.S. Provisional Application No. 62/961,636, filed Jan. 15, 2020, and U.S. Provisional Application No. 63/003,264, filed Mar. 31, 2020 which are incorporated herein by reference in their entirety.

This invention was made with government support under grant no. A131847 awarded by The National Institutes of Health. The government has certain rights in the invention.

I.I SEQUENCE LISTING

The instant application contains a Sequence Listing which has been submitted electronically in ASCII format and is hereby incorporated by reference in its entirety. Said ASCII copy, created on Mar. 29, 2021, is named RUC015W_SL.txt and is 43,866 bytes in size.

II. FIELD OF THE INVENTION

The invention relates to regenerative cell therapy. In some embodiments, the regenerative cell therapy comprises transplanting cells or cell lines into patients in need thereof. In some embodiments, the cells or cell lines comprise regenerative cell therapies having a reduced sensitivity to the cell transplant recipient's immune system that kills the cells during the window of time shortly after transplantation. In some embodiments, the regenerative cell therapy is used in the treatment of injured organs and tissue. In some embodiments, the regenerative cell therapy of the invention utilizes chimeric antigen receptor (CAR) cells, endothelial cells, fibrocytes, dopaminergic neurons, pancreatic islet cells, hepatocytes, cardiomyocytes, or retinal pigment endothelium cells are used for treating diseases or rehabilitating damaged tissues. In some embodiments, the regenerative cell therapy is used to treat alpha-1 antitrypsin deficiency.

III. BACKGROUND OF THE INVENTION

Regenerative cell therapy is an important potential treatment for regenerating injured organs and tissue. With the low availability of organs for transplantation and the accompanying lengthy wait, the possibility of regenerating tissue by transplanting readily available cell lines into patients is understandably appealing. Regenerative cell therapy has shown promising initial results for rehabilitating damaged tissues after transplantation in animal models (e.g. after myocardial infarction). The propensity for the transplant recipient's immune system to reject allogeneic material, however, greatly reduces the potential efficacy of therapeutics and diminishes the possible positive effects surrounding such treatments.

Autologous induced pluripotent stem cells (iPSCs) theoretically constitute an unlimited cell source for patient-specific cell-based organ repair strategies. Their generation, however, poses technical and manufacturing challenges and is a lengthy process that conceptually prevents any acute treatment modalities. Allogeneic iPSC-based therapies or embryonic stem cell-based therapies are easier from a manufacturing standpoint and allow the generation of well-screened, standardized, high-quality cell products. Because of their allogeneic origin, however, such cell products would undergo rejection. With the reduction or elimination of the cells' antigenicity, universally-acceptable cell products could be produced. Because pluripotent stem cells can be differentiated into any cell type of the three germ layers, the potential application of stem cell therapy is wide-ranging. Differentiation can be performed ex vivo or in vivo by transplanting progenitor cells that continue to differentiate and mature in the organ environment of the implantation site. Ex vivo differentiation allows researchers or clinicians to closely monitor the procedure and ensures that the proper population of cells is generated prior to transplantation.

In most cases, however, undifferentiated pluripotent stem cells are avoided in clinical transplant therapies due to their propensity to form teratomas. Rather, such therapies tend to use differentiated cells (e.g. stem cell-derived cardiomyocytes transplanted into the myocardium of patients suffering from heart failure). Clinical applications of such pluripotent cells or tissues would benefit from a "safety feature" that controls the growth and survival of cells after their transplantation.

The art seeks stem cells capable of producing cells that are used to regenerate or replace diseased or deficient cells. Pluripotent stem cells (PSCs) may be used as a source for producing differentiated cell products because they rapidly propagate and differentiate into many possible cell types. The family of PSCs includes several members generated via different techniques and possessing distinct immunogenic features. Patient compatibility with engineered cells or tissues derived from PSCs determines the risk of immune rejection and the requirement for immunosuppression.

Embryonic stem cells (ESCs) isolated from the inner cell mass of blastocysts exhibit histocompatibility antigens that are mismatches with virtually all possible recipients. This immunological barrier cannot be solved by human leukocyte antigen (HLA)-typed banks of ESCs because even HLA-matched PSC grafts undergo rejection because of mismatches in non-HLA molecules that function as minor antigens. This is also true for allogeneic induced pluripotent stem cells (iPSCs).

Hypoimmunogenic pluripotent (HIP) cells and cell products have gene knockouts or transgenes to protect them from the cellular components of the immune system that include T cells, NK cells, and macrophages. They may also be ABO blood group type O and Rh negative (HIPO−).

Transplanted cells may be killed by mechanisms involving antibodies are antibody-dependent cellular cytotoxicity (ADCC) by NK cells, macrophages, B-cells or granulocytes and complement-dependent cytotoxicity (CDC) via activation of the complement cascade. All of those killing mechanisms utilize antibodies that bind to a target cell and activate the effector immune cells or complement. Transplanted cells that comprise enhanced CD16, CD32, or CD64 expression may evade ADCC or CDC.

Polymorphonuclear cells (PMNs) are a category of white blood cells characterized by the presence of granules in their cytoplasm and lobed nuclei that are usually in three segments. This distinguishes them from the mononuclear immune cell fraction that contains lymphocytes, macrophages, and NK cells. Neutrophils are the most abundant of the PMNs, while eosinophils, basophils, and mast cells are less frequent PMNs that are found in the bloodstream. PMNs are the most abundant type of phagocytes, constituting 60% to 65% of the total circulating white blood cells. Once PMNs have received activation signals, it takes them about thirty minutes to leave the blood and reach the site of infection or tissue damage.

PMNs do not return to the blood. They exert their effector responses and die. PMNs have three mechanisms to attack, contain, and kill evading micro-organisms: 1) Phagocytosis. PMNs are professional phagocytes and rapidly engulf invaders coated with antibodies and complement, as well as damaged cells or cellular debris. 2) PMNs secrete cytotoxic granules. Containing reactive oxygen species, cationic proteins and defensins, lysozyme, myeloperoxidase, proteolytic enzymes and cathepsin G. 3) Formation of neutrophil extracellular traps (NETs). NETs comprise of a web of chromatin and serine proteases that trap and kill microbes extracellularly.

PMNs are often the first line of defense. They quickly migrate to sites of injury and infection and, because their defense mechanisms are very unspecific, may cause significant collateral damage to healthy cells in the vicinity. They get attracted and activated by cytokines, chemokines, pathogen-associated molecular patterns (PAMPs) and danger-associated molecular patterns (DAMPs). The latter activate pattern recognition receptors (PRRs) including toll-like receptors (TLRs). PMNs overall have multiple activating or inhibitory receptors.

Thus, transplanted cell death not only reduces the efficacy of the cell product but also triggers or amplifies innate defense mechanisms involving PMNs. PMN responses localized to the time and location of transplantation that contain and scavenge debris can also kill living cells in the vicinity as collateral damage. This further reduces cell survival and intensifies the PMN response. Strategies to prevent relevant PMN activation will facilitate cell transplantation and improve the potency of cell products. This invention outlines several points of action to control PMN activation that, separately or in combination, will improve cell transplantation.

IV. SUMMARY OF THE INVENTION

The invention shows, for the first time, that activated PMNs kill cells derived from induced pluripotent stem cells in vitro. This includes unmodified and gene-edited hypoimmunogenic cells (HIP and HIPO− cells). This PMN barrier impedes the survival of transplanted cell products, including hypoimmunogenic cells, that otherwise evade peripheral blood mononuclear cell (PBMC) activation. The invention provides, for the first time, compositions and methods for evading PMN killing.

Thus, the invention provides a method of inhibiting polymorphonuclear (PMN) cells from killing a cell transplanted into a subject, comprising administering a PMN-inhibitory agent into the subject. In some aspects, the PMN inhibitory agent is an inflammatory inhibitor, a danger-associated molecular pattern (DAMP) inhibitor, a DAMP pathway inhibitor, a secretory enzyme release inhibitor, a reactive oxygen pathway inhibitor, a microtubule polymerization inhibitor, or a combination thereof.

In some aspects of the invention, the PMN-inhibitory agent is administered simultaneously with the transplanted cells or prior to the cell transplantation.

In some aspects, the PMN-inhibitory agent inhibits an interleukin 2 (IL-2), IL-2 receptor (IL-2R), toll-like receptor 4 (TLR4), TLR7, TLR8, TLR9, a toll-like receptor pathway, a neutrophil elastase (NE), a NADPH oxidase, microtubule polymerization, or wherein the PMN-inhibitory agent stimulates the cluster of differentiation 200 receptor (CD200R), PIRLα, or SIRL-1.

In other aspects, the PMN-inhibitory agent is selected from the group consisting of cyclosporin A (CsA), dexamethasone, an anti-SIRL-1 antibody, a CD200 chimera, a CD200 expressed on cells, a CD99 chimera, a CD99 expressed on cells, BAY 85-8501, alpha-1 antitrypsin (A1AT), TAK-242, apocynin, idelalisib, CpG-52364, colchicine, and the anti-TLR4 antibody NI-0101.

In a preferred aspect, the method comprises the combination of an anti-SIRL-1 antibody and BAY 85-8501 or the combination of CsA and BAY 85-8501. In other preferred aspects, the method further comprises administering Colcicine, Idelalisib, or oligonucleotide CpG-52364. In some aspects, the combination of drugs work synergistically.

In some aspects of the invention, the PMN-inhibitory agent is expressed on the surface of the transplanted cells. In preferred aspects, the PMN-inhibitory agent is CD200 or CD99.

In some aspects of the invention, the transplanted cell is derived from a hypoimmune pluripotent (HIP) cell, a HIP cell that is AB blood group O and Rhesus Factor negative (HIPO−), an induced pluripotent stem cell (iPSC), an embryonic stem cell (ESC), or a derivative thereof. In other aspects of the invention, the transplanted cell is selected from the group consisting of a chimeric antigen receptor (CAR) cell, an endothelial cell, a dopaminergic neuron, a pancreatic islet cell, a cardiomyocyte, and a retinal pigment endothelium cell.

In some aspects of the invention, the transplanted cell is from a species selected from the group consisting of a human, monkey, cow, pig, chicken, turkey, horse, sheep, goat, donkey, mule, duck, goose, buffalo, camel, yak, llama, alpaca, mouse, rat, dog, cat, hamster, and guinea pig. In a preferred aspect, the transplanted cell is human.

The invention provides a pharmaceutical composition, comprising a cell derived from a pluripotent cell or a derivative thereof, a PMN-inhibitory agent, and a pharmaceutical excipient. In some aspects, the PMN inhibitory agent is an inflammatory inhibitor, a danger-associated molecular pattern (DAMP) inhibitor, or a combination thereof.

In some aspects of the invention, the PMN-inhibitory agent and the cell are delivered to a subject using separate delivery methods.

In some aspects of the invention, the PMN-inhibitory agent inhibits an interleukin 2 (IL-2) receptor (IL-2R), toll-like receptor 4 (TLR4), TLR7, TLR8, TLR9 or any of its downstream targets, neutrophil elastase (NE) receptor, NADPH-oxidase for superoxide production, or engages cluster of differentiation 200 receptor (CD200R), PIRLα, or SIRL-1.

In some aspects of the invention, the PMN-inhibitory agent is selected from the group consisting of cyclosporin A (CsA), dexamethasone, an anti-SIRL-1 antibody, a CD200 chimera, a CD99 chimera, BAY 85-8501, alpha-1 antitrypsin (A1AT), TAK-242, apocynin, idelalisib, CpG-52364, colchicine, or the anti-TLR4 antibody NI-0101. In preferred aspects, the PMN-inhibitory agent comprises the combination of an anti-SIRL-1 antibody and BAY 85-8501 or the combination of CsA and BAY 85-8501. In other preferred aspects, the pharmaceutical composition further comprises Colcicine, Idelalisib, or oligonucleotide CpG-52364.

In some aspects of the invention, the PMN-inhibitory agent is expressed on the surface of the cell. In preferred aspects, the PMN-inhibitory agent is CD200 or CD99.

In some aspects of the invention, the pharmaceutical composition comprises a cell that is derived from a hypo-immune pluripotent (HIP) cell, a HIP cell that is AB blood group O, a Rhesus Factor negative (HIPO−), an induced pluripotent stem cell (iPSC), or an embryonic stem cell (ESC). In other aspects, the cell is selected from the group consisting of a chimeric antigen receptor (CAR) cell, an endothelial cell, a dopaminergic neuron, a pancreatic islet cell, a cardiomyocyte, and a retinal pigment endothelium cell.

In some aspects of the invention, the pharmaceutical composition comprises a transplanted cell that is from a species selected from the group consisting of a human, monkey, cow, pig, chicken, turkey, horse, sheep, goat, donkey, mule, duck, goose, buffalo, camel, yak, llama, alpaca, mouse, rat, dog, cat, hamster, and guinea pig. In a preferred aspect, the transplanted cell is human.

The invention provides a medicament for treating a disease, comprising a cell derived from a pluripotent cell or a derivative thereof, a PMN-inhibitory agent, and a pharmaceutical excipient. In some aspects, the derivative cell is selected from the group consisting of a chimeric antigen receptor (CAR) cell, an endothelial cell, a dopaminergic neuron, a pancreatic islet cell, a cardiomyocyte, and a retinal pigment endothelium cell. In other aspects, the disease is selected from the group consisting of Type I Diabetes, a cardiac disease, a neurological disease, a cancer, an ocular disease, and a vascular disease.

The invention provides a human hypo-immunogenic pluripotent (HIP) cell or a derivative thereof comprising: an overexpressed alpha-1 antitrypsin (A1AT) protein relative to a parent HIP cell; an endogenous Major Histocompatibility Antigen Class I (HLA-I) function that is reduced when compared to a parent pluripotent cell; an endogenous Major Histocompatibility Antigen Class II (HLA-II) function that is reduced when compared to the parent pluripotent cell; an increased CD47 function that reduces susceptibility to NK cell killing; an ABO blood group type O (O); and a Rhesus Factor (Rh) blood type negative (−); wherein the human hypo-immunogenic pluripotent O− (HIPO−) cell is less susceptible to rejection when transplanted into a subject when compared with an otherwise similar hypo-immunogenic pluripotent (HIP) cell that is an ABO blood group or Rh factor mismatch to the subject.

In some aspects of the invention, the A1AT protein comprises at least a 90% sequence identity to SEQ ID NO:17. In other aspects, the A1AT protein comprises the the sequence of SEQ ID NO:17.

In some aspects of the invention, the HIPO− cell further comprises an elevated level of CD16, CD32, or CD64 protein expression when compared to a parent HIPO− cell, wherein the elevated protein expression causes the modified pluripotent cell to be less susceptible to antibody dependent cellular cytotoxicity (ADCC) or complement-dependent cytotoxicity (CDC).

The invention provides a differentiated cell derived from the HIPO− cells overexpressing A1AT, wherein the differentiated cell is an endothelial cell or a fibroblast cell. In other aspects, the differentiated cell comprises an additional PMN-inhibitory agent and a pharmaceutical excipient. In preferred aspects, the additional PMN inhibitory agent is an inflammatory inhibitor, a danger-associated molecular pattern (DAMP) inhibitor, or a combination thereof. In other the additional PMN-inhibitory agent and the cell are delivered to a subject using separate delivery methods.

In other aspects, the PMN-inhibitory agent inhibits an interleukin 2 (IL-2) receptor (IL-2R), toll-like receptor 4 (TLR4), TLR7, TLR8, TLR9 or any of its downstream targets, neutrophil elastase (NE), NADPH-oxidase for superoxide production, or engages cluster of differentiation 200 receptor (CD200R), PIRLα, or SIRL-1.

In other aspects of the invention, the PMN-inhibitory agent is selected from the group consisting of cyclosporin A (CsA), dexamethasone, an anti-SIRL-1 antibody, a CD200 chimera, a CD99 chimera, BAY 85-8501, TAK-242, apocynin, idelalisib, CpG-52364, colchicine, or the anti-TLR4 antibody NI-0101.

The invention provides a method of treating an alpha-1 antitrypsin deficiency (A1AD) in a subject comprising administering the pharmaceutical composition of the invention.

V. BRIEF DESCRIPTION OF THE DRAWINGS

FIG. 1: Schematic drawing of PMN activation by IL-2 or Danger Associated Molecular Patterns (DAMPs).

Figure 2:
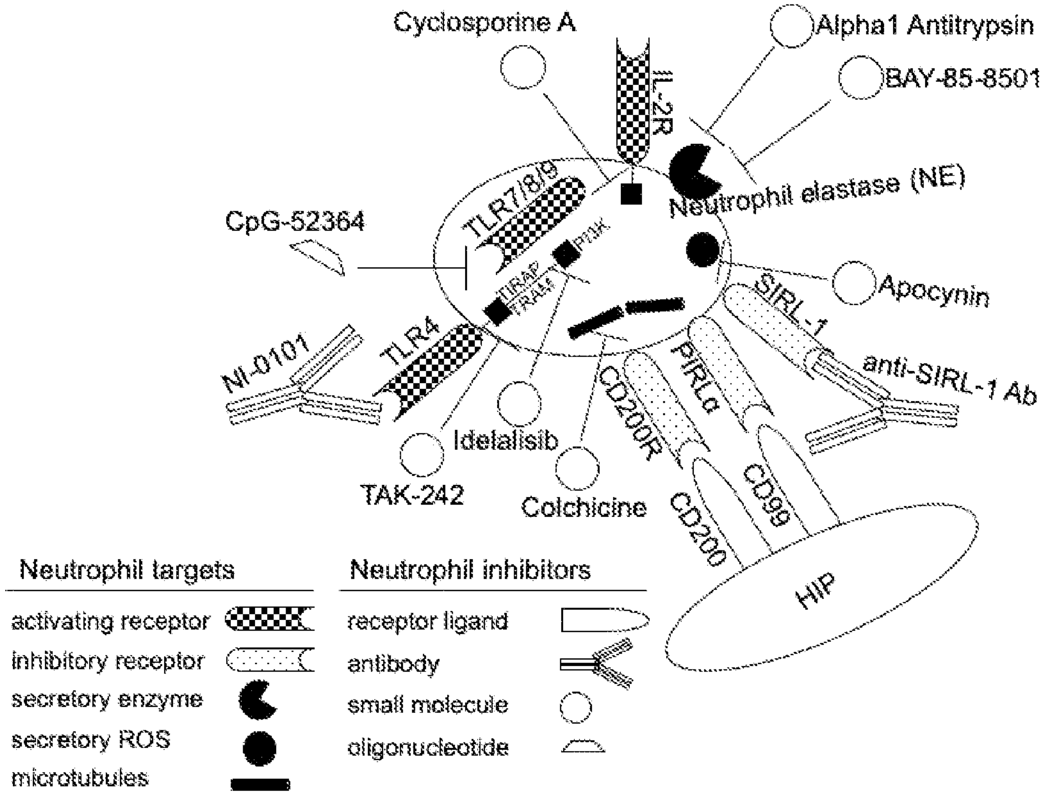

FIG. 2: Summary of the PMN inhibitory strategies. PMN target categories are summarized on the left column of the legend. Different inhibitor classes are summarized on the right column of the legend. The name of exemplary inhibitors and their corresponding receptors or targets are specified in the figure.

Figure 3:
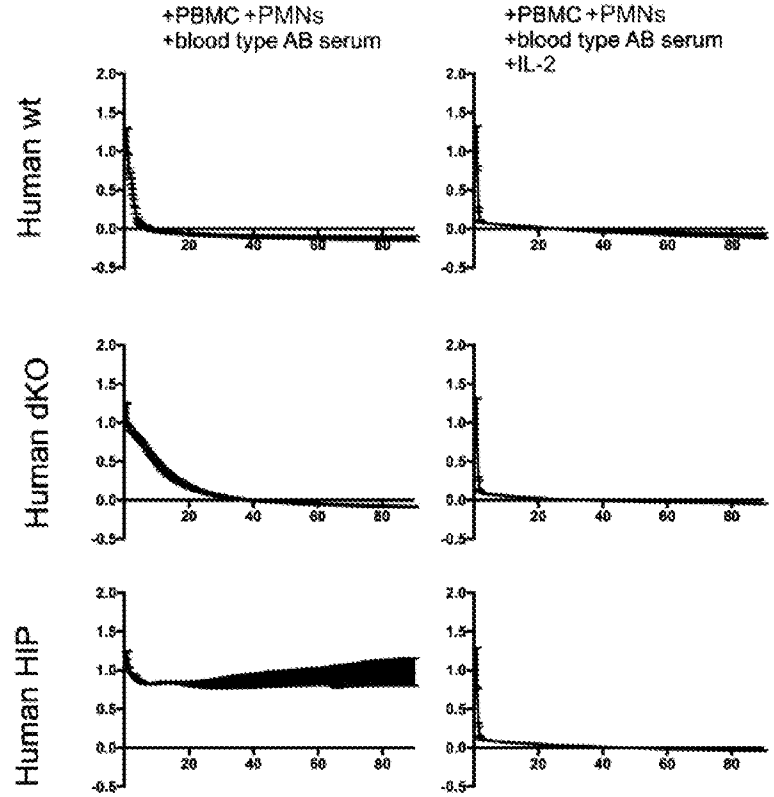

FIG. 3: The XCelligence in vitro impedance system was used as a highly sensitive platform to obtain real-time kinetics of target cell killing. Wild-type (wt) and engineered iPSCs double knock-out (dKO: HLA class I and II) and hypoimmune pluripotent (HIP) cells were differentiated into endothelial cells for this assay. All components of the human immune system found in blood were included into an effector mix combining serum (contains antibodies, complement, and soluble factors like cytokines and growth factors), peripheral blood mononuclear cells (PBMCs, contains all lymphocytes, monocytes, and NK cells) and PMNs. Notably, the serum was taken from blood type AB donors and thus did not contain blood type antibodies. Some experimental groups were treated with IL-2 which is a central cytokine involved in allograft rejection. The assays were run for a duration of 90 h. This is the maximum time period iECs can be cultured in this system before the monolayer breaks down spontaneously. XCelligence assays showed that viable allogeneic human wt iECs and dKO iECs were rejected in vitro in the absence of the pro-inflammatory cytokine IL-2. HIP cells were rejected only in the presence of IL-2. This shows that HIP iECs still undergo immune killing in an IL-2 environment.

Figure 4:
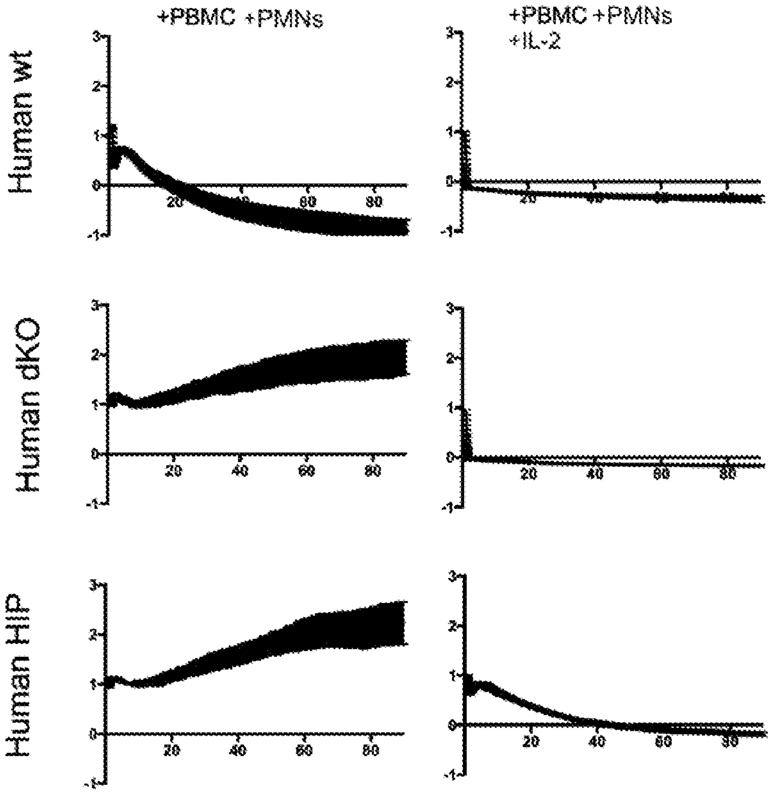

FIG. 4: XCelligence assays run with allogeneic human PBMC and PMN effectors showed that HIP iECs were rejected in the presence of the proinflammatory cytokine IL-2 even in the absence of serum.

Figure 5A:
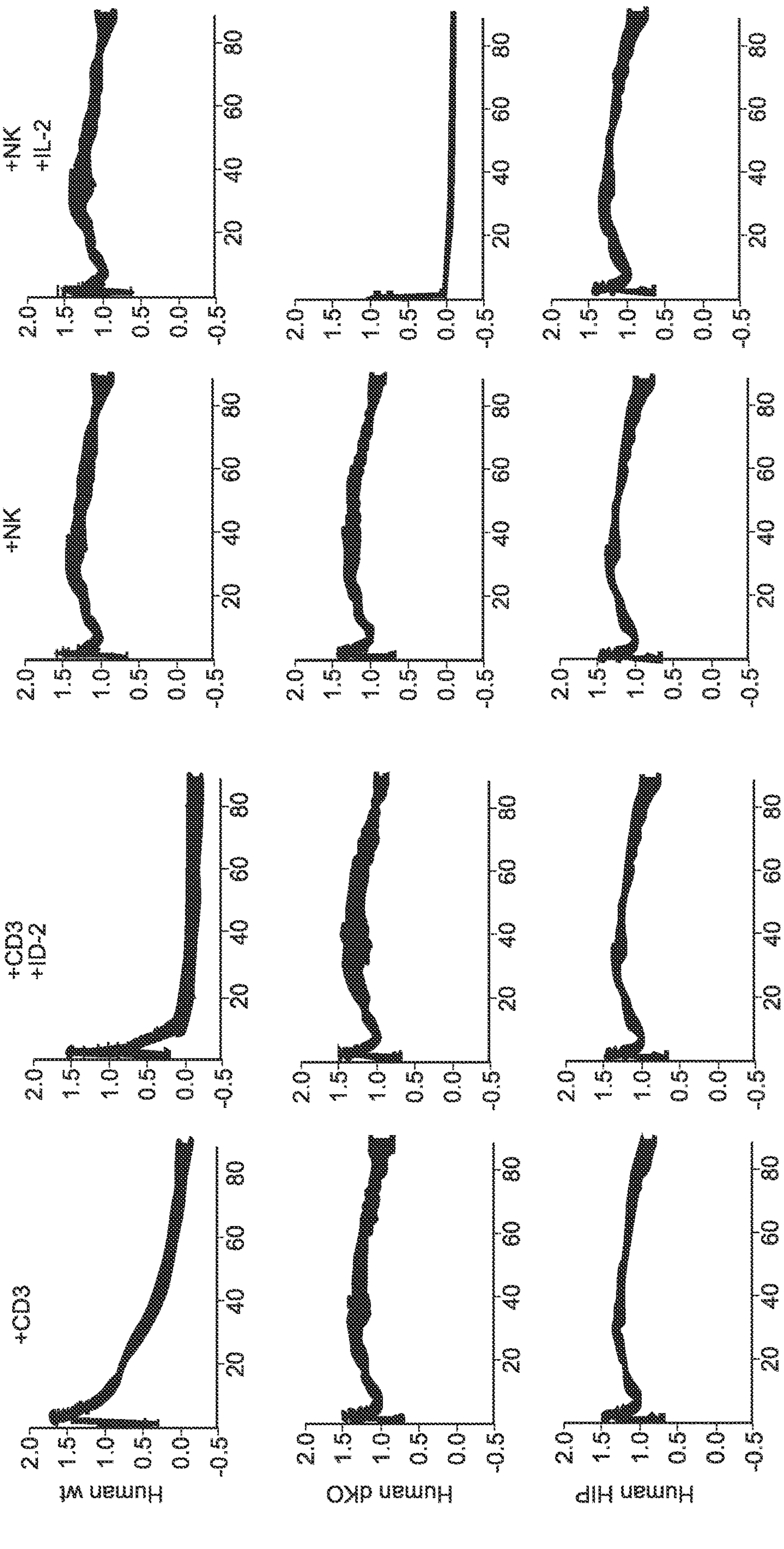
Figure 5B:
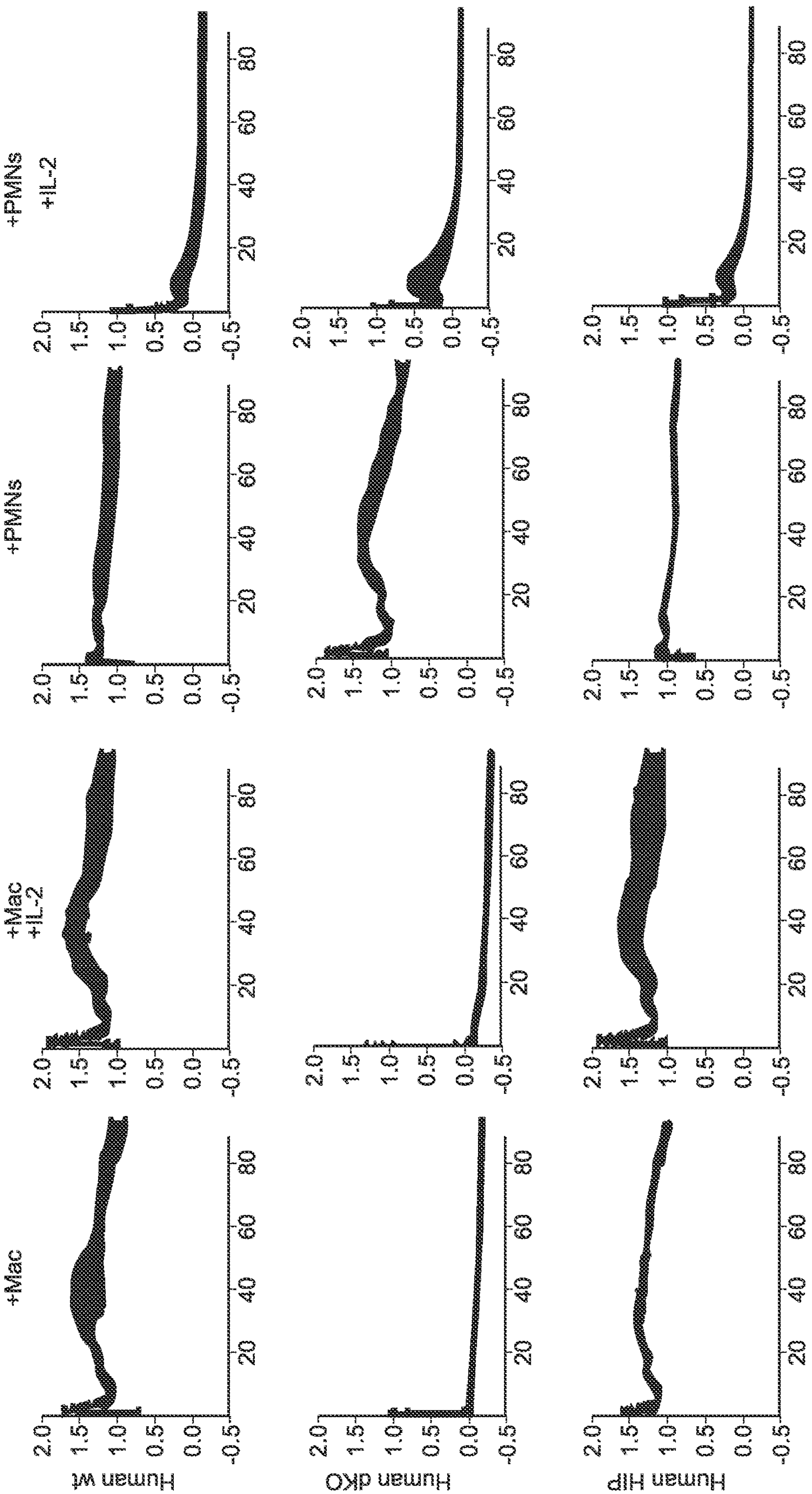

FIG. 5A: XCelligence assays run with highly selected effector cell populations showed that neither CD3+ T cells nor natural killer cells could kill HIP iECs, even in the presence of the inflammatory IL-2 cytokine. Wild-type iECs were killed by allogeneic CD3+ cells and dKO iECs were killed by IL-2 activated NK cells. FIG. 5B: HIP iECs were only killed by IL-2 activated PMNs but were resistant to macrophages (Mac) and quiescent PMNs.

Figure 6:
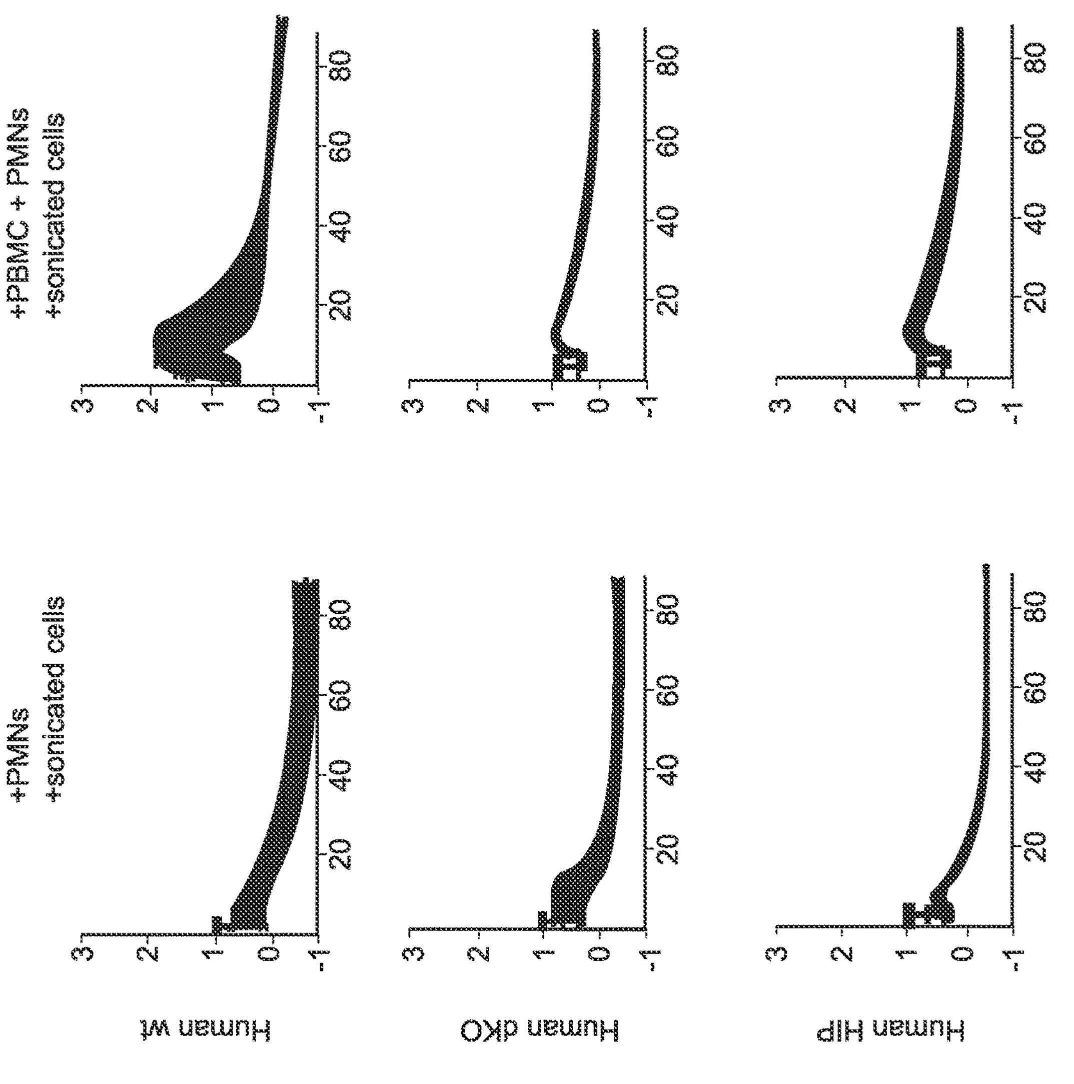

FIG. 6: In this XCelligence assay, sonicated target cells were added to the wells at the time the immune cells were added to simulate cell necrosis with DAMP leakage. They showed that necrotic cells activated PMNs that in turn killed healthy target cells as collateral damage. When PBMCs were mixed with PMNs, the killing kinetics were slower.

This was attributed to the 50% reduced PMN content in the mixed immune cell population.

Figure 7:
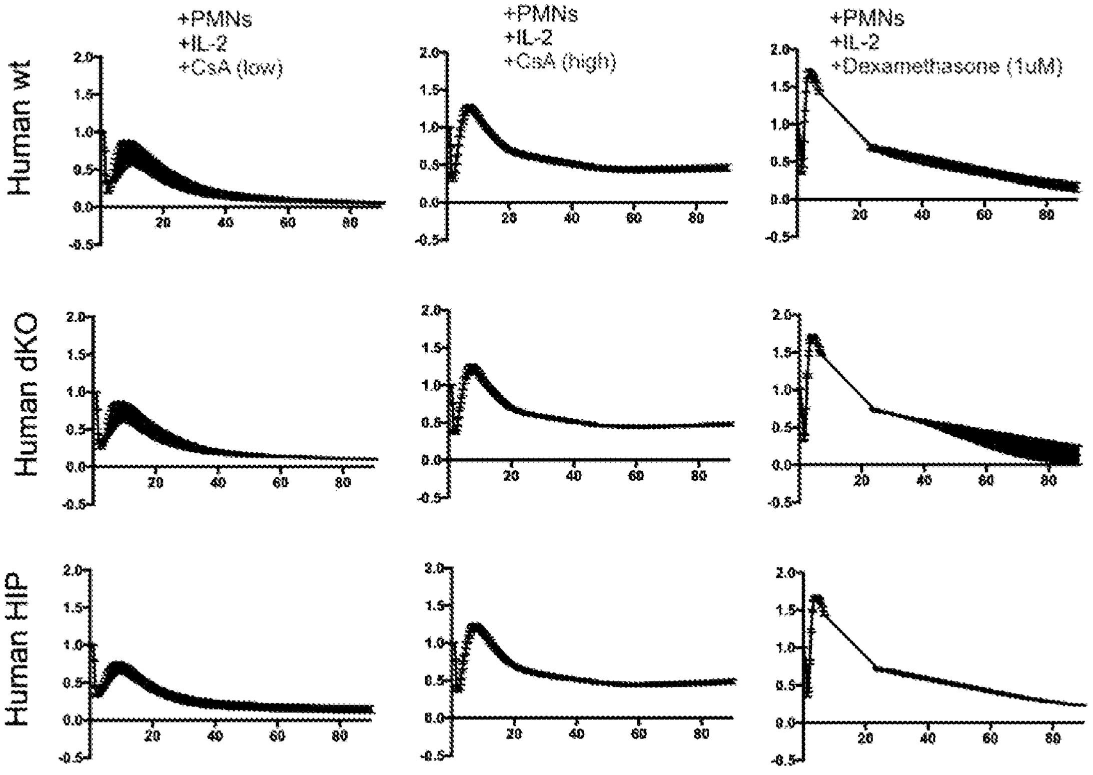

FIG. 7: Cyclosporine and dexamethasone were tested for their efficacy to dampen a PMN killing response after IL-2 stimulation. XCelligence assays were performed with human wt, dKO, and HIP iECs against IL-2 stimulated human PMNs. Cyclosporine was used in two different concentrations. Cyclosporine and dexamethasone showed some minor efficacy to reduce PMN killing.

Figure 8:
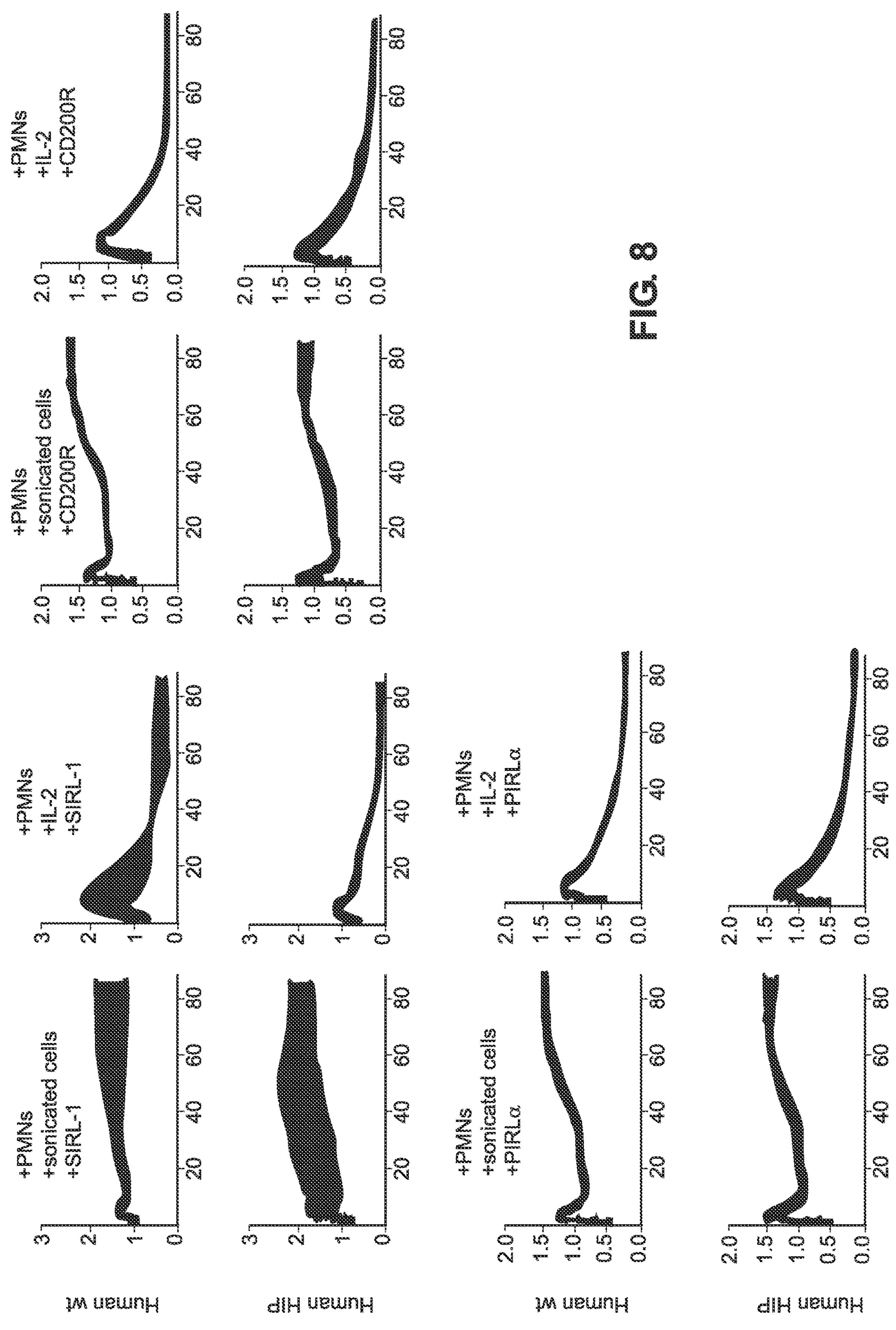

FIG. 8: The human PMNs were activated via DAMPs or IL-2 and the killing of human wt and HIP_1.0 iECs was assessed by XCelligence assays. CD200R, PIRLα, and SIRL-1 were engaged by recombinant CD200, CD99, or an inhibitory anti-SIRL-1 antibody, respectively. Engagement of those inhibitory receptors prevented PMN killing in the presence of necrotic cells. PMN killing was delayed but not prevented, however, if PMNs were stimulated with IL-2.

Figure 9A:
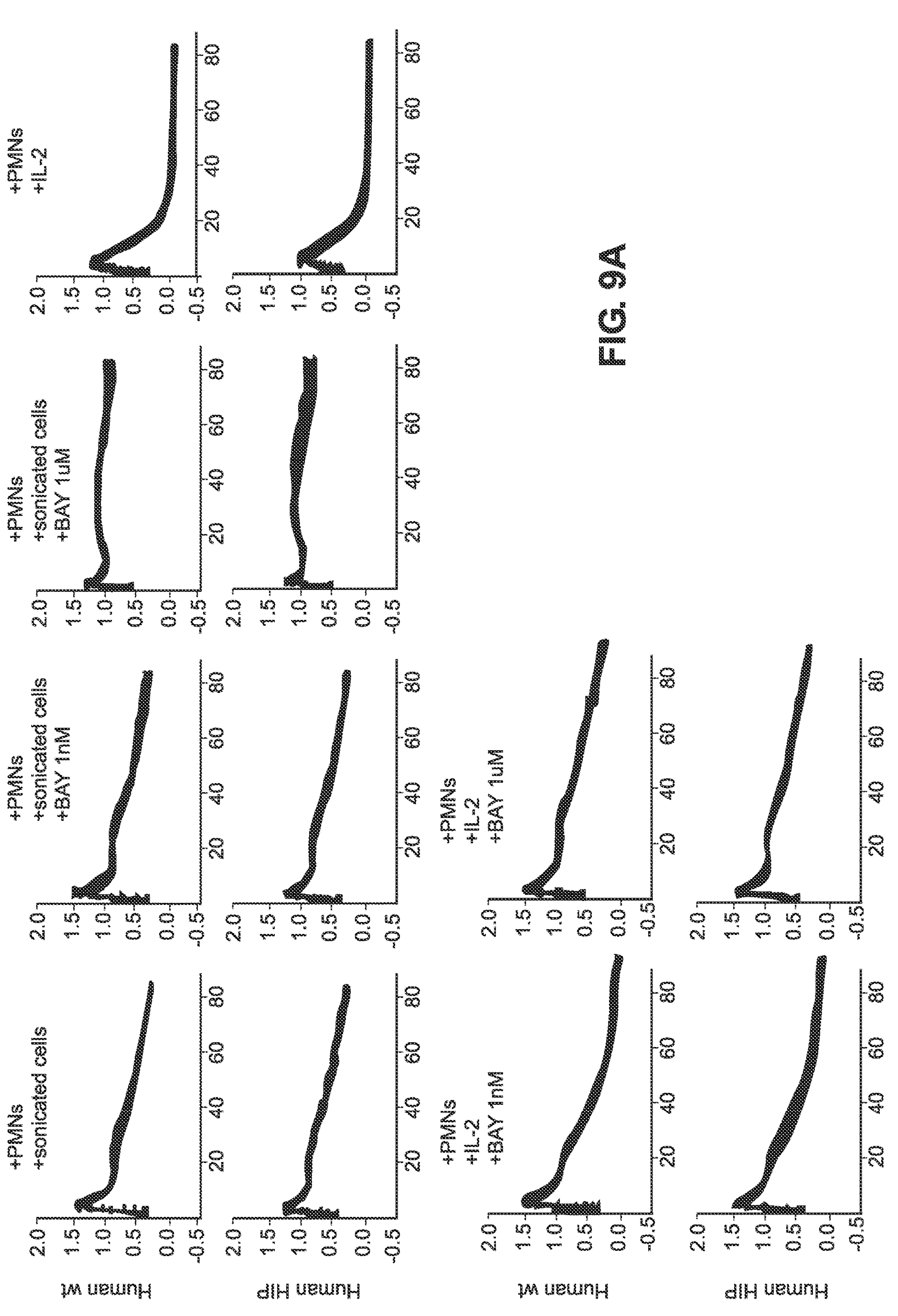

FIG. 9A: Xcelligence assays were run in the presence of the neutrophil elastase (NE) inhibitor BAY 85-8501. 1 μM BAY 85-8501 fully prevented human wt or HIP target cell killing when PMNs were activated via DAMPs from sonicated cells. The same concentration of BAY 85-8501 further delayed the target cell killing in the presence of IL-2. BAY 85-8501 at 1 nM was less effective.

Figure 9B:
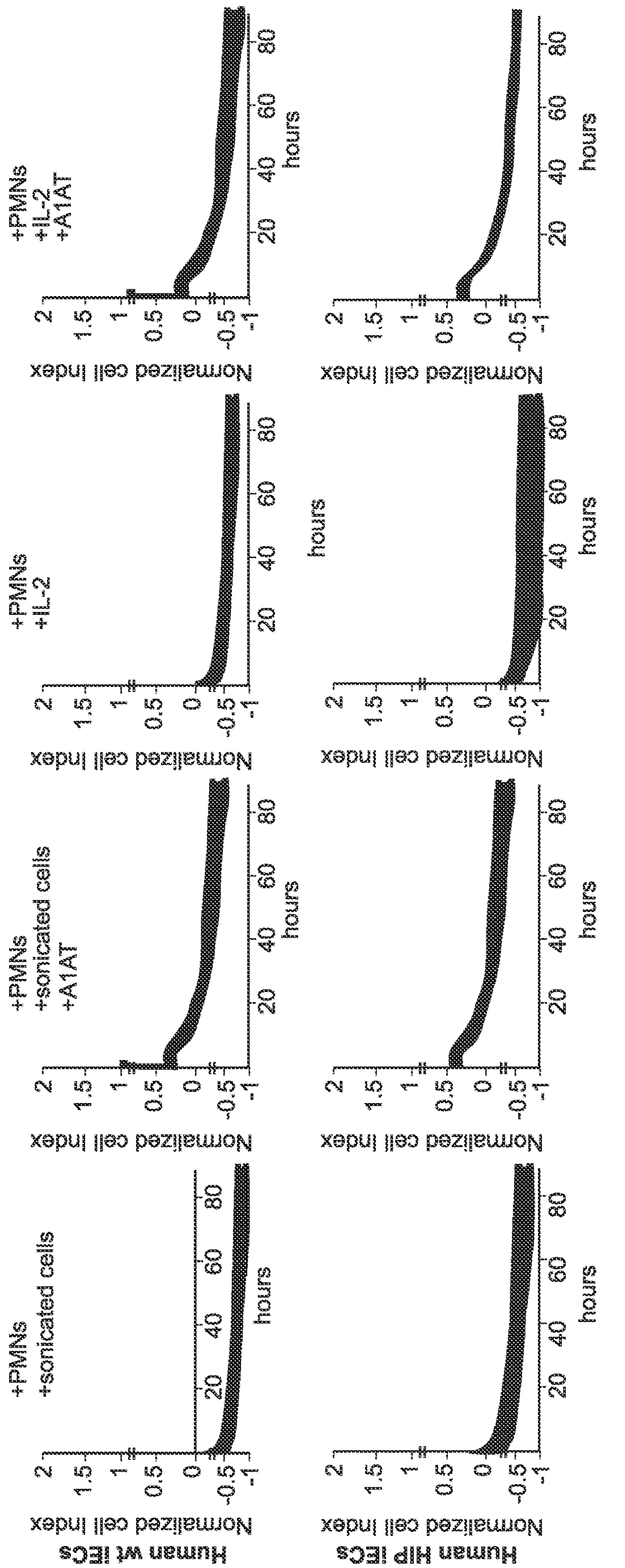

FIG. 9B: Xcelligence assays were run in the presence of the NE inhibitor alpha-1 antitrypsin (A1AT). Recombinant A1AT showed some minor activity against PMN killing of human wt and HIP iECs.

Figure 10:
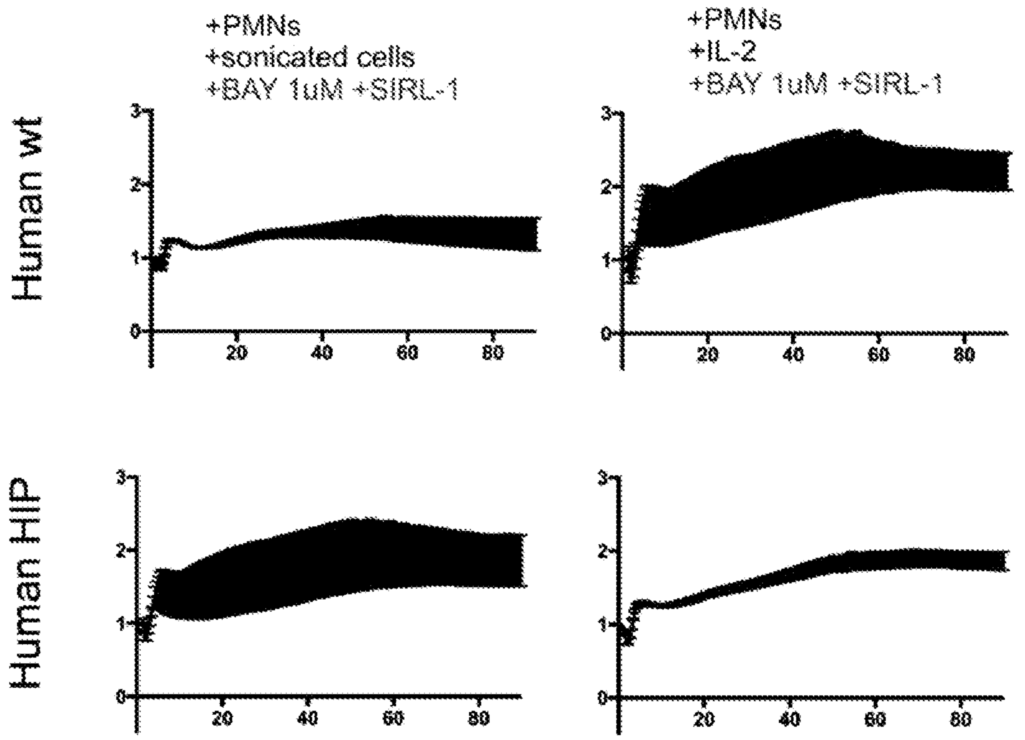

FIG. 10: The anti-SIRL-1 antibody in combination with BAY 85-8501 was a highly potent PMN inhibitor regimen in XCelligence assays with human PMNs activated via DAMPs or IL-2.

Figure 11:
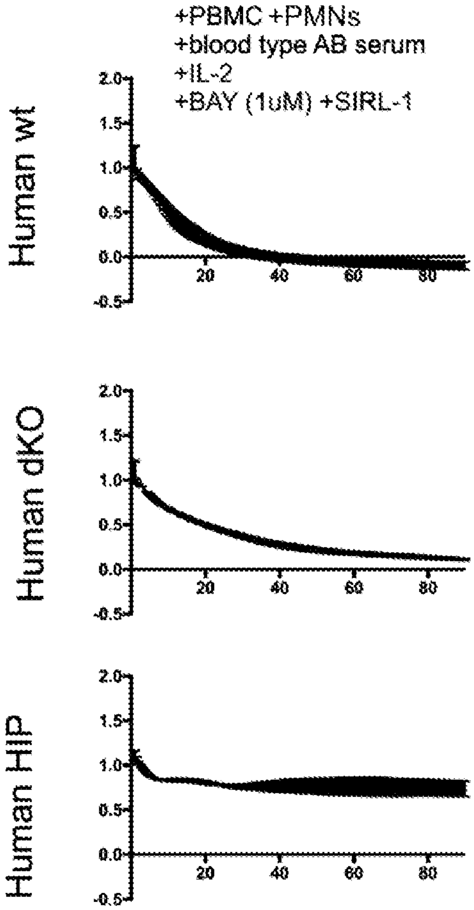

FIG. 11: BAY 85-8501 with the anti-SIRL mAb was highly efficacious in an XCelligence assay that combined all human immune system components PBMCs, PMNs, and serum in a pro-inflammatory IL-2 environment FIG. 12: Cyclosporin A (CsA) combined with BAY 85-8501 was confirmed in the presence of PBMCs and PMNs using the XCelligence assay. Low-dose CsA was combined with BAY 85-8501, with or without the anti-SIRL-1 mAb, to prevent killing of all target cells using PBMCs and PMNs as effector cells. Necrotic cells were used as stimulators. The combinations of low-dose CsA, BAY 85-8501 and anti-SIRL-1 mAb, but also low-dose CsA and BAY 85-8501 were highly effective in preventing killing of all target cells.

Figure 13:
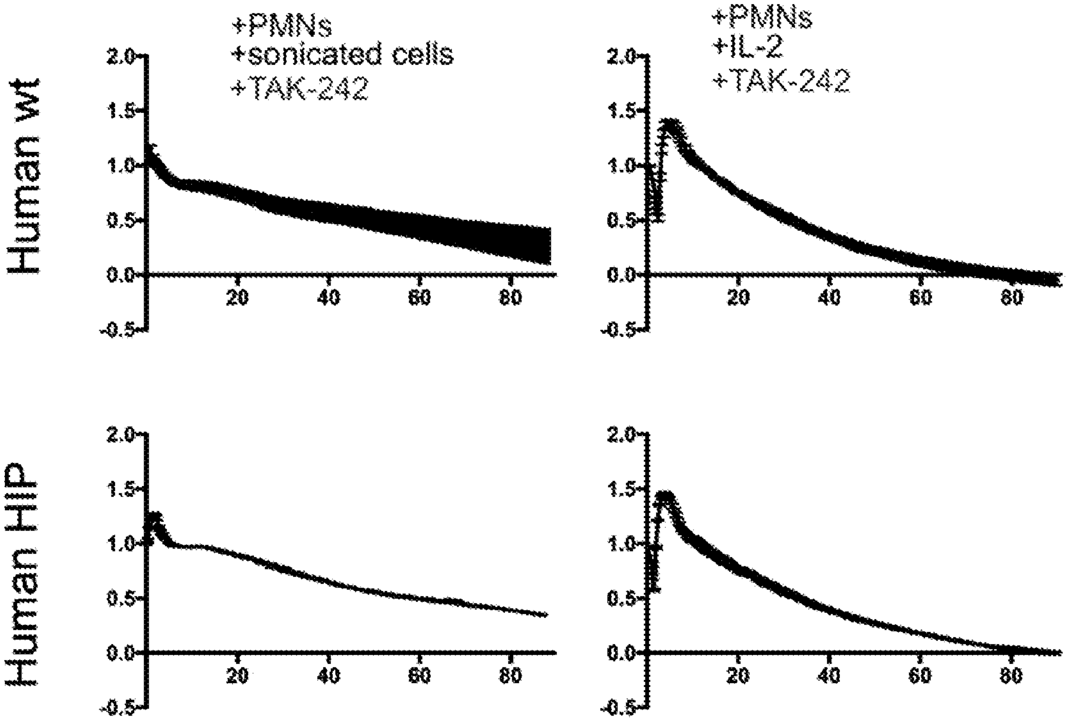

FIG. 13: PMN activation pathways were inhibited by TAK-242, a small-molecule inhibitor of TLR-4-mediated signaling. Wt and HIP iECs were used on the XCelligence platform using PMNs as effector cells and DAMPs or IL-2 as PMN stimulators. Inhibition of TLR-4 signaling with TAK-242 diminished PMN killing. The efficacy was stronger with the somewhat weaker stimulatory signal via DAMPs. With IL-2, PMN killing was still markedly reduced.

Figure 14:
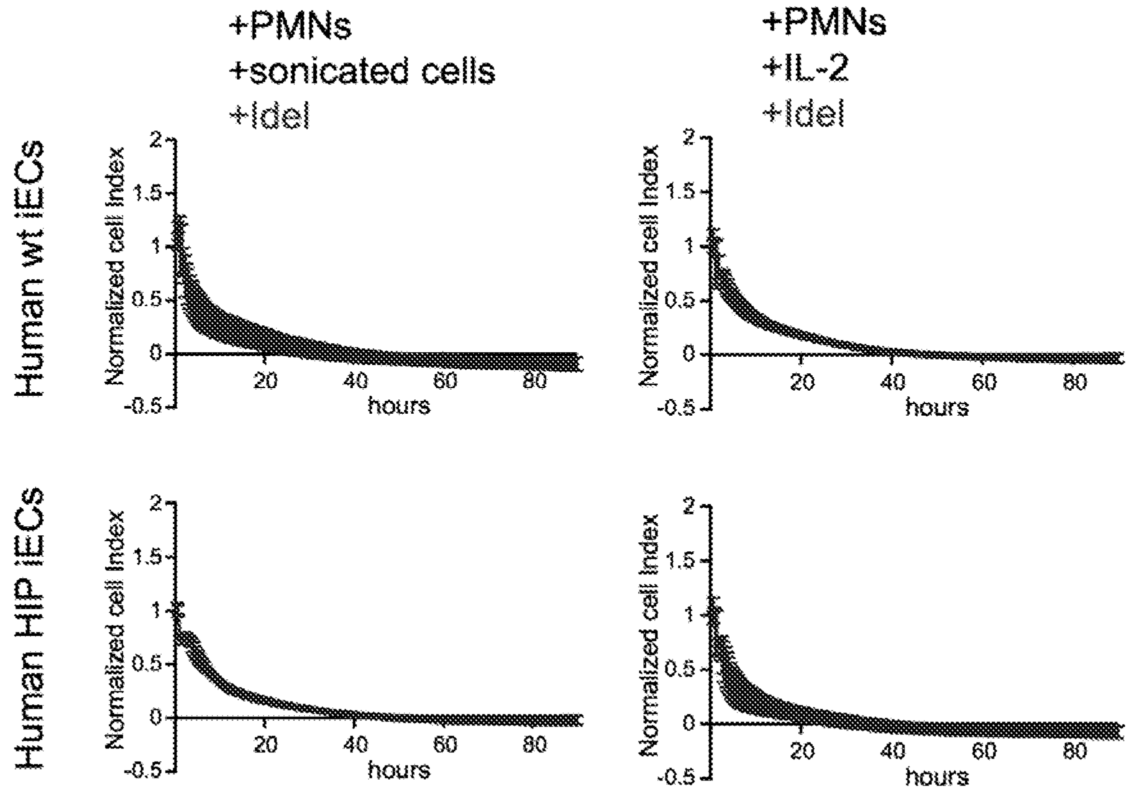

FIG. 14: PMN inhibition via TLR-4 signaling was assessed using Idelalisib, a downstream inhibitor. Inhibition of TLR-4 signaling with Idelalisib mildly diminished PMN killing.

Figure 15:
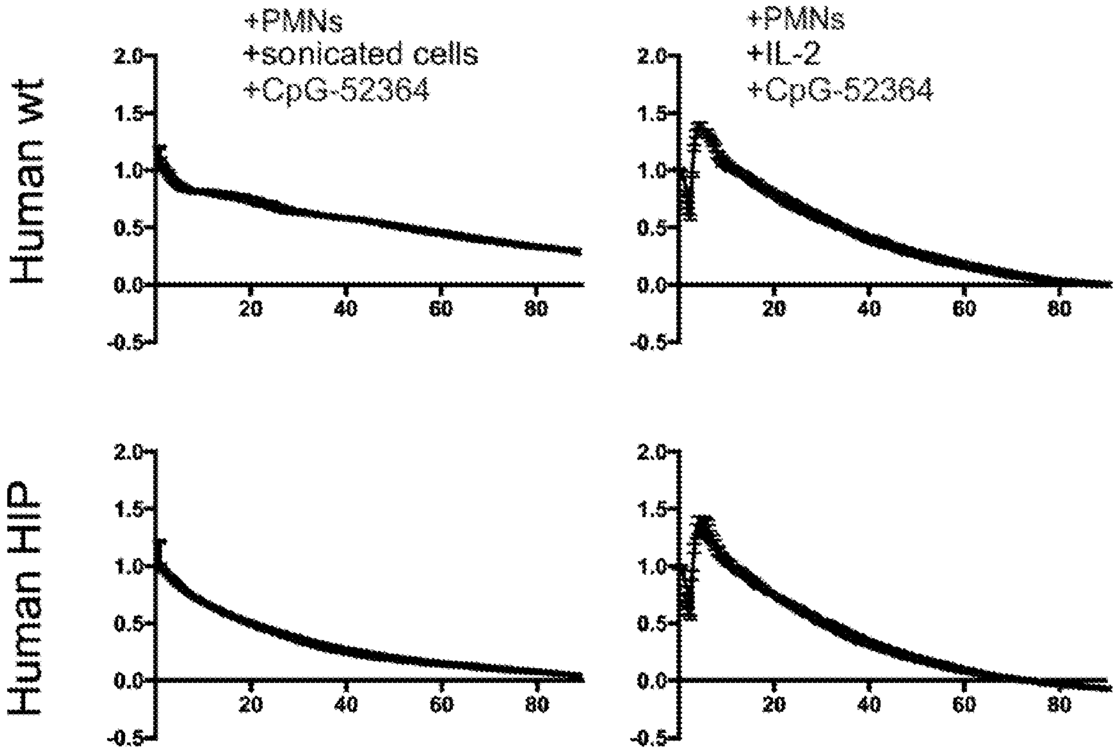

FIG. 15: Inhibition of TLR7/8/9 signaling was tested using the oligonucleotide CpG-52364. Wt and HIP iECs were used in XCelligence PMN assays using necrotic cells or IL-2 as stimulators. Inhibition of TLR-7/8/9 signaling with CpG-52364 also reduced PMN killing. CpG-52364 was more effective when sonicated cells were used as stimulators compared to IL-2.

Figure 16:
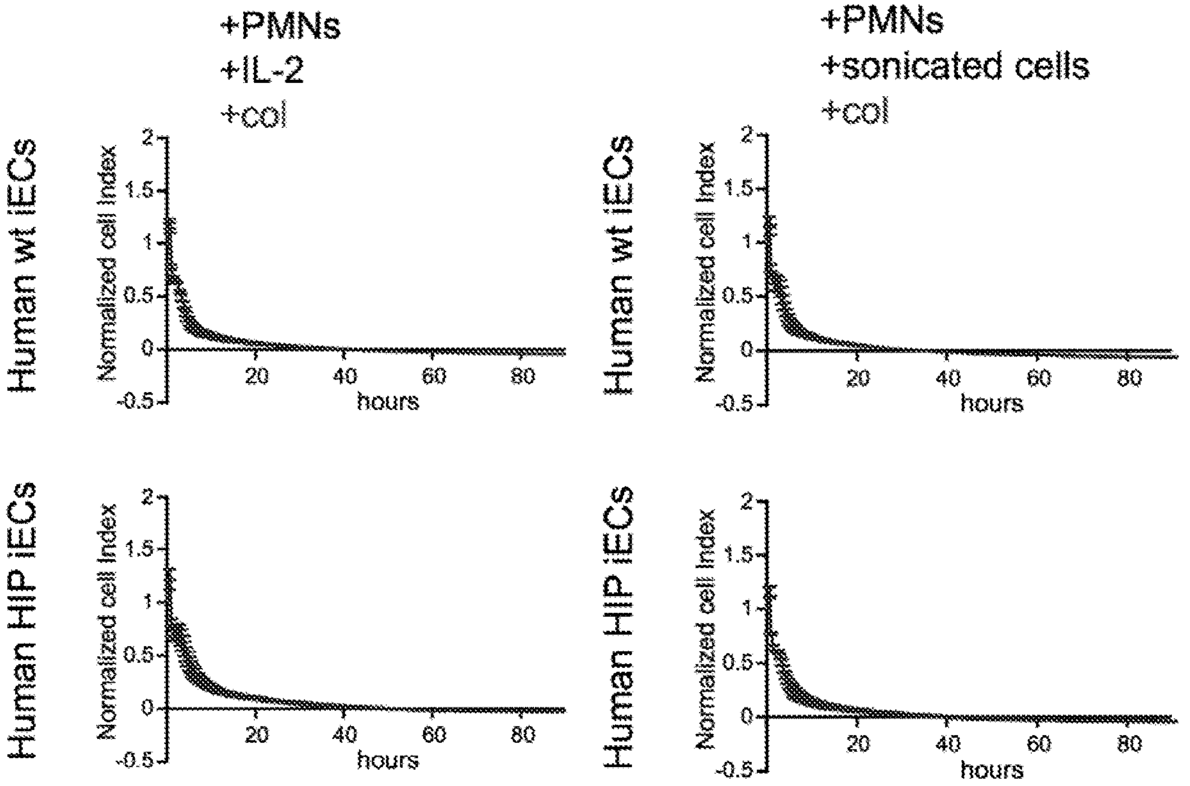

FIG. 16: Colchicine (col) was used here as another strategy to inhibit PMN killing as a monotherapy. In Xcelligence assays with DAMP or IL-2 activated PMNs, the monotherapy of colchicine showed only marginal efficacy.

Figure 17:
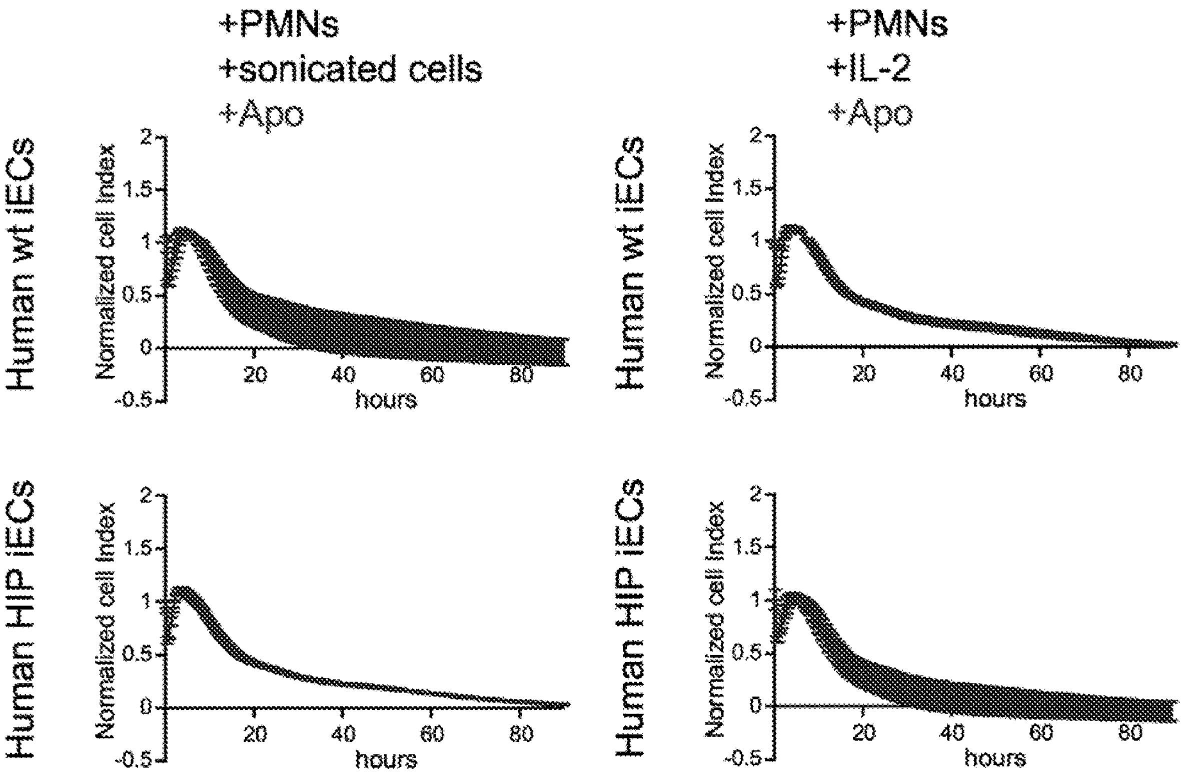

FIG. 17: Apocynin (Apo) diminished DAMP- or IL-2 activated PMN killing. Apocynin reduced PMN killing for wt and HIP iEC target cells FIG. 18A: Combination regimens were used to increase the overall efficacy of PMN inhibition. PMN XCelligence assays were run with combinations of colchicine (col), BAY 85-8501, or TAK-242. DAMPs were used to activate PMNs. All combinations were very effective to completely inhibit PMN killing.

Figure 18A:
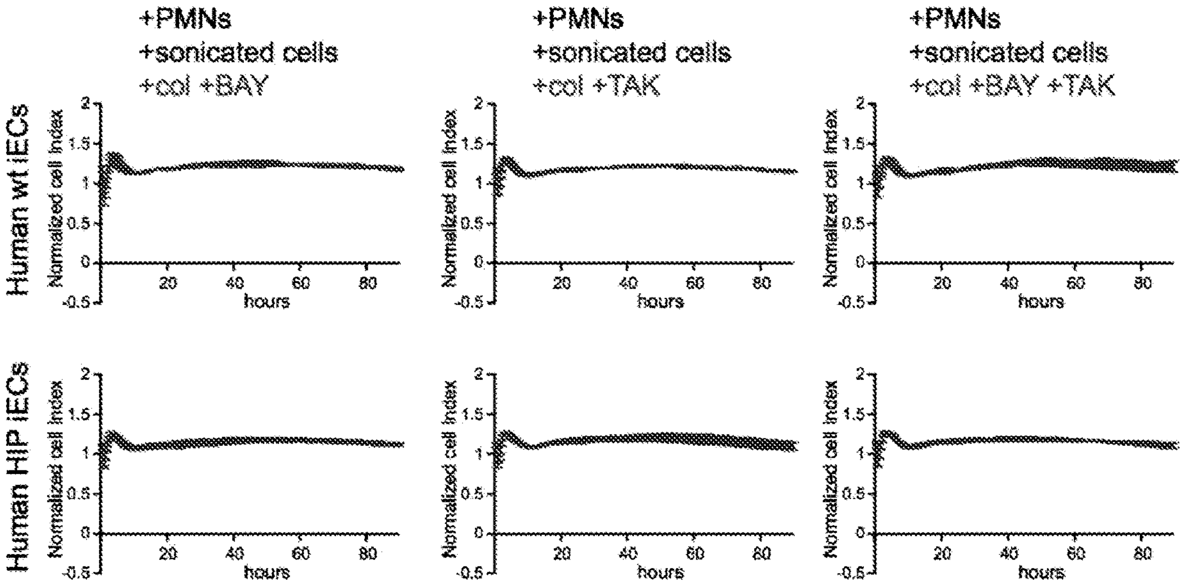
Figure 18B:
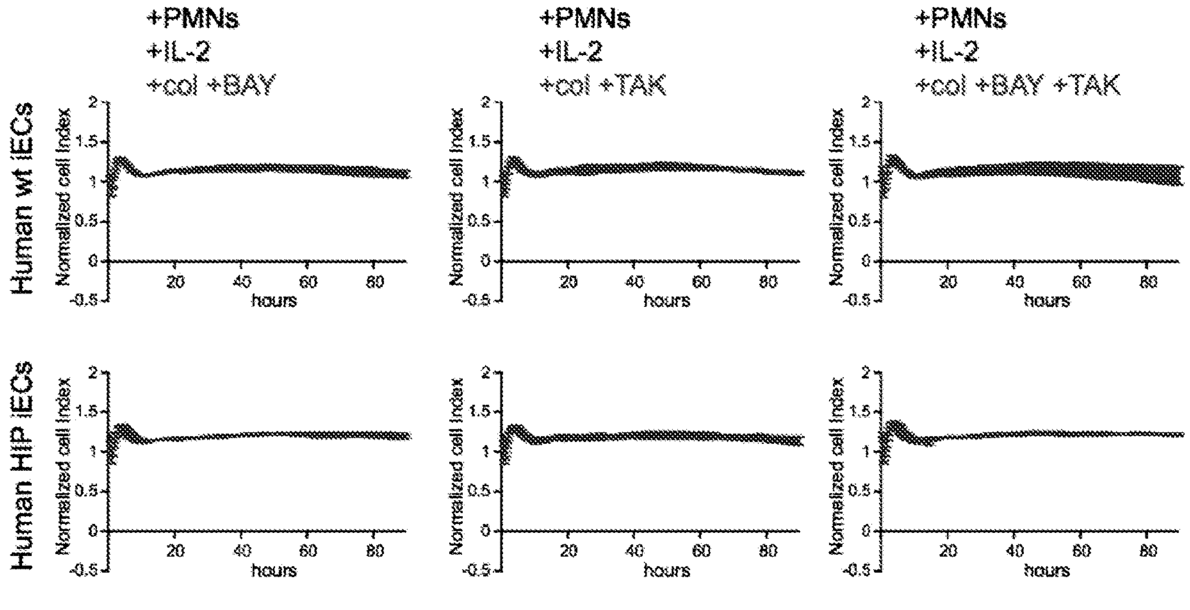

FIG. 18B: Combination regimens were used to increase the overall efficacy of PMN inhibition. PMN XCelligence assays were run with combinations of colchicine (col), BAY 85-8501, or TAK-242. IL-2 was used to activate PMNs. All combinations were very effective to completely inhibit PMN killing.

Figure 19:
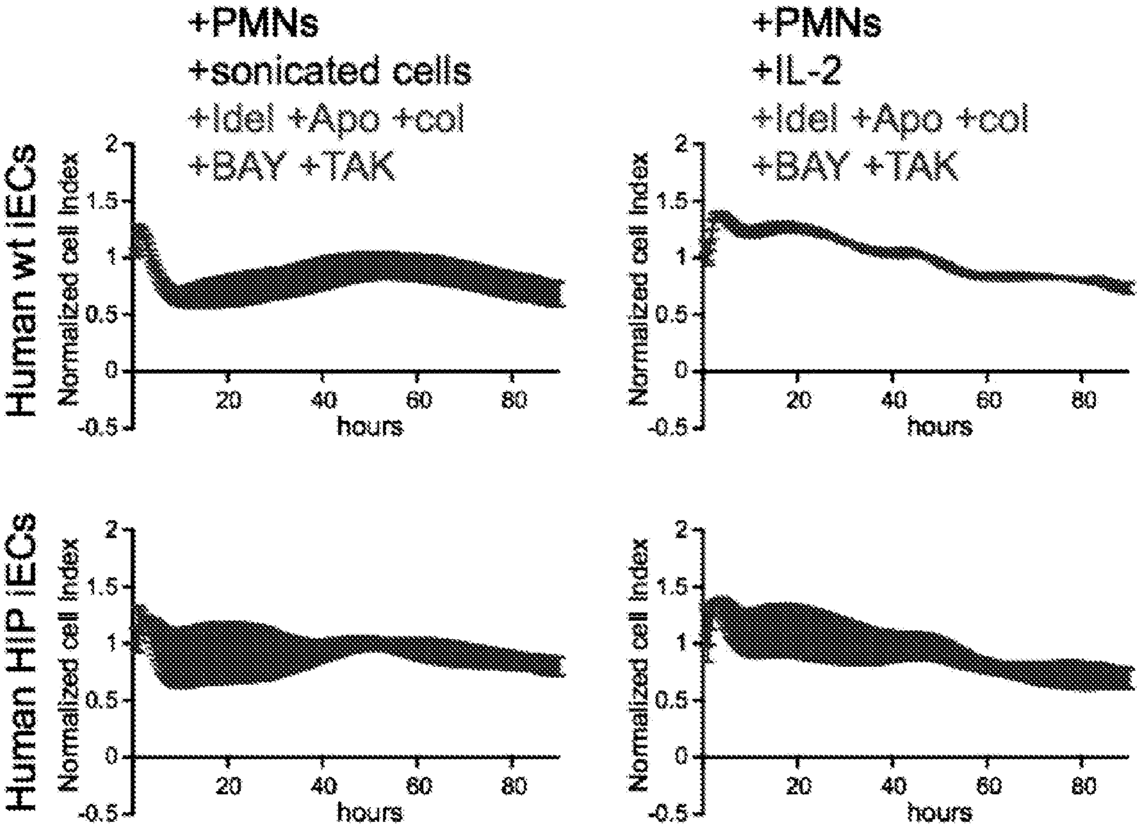

FIG. 19: PMN XCelligence assays were run with a combination of Idelalisib (Idel), Apocynin (Apo), colchicine (col), BAY 85-8501, and TAK-242. DAMPs or IL-2 was used to activate PMNs. This combination was very effective to completely inhibit PMN killing.

Figure 20A:
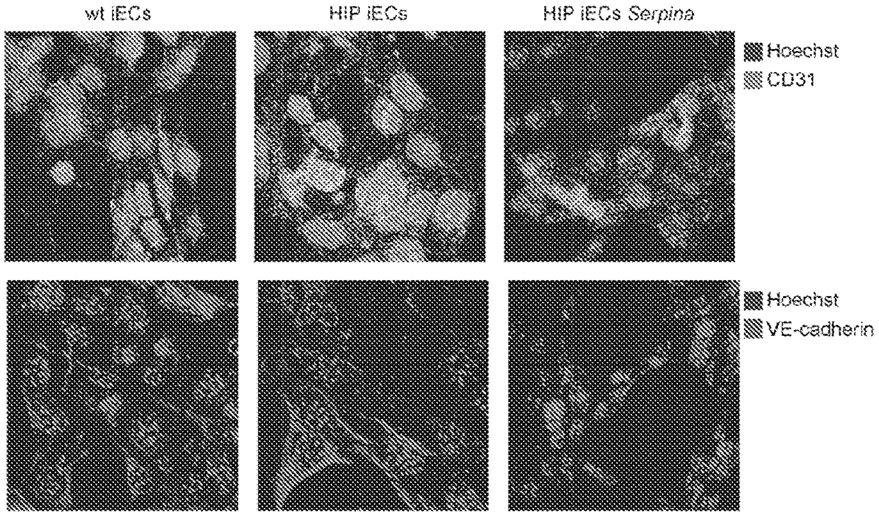

FIG. 20A: A1AT-releasing $HIP_{Serpine1}$ iECs. HIP iECs engineered to make A1AT ($HIP_{Serpine1}$ iECs) were grown in culture and shared typical endothelial cell features with their parental wt iECs and HIP iECs (representative pictures of two independent experiments).

Figure 20B:
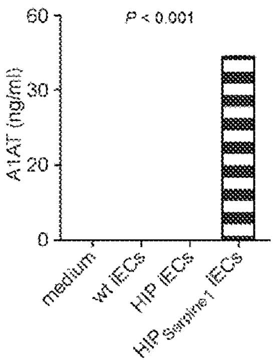

FIG. 20B: A1AT-releasing $HIP_{Serpine1}$ iECs. A total of $1.5\times10^5$ wt, HIP, and $HIP_{Serpine1}$ iECs were cultured for 24 h in endothelial cell medium. The A1AT concentration was then assessed by Elisa (mean±s.d., three independent experiments, analysis of variance (ANOVA)).

Figure 21A:
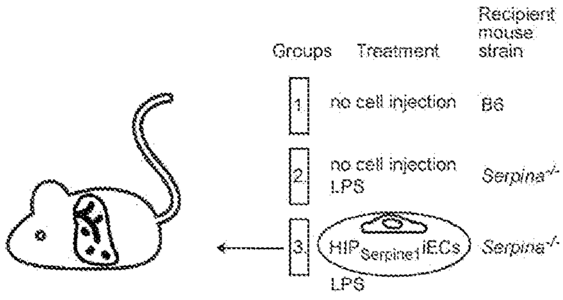

FIG. 21A: Study design for A1AT-releasing $HIP_{Serpine1}$ iEC therapy. $Serpina^{-/-}$ mice were challenged with LPS via their airways to trigger emphysematous lung disease. Healthy B6 animals served as controls. The study protocol included morphologic as well as functional lung assessment after 28 days.

Figure 21B:
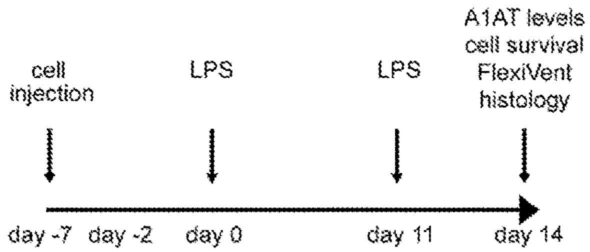

FIG. 21B: Study design for A1AT-releasing $HIP_{Serpine1}$ iEC therapy. Group 3 animals were treated with $HIP_{Serpine1}$ iECs 7 days before the LPS challenge FIG. 22: Serum A1AT levels. On day 21 after $HIP_{Serpine1}$ iEC transplantation (14 days after the first LPS challenge), serum A1AT levels were quantified in all groups (mean±s.d., 6 animals in B6, 5 animals in $Serpina^{-/-}$ LPS, 6 animals in $Serpina^{-/-}$ LPS $HIP_{Serpine1}$ iEC group, analysis of variance (ANOVA)).

Figure 23:
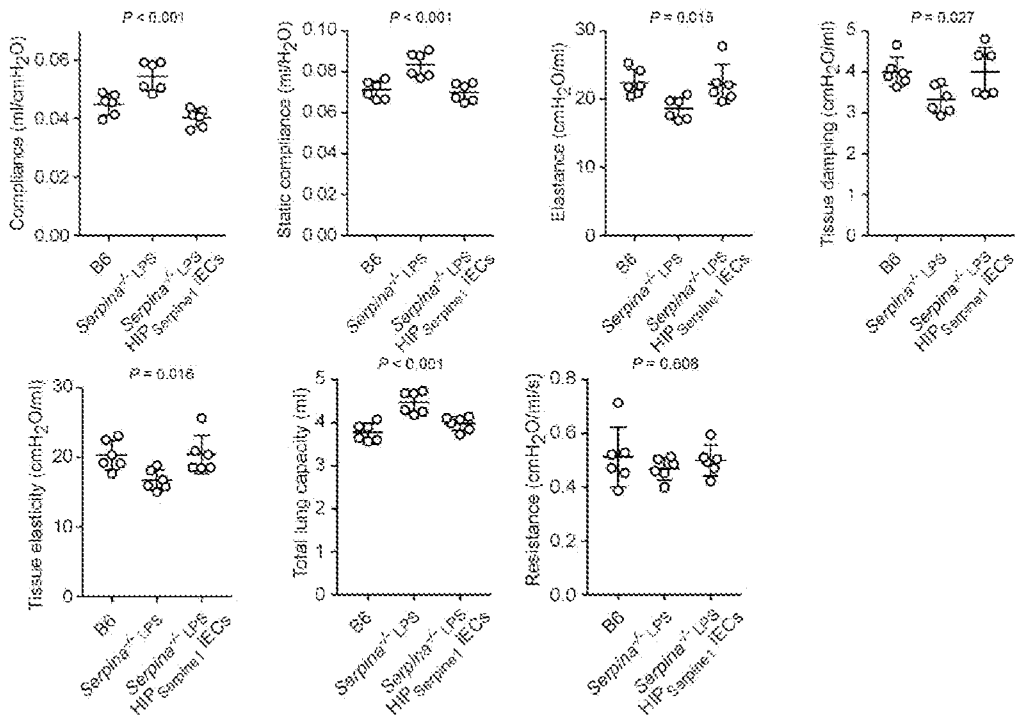

FIG. 23: Assessment of pulmonary mechanics. FlexiVent lung physiology assessments were done after 28 days (scatter dot plots, mean±s.d., 6 animals per group, analysis of variance (ANOVA)). Untreated $Serpina^{-/-}$ mice developed ventilation patterns consistent with developing emphysema. $HIP_{Serpine1}$ iEC therapy was effective in preventing the development of respiratory patterns typical of emphysematous lung disease in $Serpina^{-/-}$ mice.

Figure 24:
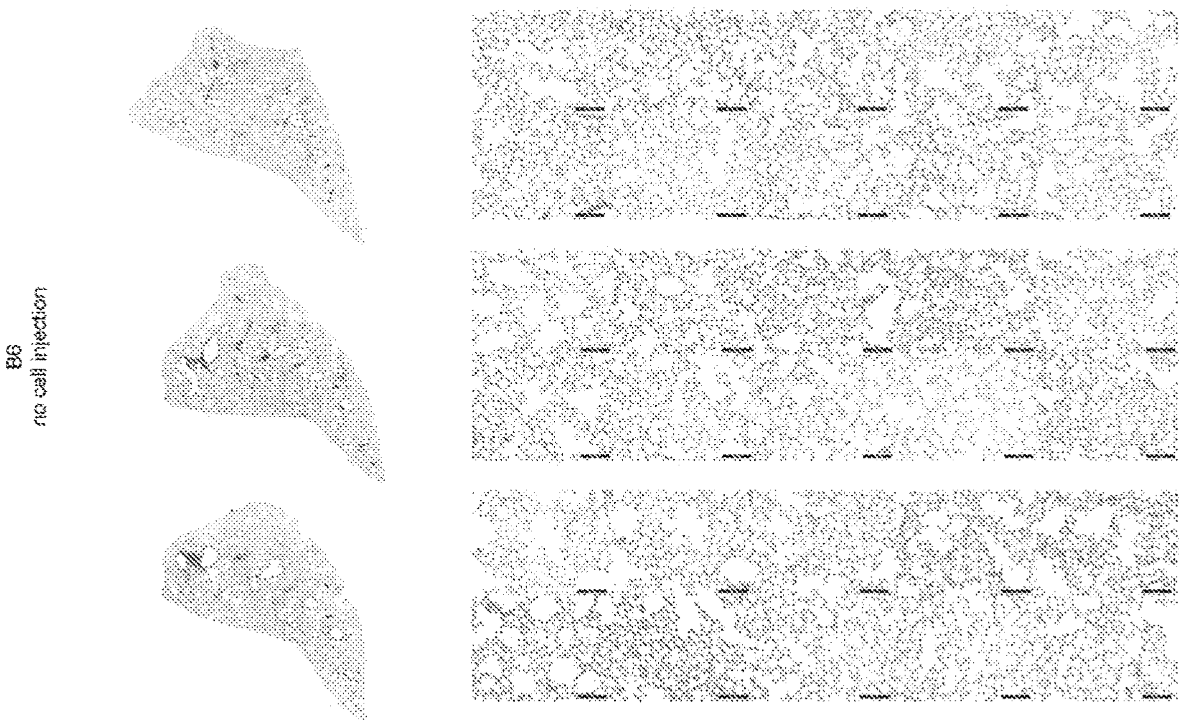

FIG. 24: Assessment of airspace characteristics in healthy mouse lungs. Lungs of healthy B6 mice were sectioned, stained, and underwent stereological assessment (representative pictures of 6 animals).

Figure 25:
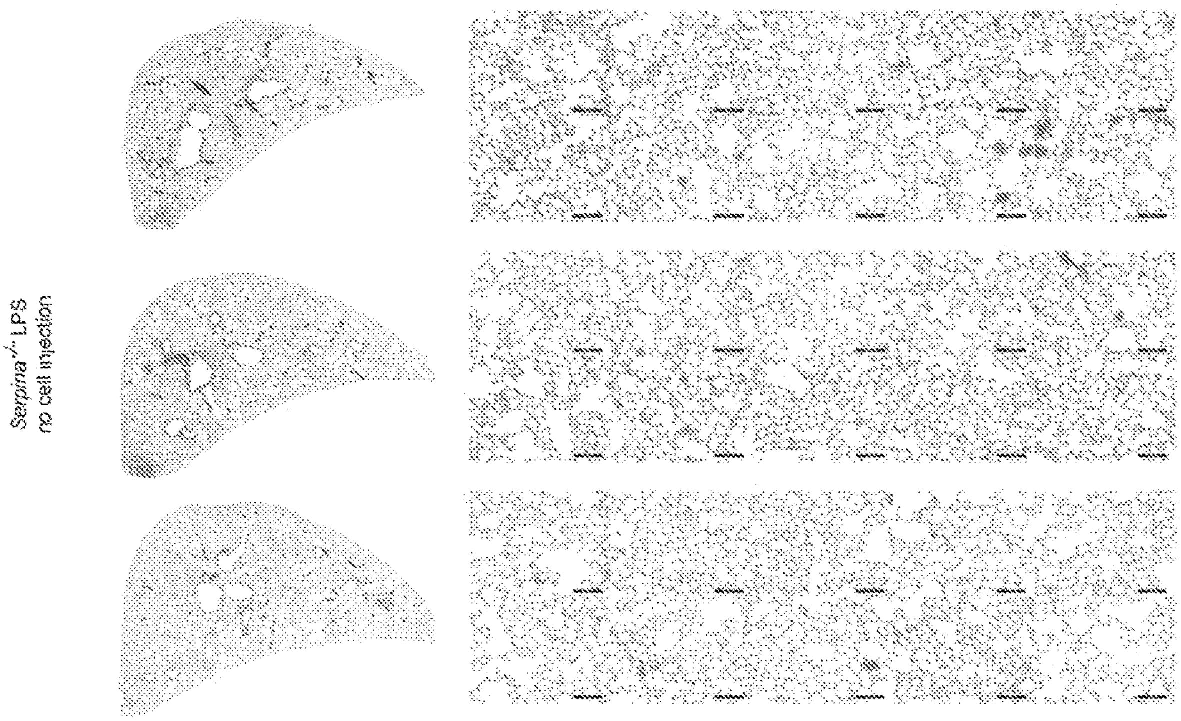

FIG. 25: Assessment of airspace characteristics in $Serpina^{-/-}$ mice. $Serpina^{-/-}$ mice were exposed to a mild LPS airways challenge and developed features of emphysema (representative pictures of six animals).

Figure 26:
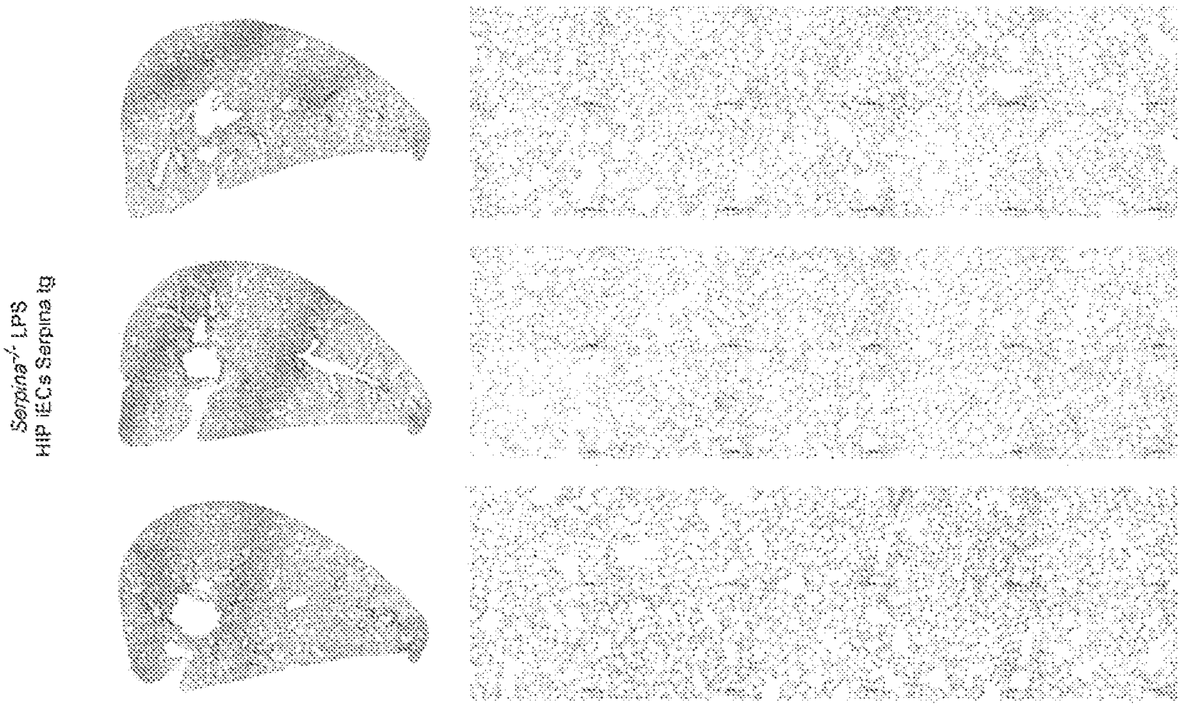

FIG. 26: Assessment of airspace characteristics in treated Serpina$^{-/-}$ mice. Serpina$^{-/-}$ mice received $1.5\times10^8$ HIP$_{Serpine1}$ iECs 7 days before the first LPS challenge (representative pictures of 6 animals).

Figure 27:
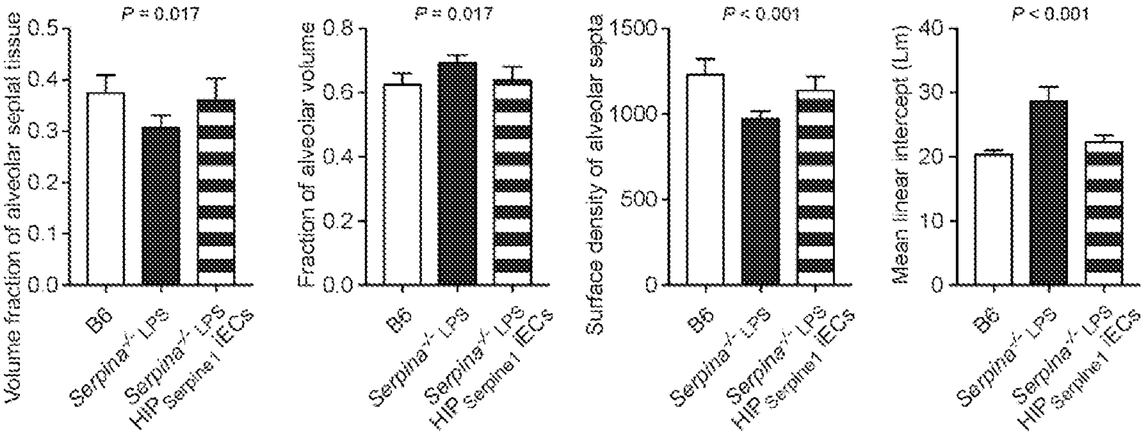

FIG. 27: Stereological lung assessment. Histology slides were scanned and assessed in a standardized way. Stereological lung assessment (mean±s.d., six animals per group, analysis of variance (ANOVA)). Morphometric criteria for emphysema in untreated Serpina$^{-/-}$ mice including distal airspace enlargement, loss of alveoli and alveolar surface area, and increase in mean linear intercept (chord) length, a parameter to describe the mean free distance in the air spaces were found. HIP$_{Serpine1}$ iEC therapy was successful in preventing all structural damages to the lung tissue.

Figure 28:
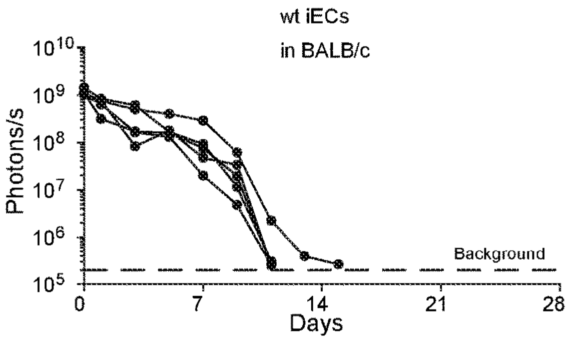

FIG. 28: Allogeneic BALB/c recipients were used to separately assess graft survival. Wild type B6 iECs did not survive allogeneic transplantation into BALB/c mice beyond 14 days. In contrast HIP$_{Serpine1}$ iEC from B6 mice survived allogenic transplantation in BALB/c mice for at least 28 days.

Figure 29:
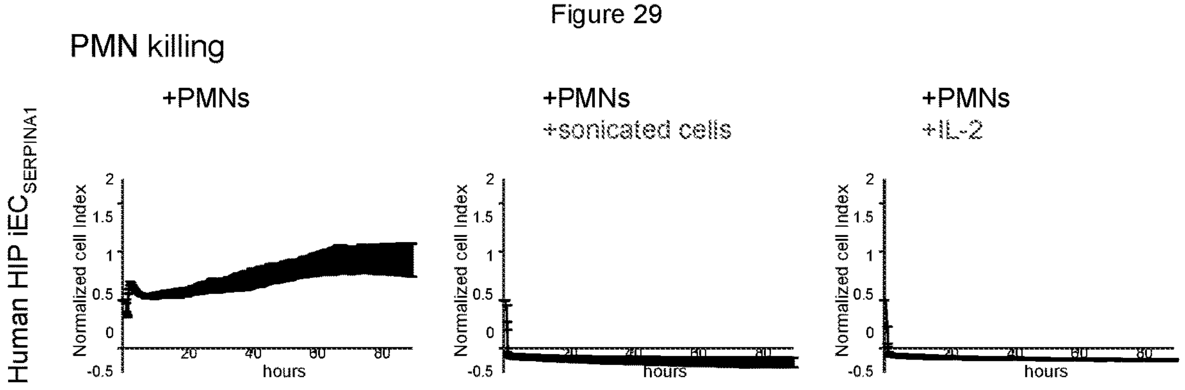

FIG. 29: Human HIP iEC$_{SERPINA1}$ target cells on the XCelligence platform were not killed by human PMNs. Both sonicated target cells and IL-2, however, led to PMN activation and target HIP iEC$_{SERPINA1}$ killing.

Figure 30:
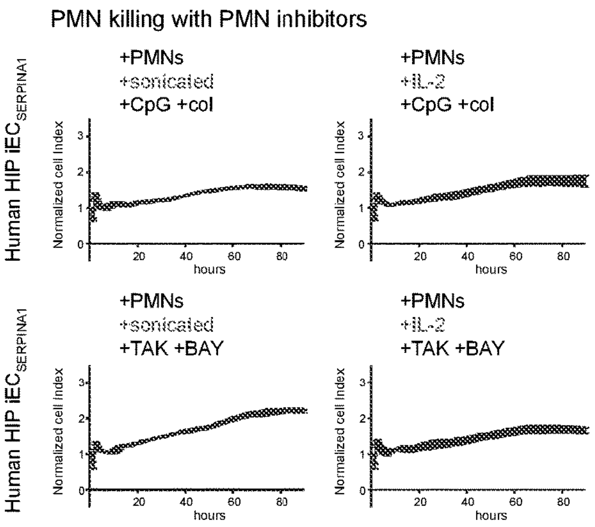

FIG. 30: Human HIP iEC$_{SERPINA1}$ target cells on the XCelligence platform were challenged with PMNs activated via sonicated target cells (left column) or IL-2 (right column). The HIP iEC$_{SERPINA1}$ target cells were not killed when two PMN inhibitory regimens were used: CpG-52364+ colchicine (upper row) and TAK-242+BAY 85-8501.

Figure 31:
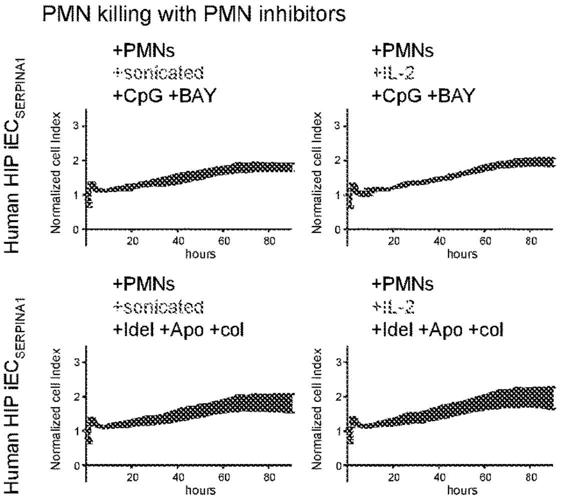

FIG. 31: Human HIP iEC$_{SERPINA1}$ target cells on the XCelligence platform were challenged with PMNs activated via sonicated target cells (left column) or IL-2 (right column). The HIP iEC$_{SERPINA1}$ target cells were also not killed when two other PMN inhibitory regimens were used: CpG-52364+BAY 85-8501 (upper row) and Idelalisib+Apocynin+colchicine.

VI. DETAILED DESCRIPTION OF THE INVENTION

A. Introduction

The invention identifies PMNs as an additional immune barrier for the survival of cell transplantation. Non-specific DAMPs released by necrotic cells can induce PMN activation and lead to the killing of healthy bystander cells as collateral damage in an attempt to contain and clear infection or injury. This killing is independent of hypoimmune (e.g. HIP) cell gene editing and relates to the cell transplant period prior to when the cells have integrated and engrafted into the host tissue. Non-stimulated PMNs show no tendency to kill healthy allogeneic target cells.

The invention provides, for the first time, regenerative cell therapies having a reduced sensitivity to the cell transplant recipient's innate immune system that kills the cells during the window of time shortly after transplantation. In some embodiments, the invention blocks PMN cell killing induced by cytokines, chemokines, danger-associated molecular patterns (DAMPs, FIG. 1), or pathogen-associated molecular patterns (PAMPs).

A summary of the PMN inhibitory strategies is shown at FIG. 2. In some embodiments, PMNs are inhibited by targeting the CD200 Receptor (CD200R), PIRLa, SIRL-1, Neutrophil Elastase (NE), IL-2R, TLR4, TLR7, TLR8, TLR9, microtubule polymerization, or superoxide release. In other embodiments, transplanted cells such as hypoimmune pluripotent cells (HIP), or derivatives thereof, that express increased CD200 or CD99.

Neutrophil Elastase is a serine proteinase in the same family as chymotrypsin and has broad substrate specificity. Secreted by neutrophils and macrophages during inflammation, it destroys bacteria and host tissue. It also localizes to Neutrophil extracellular traps (NETs) via its high affinity for DNA, an unusual property for serine proteases.

The invention provides effective regimens to dampen or even fully prevent PMN killing of human target cells. PMN activation and response is complex and multi-layered. While single drugs were effective, combinations of drugs were more likely to completely inhibit PMN killing. In some embodiments, the drug combinations are synergistic. Exemplary embodiments include:

- TAK-242 and CpG-52364 are very effective to dampen PMN activation, likely via parenteral application.
- Idelalisib and apocynin are available for oral application and is effective to dampen PMN activation.
- Colchicine is available for oral application, acts via a mechanism distinct of all other drugs, and ample human data are available.
- BAY 85-8501 is available for oral application and shows high selectivity and efficacy for the inhibition of PMN killing.
- NI-0101 is available for parenteral application and is effective to dampen PMN activation.
- Cyclosporine A is a calcineurin inhibitor like the more commonly used tacrolimus and both will be able to reduce IL-2, a very strong stimulator of PMN activation.

The inhibitory PMN strategies provided herein may only be necessary during the cell transplant and engraftment period when strong activating PMN signals are present and no further treatment is necessary for maintaining hypoimmune cells or their derivatives. Where permanent PMN inhibition is desired, the invention provides modified cells with increased CD200 or CD99 surface expression or cells made to release Alpha1 Antitrypsin.

In some embodiments of the invention, HypoImmunogenic Pluripotent ("HIP") cells, or derivatives thereof, are transplanted in combination with PMN cell-inhibitory strategy. HIP cells avoid host immune responses due to several genetic manipulations. The cells lack major immune antigens that trigger immune responses and are engineered to avoid phagocytosis and NK cell killing. In some embodiments, the HIP cells are made by eliminating the activity of both alleles of a B2M gene in an induced pluripotent stem cell (iPSC); eliminating the activity of both alleles of a CIITA gene in the iPSC; and increasing the expression of CD47 in the iPSC. HIP cells are described in detail in WO2018132783, incorporated by reference herein in its entirety.

In some embodiments of the invention, HypoImmunogenic Pluripotent Blood group O Rh− ("HIPO−") cells, or derivatives thereof, are transplanted in combination with a PMN cell-inhibitory strategy. HIPO− cells avoid host immune responses due to several genetic or enzymatic manipulations. The cells lack major blood group and immune antigens that trigger immune responses and are engineered to avoid rejection, phagocytosis, or killing. This allows the derivation of "off-the-shelf" cell products for generating specific tissues and organs. The benefit of being able to use human allogeneic HIPO− cells and their derivatives in human patients provides significant benefits, including the ability to avoid long-term adjunct immunosuppressive therapy and drug use generally seen in allogeneic transplantations. They also provide significant cost savings as cell therapies can be used without requiring individual treatments for each patient.

HIPO−/CD16, HIPO−/CD32, or HIPO−/CD64 cells may serve as a universal cell source for the generation of universally-acceptable derivatives. HIPO− cells are described in detail in U.S. Prov. Appl. Nos. 62/846,399 and 62/855,499. Transplanted cells that comprise enhanced CD16, CD32, or CD64 expression to evade ADCC or CDC are described in 62/915,601. The foregoing are incorporated by reference herein in their entirety.

In some embodiments, the transplanted cells comprise enhanced CD16, CD32, or CD64 expression to evade antibody-dependent cellular cytotoxicity (ADCC) or complement-dependent cytotoxicity (CDC). Such cells are described in detail in U.S. Prov. Appl. No. 62/915,601, incorporated by reference herein in its entirety.

B. Definitions

The term "pluripotent cells" refers to cells that can self-renew and proliferate while remaining in an undifferentiated state and that can, under the proper conditions, be induced to differentiate into specialized cell types. The term "pluripotent cells," as used herein, encompass embryonic stem cells and other types of stem cells, including fetal, amnionic, or somatic stem cells. Exemplary human stem cell lines include the H9 human embryonic stem cell line. Additional exemplary stem cell lines include those made available through the National Institutes of Health Human Embryonic Stem Cell Registry and the Howard Hughes Medical Institute HUES collection (as described in Cowan, C. A. et. al, *New England J. Med.* 350:13. (2004), incorporated by reference herein in its entirety.)

"Pluripotent stem cells" as used herein have the potential to differentiate into any of the three germ layers: endoderm (e.g. the stomach linking, gastrointestinal tract, lungs, etc), mesoderm (e.g. muscle, bone, blood, urogenital tissue, etc) or ectoderm (e.g. epidermal tissues and nervous system tissues). The term "pluripotent stem cells," as used herein, also encompasses "induced pluripotent stem cells", or "iPSCs", a type of pluripotent stem cell derived from a non-pluripotent cell. Examples of parent cells include somatic cells that have been reprogrammed to induce a pluripotent, undifferentiated phenotype by various means. Such "iPS" or "iPSC" cells can be created by inducing the expression of certain regulatory genes or by the exogenous application of certain proteins. Methods for the induction of iPS cells are known in the art and are further described below. (See, e.g., Zhou et al., *Stem Cells* 27 (11): 2667-74 (2009); Huangfu et al., *Nature Biotechnol.* 26 (7): 795 (2008); Woltjen et al., *Nature* 458 (7239): 766-770 (2009); and Zhou et al., *Cell Stem Cell* 8:381-384 (2009); each of which is incorporated by reference herein in their entirety.) The generation of induced pluripotent stem cells (iPSCs) is outlined below. As used herein, "hiPSCs" are human induced pluripotent stem cells, and "miPSCs" are murine induced pluripotent stem cells.

"Pluripotent stem cell characteristics" refer to characteristics of a cell that distinguish pluripotent stem cells from other cells. The ability to give rise to progeny that can undergo differentiation, under the appropriate conditions, into cell types that collectively demonstrate characteristics associated with cell lineages from all of the three germinal layers (endoderm, mesoderm, and ectoderm) is a pluripotent stem cell characteristic. Expression or non-expression of certain combinations of molecular markers are also pluripotent stem cell characteristics. For example, human pluripotent stem cells express at least several, and in some embodiments, all of the markers from the following non-limiting list: SSEA-3, SSEA-4, TRA-1-60, TRA-1-81, TRA-2-49/6E, ALP, Sox2, E-cadherin, UTF-1, Oct4, Rex1, and Nanog. Cell morphologies associated with pluripotent stem cells are also pluripotent stem cell characteristics. As described herein, cells do not need to pass through pluripotency to be reprogrammed into endodermal progenitor cells and/or hepatocytes.

As used herein, "multipotent" or "multipotent cell" refers to a cell type that can give rise to a limited number of other particular cell types. For example, induced multipotent cells are capable of forming endodermal cells. Additionally, multipotent blood stem cells can differentiate itself into several types of blood cells, including lymphocytes, monocytes, neutrophils, etc.

As used herein, the term "oligopotent" refers to the ability of an adult stem cell to differentiate into only a few different cell types. For example, lymphoid or myeloid stem cells are capable of forming cells of either the lymphoid or myeloid lineages, respectively.

As used herein, the term "unipotent" means the ability of a cell to form a single cell type. For example, spermatogonial stem cells are only capable of forming sperm cells.

As used herein, the term "totipotent" means the ability of a cell to form an entire organism. For example, in mammals, only the zygote and the first cleavage stage blastomeres are totipotent.

As used herein, "non-pluripotent cells" refer to mammalian cells that are not pluripotent cells. Examples of such cells include differentiated cells as well as progenitor cells. Examples of differentiated cells include, but are not limited to, cells from a tissue selected from bone marrow, skin, skeletal muscle, fat tissue and peripheral blood. Exemplary cell types include, but are not limited to, fibroblasts, hepatocytes, myoblasts, neurons, osteoblasts, osteoclasts, and T-cells. The starting cells employed for generating the induced multipotent cells, the endodermal progenitor cells, and the hepatocytes can be non-pluripotent cells.

Differentiated cells include, but are not limited to, multipotent cells, oligopotent cells, unipotent cells, progenitor cells, and terminally differentiated cells. In particular embodiments, a less potent cell is considered "differentiated" in reference to a more potent cell.

A "somatic cell" is a cell forming the body of an organism. Somatic cells include cells making up organs, skin, blood, bones and connective tissue in an organism, but not germ cells.

Cells can be from, for example, human or non-human mammals. Exemplary non-human mammals include, but are not limited to, mice, rats, cats, dogs, rabbits, guinea pigs, hamsters, sheep, pigs, horses, bovines, and non-human primates. In some embodiments, a cell is from an adult human or non-human mammal. In some embodiments, a cell is from a neonatal human, an adult human, or non-human mammal.

As used herein, the terms "subject" or "patient" refers to any animal, such as a domesticated animal, a zoo animal, or a human. The "subject" or "patient" can be a mammal like a dog, cat, bird, livestock, or a human. Specific examples of "subjects" and "patients" include, but are not limited to, individuals (particularly human) with a disease or disorder related to the liver, heart, lung, kidney, pancreas, brain, neural tissue, blood, bone, bone marrow, and the like.

Mammalian cells can be from humans or non-human mammals. Exemplary non-human mammals include, but are not limited to, mice, rats, cats, dogs, rabbits, guinea pigs, hamsters, sheep, pigs, horses, bovines, and non-human primates (e.g., chimpanzees, macaques, and apes).

By "hypo-immunogenic pluripotent" cell or "HIP" cell herein is meant a pluripotent cell that retains its pluripotent characteristics and yet gives rise to a reduced immunological rejection response when transferred into an allogeneic host. In preferred embodiments, HIP cells do not give rise to an immune response. Thus, "hypo-immunogenic" refers to a significantly reduced or eliminated immune response when compared to the immune response of a parental (i.e. "wt") cell prior to immunoengineering as outlined herein. In many cases, the HIP cells are immunologically silent and yet retain pluripotent capabilities. Assays for HIP characteristics are outlined below.

By "HIP/CD16", "HIP/CD32", or "HIP/CD64" cell herein is meant a HIP cell that has enhanced CD16, CD32, or CD64 expression, respectively.

By "hypo-immunogenic pluripotent cell O−" "hypo-immunogenic pluripotent ORh−" cell or "HIPO−" cell herein is meant a HIP cell that is also ABO blood group O and Rhesus Factor Rh−. HIPO− cells may have been generated from O− cells, enzymatically modified to be O−, or genetically engineered to be O−.

By "HIPO−/CD16", "HIPO−/CD32", or "HIPO−/CD64" cell herein is meant a HIPO− cell that has enhanced CD16, CD32, or CD64 expression.

By "HLA" or "human leukocyte antigen" complex is a gene complex encoding the major histocompatibility complex (MHC) proteins in humans. These cell-surface proteins that make up the HLA complex are responsible for the regulation of the immune response to antigens. In humans, there are two MHCs, class I and class II, "HLA-I" and "HLA-II". HLA-I includes three proteins, HLA-A, HLA-B and HLA-C, which present peptides from the inside of the cell, and antigens presented by the HLA-I complex attract killer T-cells (also known as CD8+ T-cells or cytotoxic T cells). The HLA-I proteins are associated with β-2 microglobulin (B2M). HLA-II includes five proteins, HLA-DP, HLA-DM, HLA-DOB, HLA-DQ and HLA-DR, which present antigens from outside the cell to T lymphocytes. This stimulates CD4+ cells (also known as T-helper cells). It should be understood that the use of either "MHC" or "HLA" is not meant to be limiting, as it depends on whether the genes are from humans (HLA) or murine (MHC). Thus, as it relates to mammalian cells, these terms may be used interchangeably herein.

By "gene knock out" herein is meant a process that renders a particular gene inactive in the host cell in which it resides, resulting either in no protein of interest being produced or an inactive form. As will be appreciated by those in the art and further described below, this can be accomplished in a number of different ways, including removing nucleic acid sequences from a gene, or interrupting the sequence with other sequences, altering the reading frame, or altering the regulatory components of the nucleic acid. For example, all or part of a coding region of the gene of interest can be removed or replaced with "nonsense" sequences, all or part of a regulatory sequence such as a promoter can be removed or replaced, translation initiation sequences can be removed or replaced, etc.

By "gene knock in" herein is meant a process that adds a genetic function to a host cell. This causes increased levels of the encoded protein. As will be appreciated by those in the art, this can be accomplished in several ways, including adding one or more additional copies of the gene to the host cell or altering a regulatory component of the endogenous gene increasing expression of the protein is made. This may be accomplished by modifying the promoter, adding a different promoter, adding an enhancer, or modifying other gene expression sequences.

"β-2 microglobulin" or "β2M" or "B2M" protein refers to the human β2M protein that has the amino acid and nucleic acid sequences shown below; the human gene has accession number NC_000015.10:44711487-44718159.

"CD47 protein" protein refers to the human CD47 protein that has the amino acid and nucleic acid sequences shown below; the human gene has accession number NC_000016.10:10866208-10941562.

"CIITA protein" protein refers to the human CIITA protein that has the amino acid and nucleic acid sequences shown below; the human gene has accession number NC_000003.12:108043094-108094200.

By "wild type" in the context of a cell means a cell found in nature. However, in the context of a pluripotent stem cell, as used herein, it also means an iPSC that may contain nucleic acid changes resulting in pluripotency but did not undergo the gene editing procedures of the invention to achieve hypo-immunogenicity.

By "syngeneic" herein refers to the genetic similarity or identity of a host organism and a cellular transplant where there is immunological compatibility; e.g. no immune response is generated.

By "allogeneic" herein refers to the genetic dissimilarity of a host organism and a cellular transplant where an immune response is generated.

By "B2M−/−" herein is meant that a diploid cell has had the B2M gene inactivated in both chromosomes. As described herein, this can be done in a variety of ways.

By "CIITA −/−" herein is meant that a diploid cell has had the CIITA gene inactivated in both chromosomes. As described herein, this can be done in a variety of ways.

By "CD47 tg" (standing for "transgene") or "CD47+") herein is meant that the host cell expresses CD47, in some cases by having at least one additional copy of the CD47 gene.

An "Oct polypeptide" refers to any of the naturally-occurring members of Octamer family of transcription factors, or variants thereof that maintain transcription factor activity, similar (within at least 50%, 80%, or 90% activity) compared to the closest related naturally occurring family member, or polypeptides comprising at least the DNA-binding domain of the naturally occurring family member, and can further comprise a transcriptional activation domain. Exemplary Oct polypeptides include Oct-1, Oct-2, Oct-3/4, Oct-6, Oct-7, Oct-8, Oct-9, and Oct-11. Oct3/4 (referred to herein as "Oct4") contains the POU domain, a 150 amino acid sequence conserved among Pit-1, Oct-1, Oct-2, and uric-86. (See, Ryan, A. K. & Rosenfeld, M. G., Genes Dev. 11:1207-1225 (1997), incorporated herein by reference in its entirety.) In some embodiments, variants have at least 85%, 90%, or 95% amino acid sequence identity across their whole sequence compared to a naturally occurring Oct polypeptide family member such as to those listed above or such as listed in Genbank accession number NP-002692.2 (human Oct4) or NP-038661.1 (mouse Oct4). Oct polypeptides (e.g., Oct3/4 or Oct 4) can be from human, mouse, rat, bovine, porcine, or other animals. Generally, the same species of protein will be used with the species of cells being manipulated. The Oct polypeptide(s) can be a pluripotency factor that can help induce multipotency in non-pluripotent cells.

A "Klf polypeptide" refers to any of the naturally-occurring members of the family of Krüppel-like factors (Klfs), zinc-finger proteins that contain amino acid sequences similar to those of the *Drosophila* embryonic pattern regulator Krüppel, or variants of the naturally-occurring members that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. (See, Dang, D. T., Pevsner, J. & Yang, V. W., Cell Biol. 32:1103-1121 (2000), incorporated by reference herein in its entirety.) Exemplary Klf family members include, Klf1, Klf2, Klf3, Klf-4, Klf5, Klf6, Klf7, Klf8, Klf9, Klf10, Klf11, Klf12, Klf13, Klf14, Klf15, Klf16, and Klf17. Klf2 and Klf-4 were found to be factors capable of generating iPS cells in mice, and related genes Klf1 and Klf5 did as well, although with reduced efficiency. (See, Nakagawa, et al., Nature Biotechnology 26:101-106 (2007), incorporated by reference herein in its entirety.) In some embodiments, variants have at least 85%, 90%, or 95% amino acid sequence identity across their whole sequence compared to a naturally occurring Klf polypeptide family member such as to those listed above or such as listed in Genbank accession number CAX16088 (mouse Klf4) or CAX14962 (human Klf4). Klf polypeptides (e.g., Klf1, Klf4, and Klf5) can be from human, mouse, rat, bovine, porcine, or other animals. Generally, the same species of protein will be used with the species of cells being manipulated. The Klf polypeptide(s) can be a pluripotency factor. The expression of the Klf4 gene or polypeptide can help induce multipotency in a starting cell or a population of starting cells.

A "Myc polypeptide" refers to any of the naturally-occurring members of the Myc family. (See, e.g., Adhikary, S. & Eilers, M., *Nat. Rev. Mol. Cell Biol.* 6:635-645 (2005), incorporated by reference herein in its entirety.) It also includes variants that maintain similar transcription factor activity when compared to the closest related naturally occurring family member (i.e. within at least 50%, 80%, or 90% activity). It further includes polypeptides comprising at least the DNA-binding domain of a naturally occurring family member, and can further comprise a transcriptional activation domain. Exemplary Myc polypeptides include, e.g., c-Myc, N-Myc and L-Myc. In some embodiments, variants have at least 85%, 90%, or 95% amino acid sequence identity across their whole sequence compared to a naturally occurring Myc polypeptide family member, such as to those listed above or such as listed in Genbank accession number CAA25015 (human Myc). Myc polypeptides (e.g., c-Myc) can be from human, mouse, rat, bovine, porcine, or other animals. Generally, the same species of protein will be used with the species of cells being manipulated. The Myc polypeptide(s) can be a pluripotency factor.

A "Sox polypeptide" refers to any of the naturally-occurring members of the SRY-related HMG-box (Sox) transcription factors, characterized by the presence of the high-mobility group (HMG) domain, or variants thereof that maintain similar transcription factor activity when compared to the closest related naturally occurring family member (i.e. within at least 50%, 80%, or 90% activity). It also includes polypeptides comprising at least the DNA-binding domain of the naturally occurring family member, and can further comprise a transcriptional activation domain. (See, e.g., Dang, D. T. et al., *Int. J. Biochem. Cell Biol.* 32:1103-1121 (2000), incorporated by reference herein in its entirety.) Exemplary Sox polypeptides include, e.g., Sox1, Sox-2, Sox3, Sox4, Sox5, Sox6, Sox7, Sox8, Sox9, Sox10, Sox11, Sox12, Sox13, Sox14, Sox15, Sox17, Sox18, Sox-21, and Sox30. Sox1 has been shown to yield iPS cells with a similar efficiency as Sox2, and genes Sox3, Sox15, and Sox18 have also been shown to generate iPS cells, although with somewhat less efficiency than Sox2. (See, Nakagawa, et al., *Nature Biotechnology* 26:101-106 (2007), incorporated by reference herein in its entirety.) In some embodiments, variants have at least 85%, 90%, or 95% amino acid sequence identity across their whole sequence compared to a naturally occurring Sox polypeptide family member such as to those listed above or such as listed in Genbank accession number CAA83435 (human Sox2). Sox polypeptides (e.g., Sox1, Sox2, Sox3, Sox15, or Sox18) can be from human, mouse, rat, bovine, porcine, or other animals. Generally, the same species of protein will be used with the species of cells being manipulated. The Sox polypeptide(s) can be a pluripotency factor. As discussed herein, SOX2 proteins find particular use in the generation of iPSCs.

By "differentiated hypo-immunogenic pluripotent cells" or "differentiated HIP cells" or "dHIP cells" herein is meant iPS cells that have been engineered to possess hypoimmunogenicity (e.g. by the knock out of B2M and CIITA and the knock in of CD47) and then are differentiated into a cell type for ultimate transplantation into subjects. Thus, for example HIP cells can be differentiated into hepatocytes ("dHIP hepatocytes"), into beta-like pancreatic cells or islet organoids ("dHIP beta cells"), into endothelial cells ("dHIP endothelial cells"), etc. Parallel definitions apply to "differentiated HIP/CD64" and differentiated HIPO−/CD64 cells.

The term percent "identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

"Inhibitors," "activators," and "modulators" affect a function or expression of a biologically-relevant molecule. The term "modulator" includes both inhibitors and activators. They may be identified using in vitro and in vivo assays for expression or activity of a target molecule.

"Inhibitors" are agents that, e.g., inhibit expression or bind to target molecules or proteins. They may partially or totally block stimulation or have protease inhibitor activity. They may reduce, decrease, prevent, or delay activation, including inactivation, desensitization, or down regulation of the activity of the described target protein. Modulators may be antagonists of the target molecule or protein.

"Activators" are agents that, e.g., induce or activate the function or expression of a target molecule or protein. They may bind to, stimulate, increase, open, activate, or facilitate the target molecule activity. Activators may be agonists of the target molecule or protein.

"Homologs" are bioactive molecules that are similar to a reference molecule at the nucleotide sequence, peptide sequence, functional, or structural level. Homologs may include sequence derivatives that share a certain percent identity with the reference sequence. Thus, in one embodiment, homologous or derivative sequences share at least a 70 percent sequence identity. In a specific embodiment, homologous or derivative sequences share at least an 80 or 85 percent sequence identity. In a specific embodiment, homologous or derivative sequences share at least a 90 percent sequence identity. In a specific embodiment, homologous or derivative sequences share at least a 95 percent sequence identity. In a more specific embodiment, homologous or derivative sequences share at least an 50, 55, 60, 65, 70, 75, 85, 86, 87, 88, 89, 90, 91, 92, 93, 94, 95, 96, 97, 98, or 99 percent sequence identity. Homologous or derivative nucleic acid sequences may also be defined by their ability to remain bound to a reference nucleic acid sequence under high stringency hybridization conditions. Homologs having a structural or functional similarity to a reference molecule may be chemical derivatives of the reference molecule. Methods of detecting, generating, and screening for structural and functional homologs as well as derivatives are known in the art.

"Hybridization" generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al, Current Protocols in Molecular Biology, Wiley Interscience Publishers (1995), incorporated by reference herein in its entirety.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures.

"Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 Mm sodium phosphate buffer at Ph 6.5 with 750 Mm sodium chloride, 75 Mm sodium citrate at 42° C.; or (3) overnight hybridization in a solution that employs 50% formamide, 5×SSC (0.75 M NaCl, 0.075 M sodium citrate), 50 Mm sodium phosphate (Ph 6.8), 0.1% sodium pyrophosphate, 5×Denhardt's solution, sonicated salmon sperm DNA (50 μl/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein the term "modification" refers to an alteration that physically differentiates the modified molecule from the parent molecule. In one embodiment, an amino acid change in a CD47, HSVtk, EC-CD, or iCasp9 variant polypeptide prepared according to the methods described herein differentiates it from the corresponding parent that has not been modified according to the methods described herein, such as wild-type proteins, a naturally occurring mutant proteins or another engineered protein that does not include the modifications of such variant polypeptide. In another embodiment, a variant polypeptide includes one or more modifications that differentiates the function of the variant polypeptide from the unmodified polypeptide. For example, an amino acid change in a variant polypeptide affects its receptor binding profile. In other embodiments, a variant polypeptide comprises substitution, deletion, or insertion modifications, or combinations thereof. In another embodiment, a variant polypeptide includes one or more modifications that increases its affinity for a receptor compared to the affinity of the unmodified polypeptide.

In one embodiment, a variant polypeptide includes one or more substitutions, insertions, or deletions relative to a corresponding native or parent sequence. In certain embodiments, a variant polypeptide includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-40, 41 to 50, or 51 or more modifications.

By "episomal vector" herein is meant a genetic vector that can exist and replicate autonomously in the cytoplasm of a cell; e.g. it is not integrated into the genomic DNA of the host cell. A number of episomal vectors are known in the art and described below.

By "knock out" in the context of a gene means that the host cell harboring the knock out does not produce a functional protein product of the gene. As outlined herein, a knock out can result in a variety of ways, from removing all or part of the coding sequence, introducing frameshift mutations such that a functional protein is not produced (either truncated or nonsense sequence), removing or altering a regulatory component (e.g. a promoter) such that the gene is not transcribed, preventing translation through binding to mRNA, etc. Generally, the knock out is effected at the genomic DNA level, such that the cells' offspring also carry the knock out permanently.

By "knock in" in the context of a gene means that the host cell harboring the knock in has more functional protein active in the cell. As outlined herein, a knock in can be done in a variety of ways, usually by the introduction of at least one copy of a transgene (tg) encoding the protein into the cell, although this can also be done by replacing regulatory components as well, for example by adding a constitutive promoter to the endogenous gene. In general, knock in technologies result in the integration of the extra copy of the transgene into the host cell.

VII. CELLS OF THE INVENTION

The invention provides compositions and methodologies for transplanted cells to evade the innate immune system. The invention blocks PMN cell killing by reducing cytokine or chemokine attraction or activation, danger-associated molecular patterns (DAMPs, FIG. 1), and pathogen-associated molecular patterns (PAMPs). In some additional aspects of the invention, the cells will be derived from induced pluripotent stem cells (IPSC), O− induced pluripotent stem cells (iPSCO−), embryonic stem cells (ESC), O− embryonic stem cells (ESCO−), hypoimmunogenic pluripotent (HIP) cells, hypoimmunogenic pluripotent O− (HIPO−) cells, or cells derived or differentiated therefrom. In other additional aspects, the transplanted cells will be pluripotent with enhanced CD16, CD32, OR CD64 expression, or cells derived therefrom.

A. Methodologies for Genetic Alterations

The invention includes methods of modifying nucleic acid sequences within cells or in cell-free conditions. Exemplary technologies include homologous recombination, knock-in, ZFNs (zinc finger nucleases), TALENs (transcription activator-like effector nucleases), CRISPR (clustered regularly interspaced short palindromic repeats)/Cas9, and other site-specific nuclease technologies. These techniques enable double-strand DNA breaks at desired locus sites. These controlled double-strand breaks promote homologous recombination at the specific locus sites. This process focuses on targeting specific sequences of nucleic acid molecules, such as chromosomes, with endonucleases that recognize and bind to the sequences and induce a double-stranded break in the nucleic acid molecule. The double-strand break is repaired either by an error-prone non-homologous end-joining (NHEJ) or by homologous recombination (HR).

As will be appreciated by those in the art, a number of different techniques can be used to engineer the pluripotent cells of the invention. In general, these techniques can be used individually or in combination. For example, in the generation of the HIP cells, CRISPR may be used to reduce the expression of active B2M and/or CIITA protein in the engineered cells, with viral techniques (e.g. lentivirus) to knock in the CD47 functionality. Also, as will be appreciated by those in the art, although one embodiment sequentially utilizes a CRISPR step to knock out B2M, followed by a CRISPR step to knock out CIITA with a final step of a lentivirus to knock in the CD47 functionality, these genes can be manipulated in different orders using different technologies.

As is discussed more fully below, transient expression of reprogramming genes is generally done to generate/induce pluripotent stem cells.

a. CRISPR Technologies

In one embodiment, the cells are manipulated using clustered regularly interspaced short palindromic repeats)/Cas ("CRISPR") technologies as is known in the art. CRISPR can be used to generate the starting iPSCs or to generate the HIP cells from the iPSCs. There are a large number of techniques based on CRISPR, see for example Doudna and Charpentier, Science doi:10.1126/science.1258096, hereby incorporated by reference. CRISPR techniques and kits are sold commercially.

b. TALEN Technologies

In some embodiments, the HIP cells of the invention are made using Transcription Activator-Like Effector Nucleases (TALEN) methodologies. TALEN are restriction enzymes combined with a nuclease that can be engineered to bind to and cut practically any desired DNA sequence. TALEN kits are sold commercially.

c. Zinc Finger Technologies

In one embodiment, the cells are manipulated using Zn finger nuclease technologies. Zn finger nucleases are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms, similar to CRISPR and TALENs.

d. Viral Based Technologies

There are a wide variety of viral techniques that can be used to generate the HIP cells of the invention (as well as for the original generation of the iPCSs), including, but not limited to, the use of retroviral vectors, lentiviral vectors, adenovirus vectors and Sendai viral vectors. Episomal vectors used in the generation of iPSCs are described below.

e. Down Regulation of Genes Using Interfering RNA

In other embodiments, genes that encode proteins used in HLA molecules are downregulated by RNAi technologies. RNA interference (RNAi) is a process where RNA molecules inhibit gene expression often by causing specific mRNA molecules to degrade. Two types of RNA molecules—microRNA (miRNA) and small interfering RNA (siRNA)—are central to RNA interference. They bind to the target mRNA molecules and either increase or decrease their activity. RNAi helps cells defend against parasitic nucleic acids such as those from viruses and transposons. RNAi also influences development.

sdRNA molecules are a class of asymmetric siRNAs comprising a guide (antisense) strand of 19-21 bases. They contain a 5' phosphate, 2'Ome or 2'F modified pyrimidines, and six phosphorothioates at the 3' positions. They also contain a sense strand containing 3' conjugated sterol moieties, 2 phosphorothioates at the 3' position, and 2'Ome modified pyrimidines. Both strands contain 2' Ome purines with continuous stretches of unmodified purines not exceeding a length of 3. sdRNA is disclosed in U.S. Pat. No. 8,796,443, incorporated herein by reference in its entirety.

For all of these technologies, well known recombinant techniques are used, to generate recombinant nucleic acids as outlined herein. In certain embodiments, the recombinant nucleic acids (either than encode a desired polypeptide, e.g. CD47, or disruption sequences) may be operably linked to one or more regulatory nucleotide sequences in an expression construct. Regulatory nucleotide sequences will generally be appropriate for the host cell and subject to be treated. Numerous types of appropriate expression vectors and suitable regulatory sequences are known in the art for a variety of host cells. Typically, the one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are also contemplated. The promoters may be either naturally occurring promoters, or hybrid promoters that combine elements of more than one promoter. An expression construct may be present in a cell on an episome, such as a plasmid, or the expression construct may be inserted in a chromosome. In a specific embodiment, the expression vector includes a selectable marker gene to allow the selection of transformed host cells. Certain embodiments include an expression vector comprising a nucleotide sequence encoding a variant polypeptide operably linked to at least one regulatory sequence. Regulatory sequence for use herein include promoters, enhancers, and other expression control elements. In certain embodiments, an expression vector is designed for the choice of the host cell to be transformed, the particular variant polypeptide desired to be expressed, the vector's copy number, the ability to control that copy number, or the expression of any other protein encoded by the vector, such as antibiotic markers.

Examples of suitable mammalian promoters include, for example, promoters from the following genes: ubiquitin/S27a promoter of the hamster (WO 97/15664), Simian vacuolating virus 40 (SV40) early promoter, adenovirus major late promoter, mouse metallothionein-I promoter, the long terminal repeat region of Rous Sarcoma Virus (RSV), mouse mammary tumor virus promoter (MMTV), Moloney murine leukemia virus Long Terminal repeat region, and the early promoter of human Cytomegalovirus (CMV). Examples of other heterologous mammalian promoters are the actin, immunoglobulin or heat shock promoter(s).

In additional embodiments, promoters for use in mammalian host cells can be obtained from the genomes of viruses such as polyoma virus, fowlpox virus (UK 2,211,504 published 5 Jul. 1989), bovine papilloma virus, avian sarcoma virus, cytomegalovirus, a retrovirus, hepatitis-B virus and Simian Virus 40 (SV40). In further embodiments, heterologous mammalian promoters are used. Examples include the actin promoter, an immunoglobulin promoter, and heat-shock promoters. The early and late promoters of SV40 are conveniently obtained as an SV40 restriction fragment which also contains the SV40 viral origin of replication. Fiers et al., Nature 273: 113-120 (1978). The immediate early promoter of the human cytomegalovirus is conveniently obtained as a HindIII E restriction fragment. Greenaway, P. J. et al., Gene 18: 355-360 (1982). The foregoing references are incorporated by reference in their entirety.

B. Generation of Pluripotent Cells

The generation of mouse and human pluripotent stem cells (generally referred to as iPSCs; miPSCs for murine cells or hiPSCs for human cells) is generally known in the art. As will be appreciated by those in the art, there are a variety of different methods for the generation of iPCSs. The original induction was done from mouse embryonic or adult fibroblasts using the viral introduction of four transcription factors, Oct3/4, Sox2, c-Myc and Klf4; see Takahashi and Yamanaka *Cell* 126:663-676 (2006), hereby incorporated by reference in its entirety and specifically for the techniques outlined therein. Since then, a number of methods have been developed; see Seki et al., *World J. Stem Cells* 7(1):116-125 (2015) for a review, and Lakshmipathy and Vermuri, editors, *Methods in Molecular Biology: Pluripotent Stem Cells, Methods and Protocols,* Springer 2013, both of which are hereby expressly incorporated by reference in their entirety, and in particular for the methods for generating hiPSCs (see for example Chapter 3 of the latter reference).

Generally, iPSCs are generated by the transient expression of one or more "reprogramming factors" in the host cell, usually introduced using episomal vectors. Under these conditions, small amounts of the cells are induced to become iPSCs (in general, the efficiency of this step is low, as no selection markers are used). Once the cells are "reprogrammed", and become pluripotent, they lose the episomal vector(s) and produce the factors using the endogenous genes. This loss of the episomal vector(s) results in cells that are called "zero footprint" cells. This is desirable as the fewer genetic modifications (particularly in the genome of the host cell), the better. Thus, it is preferred that the resulting hiPSCs have no permanent genetic modifications.

As is also appreciated by those of skill in the art, the number of reprogramming factors that can be used or are used can vary. Commonly, when fewer reprogramming factors are used, the efficiency of the transformation of the cells to a pluripotent state goes down, as well as the "pluripotency", e.g. fewer reprogramming factors may result in cells that are not fully pluripotent but may only be able to differentiate into fewer cell types.

In some embodiments, a single reprogramming factor, OCT4, is used. In other embodiments, two reprogramming factors, OCT4 and KLF4, are used. In other embodiments, three reprogramming factors, OCT4, KLF4 and SOX2, are used. In other embodiments, four reprogramming factors, OCT4, KLF4, SOX2 and c-Myc, are used. In other embodiments, 5, 6 or 7 reprogramming factors can be used selected from SOKMNLT; SOX2, OCT4 (POU5F1), KLF4, MYC, NANOG, LIN28, and SV40L T antigen.

In general, these reprogramming factor genes are provided on episomal vectors such as are known in the art and commercially available. For example, ThermoFisher/Invitrogen sell a sendai virus reprogramming kit for zero footprint generation of hiPSCs, see catalog number A34546. ThermoFisher also sells EBNA-based systems as well, see catalog number A14703.

In addition, there are a number of commercially available hiPSC lines available; see, e.g., the Gibco® Episomal hiPSC line, K18945, which is a zero footprint, viral-integration-free human iPSC cell line (see also Burridge et al, 2011, supra).

In general, as is known in the art, iPSCs are made from non-pluripotent cells such as CD34+ cord blood cells, fibroblasts, etc., by transiently expressing the reprogramming factors as described herein.

For example, successful iPSCs were also generated using only Oct3/4, Sox2 and Klf4, while omitting the C-Myc, although with reduced reprogramming efficiency.

In general, iPSCs are characterized by the expression of certain factors that include KLF4, Nanog, OCT4, SOX2, ESRRB, TBX3, c-Myc and TCL1. New or increased expression of these factors for purposes of the invention may be via induction or modulation of an endogenous locus or from expression from a transgene.

For example, murine iPSCs can be generated using the methods of Diecke et al, *Sci Rep.* 2015, Jan. 28; 5:8081 (doi:10.1038/srep08081), hereby incorporated by reference in its entirety and specifically for the methods and reagents for the generation of the miPSCs. See also, e.g., Burridge et al., *PLoS One,* 2011 6(4):18293, hereby incorporated by reference in its entirety and specifically for the methods outlined therein.

In some cases, the pluripotency of the cells is measured or confirmed as outlined herein, for example by assaying for reprogramming factors or by conducting differentiation reactions as outlined herein and in the Examples.

C. Generation of Hypo-Immunogenic Pluripotent (HIP) Cells

Generating HIP cells from pluripotent cells is done with as few as three genetic changes, resulting in minimal disruption of cellular activity but conferring immunosilencing to the cells.

As discussed herein, one embodiment utilizes a reduction or elimination in the protein activity of MHC I and II (HLA I and II when the cells are human). This can be done by altering genes encoding their component. In one embodiment, the coding region or regulatory sequences of the gene are disrupted using CRISPR. In another embodiment, gene translation is reduced using interfering RNA technologies. The third change is a change in a gene that regulates susceptibility to macrophage phagocytosis, such as CD47, and this is generally a "knock in" of a gene using viral technologies.

In some cases, where CRISPR is being used for the genetic modifications, hiPSC cells that contain a Cas9 construct that enable high efficiency editing of the cell line can be used; see, e.g., the Human Episomal Cas9 iPSC cell line, A33124, from Life Technologies.

1. HLA-I Reduction

The HIP cells of the invention include a reduction in MHC I function (HLA I when the cells are derived from human cells).

As will be appreciated by those in the art, the reduction in function can be accomplished in a number of ways, including removing nucleic acid sequences from a gene, interrupting the sequence with other sequences, or altering the regulatory components of the nucleic acid. For example, all or part of a coding region of the gene of interest can be removed or replaced with "nonsense" sequences, frameshift mutations can be made, all or part of a regulatory sequence such as a promoter can be removed or replaced, translation initiation sequences can be removed or replaced, etc.

As will be appreciated by those in the art, the successful reduction of the MHC I function (HLA I when the cells are derived from human cells) in the pluripotent cells can be measured using techniques known in the art and as described below; for example, FACS techniques using labeled antibodies that bind the HLA complex; for example, using commercially available HLA-A, B, C antibodies that bind to the the alpha chain of the human major histocompatibility HLA Class I antigens.

a. B2M Alteration

In one embodiment, the reduction in HLA-I activity is done by disrupting the expression of the β-2 microglobulin gene in the pluripotent stem cell, the human sequence of which is disclosed herein. This alteration is generally referred to herein as a gene "knock out", and in the HIP cells of the invention it is done on both alleles in the host cell. Generally the techniques to do both disruptions is the same.

A particularly useful embodiment uses CRISPR technology to disrupt the gene. In some cases, CRISPR technology is used to introduce small deletions/insertions into the coding region of the gene, such that no functional protein is produced, often the result of frameshift mutations that result in the generation of stop codons such that truncated, non-functional proteins are made.

Accordingly, a useful technique is to use CRISPR sequences designed to target the coding sequence of the B2M gene in mouse or the B2M gene in human. After gene editing, the transfected iPSC cultures are dissociated to single cells. Single cells are expanded to full-size colonies and tested for CRISPR edit by screening for presence of aberrant sequence from the CRISPR cleavage site. Clones with deletions in both alleles are picked. Such clones did not express B2M as demonstrated by PCR and did not express HLA-I as demonstrated by FACS analysis (see examples 1 and 6, for example).

Assays to test whether the B2M gene has been inactivated are known and described herein. In one embodiment, the assay is a Western blot of cells lysates probed with antibodies to the B2M protein. In another embodiment, reverse transcriptase polymerase chain reactions (rt-PCR) confirms the presence of the inactivating alteration.

In addition, the cells can be tested to confirm that the HLA I complex is not expressed on the cell surface. This may be assayed by FACS analysis using antibodies to one or more HLA cell surface components as discussed above.

It is noteworthy that others have had poor results when trying to silence the B2M genes at both alleles. See, e.g. Gornalusse et al., *Nature Biotech.* Doi/10.1038/nbt.3860).

2. HLA-II Reduction

In addition to a reduction in HLA I, the HIP cells of the invention also lack MHC II function (HLA II when the cells are derived from human cells).

As will be appreciated by those in the art, the reduction in function can be accomplished in a number of ways, including removing nucleic acid sequences from a gene, adding nucleic acid sequences to a gene, disrupting the reading frame, interrupting the sequence with other sequences, or altering the regulatory components of the nucleic acid. In one embodiment, all or part of a coding region of the gene of interest can be removed or replaced with "nonsense" sequences. In another embodiment, regulatory sequences such as a promoter can be removed or replaced, translation initiation sequences can be removed or replaced, etc.

The successful reduction of the MHC II function (HLA II when the cells are derived from human cells) in the pluripotent cells or their derivatives can be measured using techniques known in the art such as Western blotting using antibodies to the protein, FACS techniques, rt-PCR techniques, etc.

a. CIITA Alteration

In one embodiment, the reduction in HLA-II activity is done by disrupting the expression of the CIITA gene in the pluripotent stem cell, the human sequence of which is shown herein. This alteration is generally referred to herein as a gene "knock out", and in the HIP cells of the invention it is done on both alleles in the host cell.

Assays to test whether the CIITA gene has been inactivated are known and described herein. In one embodiment, the assay is a Western blot of cells lysates probed with antibodies to the CIITA protein. In another embodiment, reverse transcriptase polymerase chain reactions (rt-PCR) confirms the presence of the inactivating alteration.

In addition, the cells can be tested to confirm that the HLA II complex is not expressed on the cell surface. Again, this assay is done as is known in the art. Exemplary analyses include Western Blots or FACS analysis using commercial antibodies that bind to human HLA Class II HLA-DR, DP and most DQ antigens as outlined below.

A particularly useful embodiment uses CRISPR technology to disrupt the CIITA gene. CRISPRs were designed to target the coding sequence of the Ciita gene in mouse or the CIITA gene in human, an essential transcription factor for all MHC II molecules. After gene editing, the transfected iPSC cultures were dissociated into single cells. They were expanded to full-size colonies and tested for successful CRISPR editing by screening for the presence of an aberrant sequence from the CRISPR cleavage site. Clones with deletions did not express CIITA as determined by PCR and did not express MHC II/HLA-II as determined by FACS analysis.

3. Phagocytosis Reduction

In addition to the reduction of HLA I and II (or MHC I and II), generally using B2M and CIITA knock-outs, the HIP cells of the invention have a reduced susceptibility to macrophage phagocytosis and NK cell killing. The resulting HIP cells "escape" the immune macrophage and innate pathways due to one or more CD47 transgenes.

a. CD47 Increase

In some embodiments, reduced macrophage phagocytosis and NK cell killing susceptibility results from increased CD47 on the HIP cell surface. This is done in several ways as will be appreciated by those in the art using "knock in" or transgenic technologies. In some cases, increased CD47 expression results from one or more CD47 transgene.

Accordingly, in some embodiments, one or more copies of a CD47 gene is added to the HIP cells under control of an inducible or constitutive promoter, with the latter being preferred. In some embodiments, a lentiviral construct is employed as described herein or known in the art. CD47 genes may integrate into the genome of the host cell under the control of a suitable promoter as is known in the art.

The HIP cell lines were generated from B2M−/− CIITA−/− iPSCs. Cells containing lentivirus vectors expressing CD47 were selected using a Blasticidin marker. The CD47 gene sequence was synthesized and the DNA was cloned into the plasmid Lentivirus pLenti6/V5 with a blasticidin resistance (Thermo Fisher Scientific, Waltham, Mass.)

In some embodiments, the expression of the CD47 gene can be increased by altering the regulatory sequences of the endogenous CD47 gene, for example, by exchanging the endogenous promoter for a constitutive promoter or for a different inducible promoter. This can generally be done using known techniques such as CRISPR.

Once altered, the presence of sufficient CD47 expression can be assayed using known techniques such as those described in the Examples, such as Western blots, ELISA assays or FACS assays using anti-CD47 antibodies. In general, "sufficiency" in this context means an increase in the expression of CD47 on the HIP cell surface that silences NK cell killing. The natural expression levels on cells is too low to protect them from NK cell lysis once their MHC I is removed.

4. Suicide Genes

In some embodiments, the invention provides hypoimmunogenic pluripotent cells that comprise a "suicide gene" or "suicide switch". These are incorporated to function as a "safety switch" that can cause the death of the hypoimmunogenic pluripotent cells should they grow and divide in an undesired manner. The "suicide gene" ablation approach includes a suicide gene in a gene transfer vector encoding a protein that results in cell killing only when activated by a specific compound. A suicide gene may encode an enzyme that selectively converts a nontoxic compound into highly toxic metabolites. The result is specifically eliminating cells expressing the enzyme. In some embodiments, the suicide gene is the herpesvirus thymidine kinase (HSV-tk) gene and the trigger is ganciclovir. In other embodiments, the suicide gene is the *Escherichia coli* cytosine deaminase (EC-CD) gene and the trigger is 5-fluorocytosine (5-FC) (Barese et al., *Mol. Therap.* 20(10):1932-1943 (2012), Xu et al., *Cell Res.* 8:73-8 (1998), both incorporated herein by reference in their entirety.)

In other embodiments, the suicide gene is an inducible Caspase protein. An inducible Caspase protein comprises at least a portion of a Caspase protein capable of inducing apoptosis. In one embodiment, the portion of the Caspase protein is exemplified in SEQ ID NO:6. In preferred embodiments, the inducible Caspase protein is iCasp9. It comprises the sequence of the human FK506-binding protein, FKBP12, with an F36V mutation, connected through a series of amino acids to the gene encoding human caspase 9. FKBP12-F36V binds with high affinity to a small-molecule dimerizing agent, AP1903. Thus, the suicide function of iCasp9 in the instant invention is triggered by the administration of a chemical inducer of dimerization (CID). In some embodiments, the CID is the small molecule drug AP1903. Dimerization causes the rapid induction of apoptosis. (See WO2011146862; Stasi et al, *N. Engl. J. Med* 365;18 (2011); Tey et al., *Biol. Blood Marrow Transplant.* 13:913-924 (2007), each of which are incorporated by reference herein in their entirety.)

5. CD16, CD32, or CD64 Expression

In some aspects of the invention, the cells have a reduced susceptibility to ADCC and CDC resulting from increased CD16, CD32, or CD64 expression. The resulting cells sequester antibodies due to the increased expression. In one embodiment, the cells comprise one or more CD16, CD32, or CD64 transgenes.

a. CD16, CD32, or CD64 Increase

In some aspects, reduced ADCC or CDC susceptibility results from increased CD16, CD32, or CD64 on the cell surface. This is done in several ways as will be appreciated by those in the art using "knock in" or transgenic technologies. In some cases, increased CD16, CD32, or CD64 expression results from one or more transgenes.

Accordingly, in some embodiments, one or more copies of a CD16, CD32, or CD64 gene is added to the cells under control of an inducible or constitutive promoter, with the latter being preferred. In some embodiments, a lentiviral construct is employed as described herein or known in the art. The genes may integrate into the genome of the host cell under the control of a suitable promoter as is known in the art.

Cells containing lentivirus vectors expressing CD16, CD32, or CD64 are selected using a Blasticidin marker. The gene sequence is synthesized and the DNA may be cloned, for instance, into the plasmid Lentivirus pLenti6/V5 with a blasticidin resistance (Thermo Fisher Scientific, Waltham, MA)

In some embodiments, the expression of the gene can be increased by altering the regulatory sequences of the endogenous CD16, CD32, or CD64 gene, for example, by exchanging the endogenous promoter for a constitutive promoter or for a different inducible promoter. This can generally be done using known techniques such as CRISPR.

Once altered, the presence of sufficient expression can be assayed using known techniques such as those described in the Examples, such as Western blots, ELISA assays or FACS assays using anti-CD16, CD32, or CD64 antibodies. In general, "sufficiency" in this context means an increase in expression the cell surface that sequesters antibodies and inhibits ADCC or CDC.

6. Assays for HIP Phenotypes and Retention of Pluripotency

Once the HIP cells have been generated, they may be assayed for their hypo-immunogenicity and/or retention of pluripotency as is generally described herein and in the examples.

For example, hypo-immunogenicity are assayed using a number of techniques One exemplary technique includes transplantation into allogeneic hosts and monitoring for HIP cell growth (e.g. teratomas) that escape the host immune system. HIP derivatives are transduced to express luciferase and can then followed using bioluminescence imaging. Similarly, the T cell and/or B cell response of the host animal to the HIP cells are tested to confirm that the HIP cells do not cause an immune reaction in the host animal. T cell function is assessed by Elispot, Elisa, FACS, PCR, or mass cytometry (CYTOF). B cell response or antibody response is assessed using FACS or luminex. Additionally, or alternatively, the cells may be assayed for their ability to avoid innate immune responses, e.g. NK cell killing. NK cell lytolytic activity is assessed in vitro or in vivo using techniques known in the art.

Similarly, the retention of pluripotency is tested in a number of ways. In one embodiment, pluripotency is assayed by the expression of certain pluripotency-specific factors as generally described herein. Additionally or alternatively, the HIP cells are differentiated into one or more cell types as an indication of pluripotency.

D. Generation of HIPO− CD16, CD32, or CD64-Overexpressing Cells

In some aspects of the invention, the HIP cells generated as above will already be HIPO− cells because the process will have started with pluripotent cells having an O− blood type.

Other aspects of the invention involve the enzymatic conversion of A and B antigens. In preferred aspects, the B antigen is converted to O using an enzyme. In more preferred aspects, the enzyme is an α-galactosidase. This enzyme eliminates the terminal galactose residue of the B antigen. Other aspects of the invention involve the enzymatic conversion of A antigen to O. In preferred aspects, the A antigen is converted to O using an α-N-acetylgalactosaminidase. Enzymatic conversion is discussed, e.g., in Olsson et al., *Transfusion Clinique et Biologique* 11:33-39 (2004); U.S. Pat. Nos. 4,427,777, 5,606,042, 5,633,130, 5,731,426, 6,184,017, 4,609,627, and 5,606,042; and Int'l Pub. No. WO9923210, each of which are incorporated by reference herein in their entirety.

Other embodiments of the invention involve genetically engineering the cells by knocking out the ABO gene Exon 7 or silencing the SLC14A1 (JK) gene. Other embodiments of the invention involve knocking out the C and E antigens of the Rh blood group system (RH), K in the Kell system (KEL), Fya and Fy3 in the Duffy system (FY), Jkb in the Kidd system (JK), or U and S in the MNS blood group system. Any knockout methodology known in the art or described herein, such as CRISPR, talens, or homologous recombination, may be employed.

E. Preferred Embodiments of the Invention

The HIP, HIPO−, iPSC, iPSCO−, ESC, or ESCO− cells, including those that overexpress CD16, CD32, or CD64, or derivatives thereof, may be used to treat, for example, Type 1 diabetes, cardiac diseases, neurological diseases, cancer, blindness, vascular diseases, and others that respond to regenerative medicine therapies. In particular, the invention contemplates using the cells for differentiation into any cell type. Particular aspects are described below:

In one aspect, the cells of the present invention comprise a nucleic acid encoding a chimeric antigen receptor (CAR). The CAR can comprise an extracellular domain, a transmembrane domain, and an intracellular signaling domain. In the aspects, the CAR cell is derived from a HIP cell, a HIPO− cell, or overexpresses CD16, CD32, or CD64.

In some embodiments, the extracellular domain binds to an antigen selected from the group consisting of CD19, CD20, CD22, CD38, CD123, CS1, CD171, BCMA, MUC16, ROR1, and WT1. In certain embodiments, the extracellular domain comprises a single chain variable fragment (scFv). In some embodiments, the transmembrane domain comprises CD3ζ, CD4, CD8α, CD28, 4-1BB, OX40, ICOS, CTLA-4, PD-1, LAG-3, and BTLA. In certain embodiments, the intracellular signaling domain comprises CD3ζ, CD28, 4-1BB, OX40, ICOS, CTLA-4, PD-1, LAG-3, and BTLA.

In certain embodiments, the CAR comprises an anti-CD19 scFv domain, a CD28 transmembrane domain, and a CD3 zeta signaling intracellular domain. In some embodiments, the CAR comprises anti-CD19 scFv domain, a CD28 transmembrane domain, a 4-1BB signaling intracellular domain, and a CD3 zeta signaling intracellular domain.

In another aspect of the invention, provided is an isolated CAR-T overexpressing cell CD16, CD32, or CD64 produced by in vitro differentiation of any one of the cells described herein. In some embodiments, the cell is a cytotoxic hypoimmune CAR-T cell.

In various embodiments, the in vitro differentiation comprises culturing the cell carrying a CAR construct in a culture media comprising one or more growth factors or cytokines selected from the group consisting of bFGF, EPO, Flt3L, IGF, IL-3, IL-6, IL-15, GM-CSF, SCF, and VEGF. In some embodiments, the culture media further comprises one or more selected from the group consisting of a BMP activator, a GSK3 inhibitor, a ROCK inhibitor, a TGFβ receptor/ALK inhibitor, and a NOTCH activator.

In particular embodiments, the isolated CAR-T cell of the invention produced by in vitro differentiation is used as a treatment of cancer.

In another aspect of the invention, provided is a method of treating a patient with cancer by administering a composition comprising a therapeutically effective amount of any of the isolated CAR-T cells described herein in combination with a PMN-inhibitory strategy. In some embodiments, the composition further comprises a therapeutically effective carrier.

In some embodiments, the administration step comprises intravenous administration, subcutaneous administration, intranodal administration, intratumoral administration, intrathecal administration, intrapleural administration, and intraperitoneal administration. In certain instances, the administration further comprises a bolus or by continuous perfusion.

In some embodiments, the cancer is a blood cancer selected from the group consisting of leukemia, lymphoma, and myeloma. In various embodiments, the cancer is a solid tumor cancer or a liquid tumor cancer.

In another aspect, the present invention provides a method of making any one of the isolated CAR-T derived from a pluripotent cell including a HIP cell, a HIPO− cell, or one that overexpresses CD16, CD32, or CD64 as described herein. The method includes in vitro differentiating of any one of the cells of the invention wherein in vitro differentiating comprises culturing them in a culture media comprising one or more growth factors or cytokines selected from the group consisting of bFGF, EPO, Flt3L, IGF, IL-2, IL-3, IL-6, IL-7, IL-15, GM-CSF, SCF, and VEGF. In some embodiments, the culture media further comprises one or more selected from the group consisting of a BMP activator, a GSK3 inhibitor, a ROCK inhibitor, a TGFβ receptor/ALK inhibitor, and a NOTCH activator.

In some aspects, the in vitro differentiating comprises culturing the pluripotent cells on feeder cells. In various embodiments, the in vitro differentiating comprises culturing in simulated microgravity. In certain instances, the culturing in simulated microgravity is for at least 72 hours.

In some aspects, provided herein is an isolated, therapeutic cardiac cell that is administered with a strategy for reducing PMN killing. In other aspects, provided herein is a method of treating a patient suffering from a heart condition or disease with a therapeutic cardiac cell and a strategy for reducing PMN killing. The method comprises administering a composition comprising a therapeutically effective amount of a population of any one of the isolated cardiac cells derived from cells of the invention as described herein in combination with a PMN inhibiting strategy. In some aspects, a PMN cell receptor is targeted. In other aspects, the cardiac cell has an elevated level of CD200 or CD99 expression. The composition further comprises a therapeutically effective carrier.

In some embodiments, the administration comprises implantation into the patient's heart tissue, intravenous injection, intraarterial injection, intracoronary injection, intramuscular injection, intraperitoneal injection, intramyocardial injection, trans-endocardial injection, trans-epicardial injection, or infusion.

In some embodiments, the heart condition or disease is selected from the group consisting of pediatric cardiomyopathy, age-related cardiomyopathy, dilated cardiomyopathy, hypertrophic cardiomyopathy, restrictive cardiomyopathy, chronic ischemic cardiomyopathy, peripartum cardiomyopathy, inflammatory cardiomyopathy, other cardiomyopathy, myocarditis, myocardial ischemic reperfusion injury, ventricular dysfunction, heart failure, congestive heart failure, coronary artery disease, end stage heart disease, atherosclerosis, ischemia, hypertension, restenosis, angina pectoris, rheumatic heart, arterial inflammation, or cardiovascular disease.

In some aspects, provided herein is a method of using a population of hypoimmune cardiac cells from a population of HIP, HIPO−, or HIPO−/CD16, CD32, or CD64 cells by in vitro differentiation, wherein endogenous β-2 microglobulin (B2M) gene activity and endogenous class II transactivator (CIITA) gene activity have been eliminated and CD47 expression has been increased in the HIPO− cells. The method comprises: (a) culturing a population of HIPO− cells in a culture medium comprising a GSK inhibitor; (b) culturing the population of HIPO− cells in a culture medium comprising a WNT antagonist to produce a population of pre-cardiac cells; and (c) culturing the population of pre-cardiac cells in a culture medium comprising insulin to produce a population of hypoimmune cardiac cells.

In some embodiments, the GSK inhibitor is CHIR-99021, a derivative thereof, or a variant thereof. In some instances, the GSK inhibitor is at a concentration ranging from about 2 μM to about 10 μM. In some embodiments, the WNT antagonist is IWR1, a derivative thereof, or a variant thereof. In some instances, the WNT antagonist is at a concentration ranging from about 2 μM to about 10 μM.

Some aspects of the invention utilize a therapeutic endothelial cell in combination with a PMN-inhibitory strategy. In some aspects, the endothelial cell is derived from a HIP cell, a HIPO− cell, or overexpresses CD16, CD32, or CD64. In other aspects, the therapeutic endothelial cell of the invention is selected from the group consisting of a capillary endothelial cell, vascular endothelial cell, aortic endothelial cell, brain endothelial cell, and renal endothelial cell.

In some aspects, provided herein is a method of treating a patient suffering from a vascular condition or disease. In some embodiments, the method comprises administering a composition comprising a therapeutically effective amount of a population of isolated, engineered endothelial cells of the invention in combination with a PMN-inhibitory strategy. In some embodiments, the composition further comprises a therapeutically effective carrier or excipient. In some embodiments, the administration comprises implantation into the patient's heart tissue, intravenous injection, intraarterial injection, intracoronary injection, intramuscular injection, intraperitoneal injection, intramyocardial injection, trans-endocardial injection, trans-epicardial injection, or infusion.

In some embodiments, the vascular condition or disease is selected from the group consisting of, vascular injury, cardiovascular disease, vascular disease, ischemic disease, myocardial infarction, congestive heart failure, hypertension, ischemic tissue injury, limb ischemia, stroke, neuropathy, and cerebrovascular disease.

In some aspects, provided herein is a method of producing a population of hypoimmune endothelial cells from a population of HIP, HIPO−, iPSC, iPSCO−, ESC, or ESCO− cells, including those that overexpress CD16, CD32, or CD64, or derivatives thereof. The method comprises: (a) culturing a population of HIPO− cells in a first culture medium comprising a GSK inhibitor; (b) culturing the population of HIPO− cells in a second culture medium comprising VEGF and bFGF to produce a population of pre-endothelial cells; and (c) culturing the population of pre-endothelial cells in a third culture medium comprising a ROCK inhibitor and an ALK inhibitor to produce a population of hypoimmune endothelial cells.

In some embodiments, the GSK inhibitor is CHIR-99021, a derivative thereof, or a variant thereof. In some instances, the GSK inhibitor is at a concentration ranging from about 1 μM to about 10 μM. In some embodiments, the ROCK inhibitor is Y-27632, a derivative thereof, or a variant thereof. In some instances, the ROCK inhibitor is at a concentration ranging from about 1 μM to about 20 μM. In some embodiments, the ALK inhibitor is SB-431542, a derivative thereof, or a variant thereof. In some instances, the ALK inhibitor is at a concentration ranging from about 0.5 μM to about 10 μM.

In some embodiments, the first culture medium comprises from 2 μM to about 10 μM of CHIR-99021. In some embodiments, the second culture medium comprises 50 ng/ml VEGF and 10 ng/ml bFGF. In other embodiments, the second culture medium further comprises Y-27632 and SB-431542. In various embodiments, the third culture medium comprises 10 μM Y-27632 and 1 μM SB-431542. In certain embodiments, the third culture medium further comprises VEGF and bFGF. In particular instances, the first culture medium and/or the second medium is absent of insulin.

Some aspects of the invention utilize a dopaminergic neuron (DN) in combination with a PMN-inhibitory strategy. In other aspects, the DN cell is derived from a HIP cell, a HIPO− cell, or overexpresses CD16, CD32, or CD64.

In some aspects, the isolated dopaminergic neuron is selected from the group consisting of a neuronal stem cell, neuronal progenitor cell, immature dopaminergic neuron, and mature dopaminergic neuron.

In some aspects, provided herein is a method of treating a patient suffering from a neurodegenerative disease or condition. In some embodiments, the method comprises administering a composition comprising a therapeutically effective amount of a population of DN cells and utilizing a PMN-inhibitory strategy. In some aspects, the composition further comprises a therapeutically effective carrier. In some aspects, the population of the isolated hypoimmune dopaminergic neurons is on a biodegradable scaffold. The administration may comprise transplantation or injection. In some aspects, the neurodegenerative disease or condition is selected from the group consisting of Parkinson's disease, Huntington disease, and multiple sclerosis.

In some aspects, the invention provides a method of producing a population of the DN cells by in vitro differentiation. In some embodiments, the endogenous β-2 microglobulin (B2M) gene activity and endogenous class II transactivator (CIITA) gene activity have been eliminated, CD47 expression has been increased, the blood group is O and Rh−, or CD16, CD32, or CD64 is overexpressed. In some aspects, the method comprises (a) culturing the population of cells in a first culture medium comprising one or more factors selected from the group consisting of sonic hedgehog (SHH), BDNF, EGF, bFGF, FGF8, WNT1, retinoic acid, a GSK3β inhibitor, an ALK inhibitor, and a ROCK inhibitor to produce a population of immature dopaminergic neurons; and (b) culturing the population of immature dopaminergic neurons in a second culture medium that is different than the first culture medium to produce a population of dopaminergic neurons.

In some embodiments, the GSKIβ inhibitor is CHIR-99021, a derivative thereof, or a variant thereof. In some instances, the GSKβ inhibitor is at a concentration ranging from about 2 μM to about 10 μM. In some embodiments, the ALK inhibitor is SB-431542, a derivative thereof, or a variant thereof. In some instances, the ALK inhibitor is at a concentration ranging from about 1 μM to about 10 μM. In some embodiments, the first culture medium and/or second culture medium are absent of animal serum.

In some aspects of the invention, the method also comprises isolating the population of DN cells from non-DN cells. In some aspects, the method further comprises cryopreserving the isolated population of hypoimmune dopaminergic neurons.

Some aspects of the invention utilize an isolated engineered hypoimmune pancreatic islet cell in combination with a PMN-inhibitory strategy. In other aspects, the pancreatic islet cell is derived from a HIP cell, a HIPO− cell, or overexpresses CD16, CD32, or CD64.

In some embodiments, the isolated hypoimmune pancreatic islet cell is selected from the group consisting of a pancreatic islet progenitor cell, immature pancreatic islet cell, and mature pancreatic islet cell.

In some aspects, provided herein is a method of treating a patient suffering from diabetes. The method comprises administering a composition comprising a therapeutically effective amount of a population of any one of the pancreatic islet cells described herein in combination with a PMN-inhibitory strategy. In some embodiments, the composition further comprises a therapeutically effective carrier. In some embodiments, the population of the isolated hypoimmune pancreatic islet cells is on a biodegradable scaffold. In some instances, the administration comprises transplantation or injection.

In some aspects, provided herein is a method of producing a population of hypoimmune pancreatic islet cells from a population of CD16, CD32, or CD64-overexpressing cells by in vitro differentiation. In some embodiments, the endogenous β-2 microglobulin (B2M) gene activity and endogenous class II transactivator (CIITA) gene activity have been eliminated, CD47 expression has been increased, the blood type is O and Rh− in the HIPO− cells. The method comprises: (a) culturing the population of CD16, CD32, or CD64-overexpressing cells in a first culture medium comprising one or more factors selected from the group consisting insulin-like growth factor (IGF), transforming growth factor (TGF), fibroblast growth factor (EGF), epidermal growth factor (EGF), hepatocyte growth factor (HGF), sonic hedgehog (SHH), and vascular endothelial growth factor (VEGF), transforming growth factor-β (TGFβ) superfamily, bone morphogenic protein-2 (BMP2), bone morphogenic protein-7 (BMP7), a GSK3β inhibitor, an ALK inhibitor, a BMP type 1 receptor inhibitor, and retinoic acid to produce a population of immature pancreatic islet cells; and (b) culturing the population of immature pancreatic islet cells in a second culture medium that is different than the first culture medium to produce a population of hypoimmune pancreatic islet cells.

In some embodiments, the GSK inhibitor is CHIR-99021, a derivative thereof, or a variant thereof. In some instances, the GSK inhibitor is at a concentration ranging from about 2 μM to about 10 μM. In some embodiments, the ALK inhibitor is SB-431542, a derivative thereof, or a variant thereof. In some instances, the ALK inhibitor is at a concentration ranging from about 1 μM to about 10 μM. In some embodiments, the first culture medium and/or second culture medium are absent of animal serum.

In some embodiments, the method also comprises isolating the pancreatic islet cells from non-pancreatic islet cells. In some embodiments, the method further comprises cryopreserving the isolated population of hypoimmune pancreatic islet cells.

In some aspects, provided herein is an isolated, engineered hypoimmune retinal pigmented epithelium (RPE) cell in combination with a PMN-inhibitory strategy. In other aspects, the RPE cell differentiated from a HIP cell, a HIPO− cell, or overexpresses CD16, CD32, or CD64.

In some embodiments, the isolated hypoimmune RPE cell is selected from the group consisting of a RPE progenitor cell, immature RPE cell, mature RPE cell, and functional RPE cell.

In some aspects, provided herein is a method of treating a patient suffering from an ocular condition. The method comprises administering a composition comprising a therapeutically effective amount of a population of any one of a population of the isolated RPE cells described herein in combination with a PMN-inhibitory strategy. In some embodiments, the composition further comprises a therapeutically effective carrier. In some embodiments, the population of the isolated hypoimmune RPE cells is on a biodegradable scaffold. In some embodiments, the administration comprises transplantation or injection to the patient's retina. In some embodiments, the ocular condition is selected from the group consisting of wet macular degeneration, dry macular degeneration, juvenile macular degeneration, Leber's Congenital Ameurosis, retinitis pigmentosa, and retinal detachment.

In some aspects, provided herein is a method of producing a population of RPE cells from a population of cells by in vitro differentiation. In some embodiments, the endogenous β-2 microglobulin (B2M) gene activity and endogenous class II transactivator (CIITA) gene activity have been eliminated and CD47 expression has been increased in the HIPO− cells. The method comprises: (a) culturing the population of HIPO− cells in a first culture medium comprising any one of the factors selected from the group consisting of activin A, bFGF, BMP4/7, DKK1, IGF1, noggin, a BMP inhibitor, an ALK inhibitor, a ROCK inhibitor, and a VEGFR inhibitor to produce a population of pre-RPE cells; and (b) culturing the population of pre-RPE cells in a second culture medium that is different than the first culture medium to produce a population of hypoimmune RPE cells.

In some embodiments, the ALK inhibitor is SB-431542, a derivative thereof, or a variant thereof. In some instances, the ALK inhibitor is at a concentration ranging from about 2 μM to about 10 μM. In some embodiments, the ROCK inhibitor is Y-27632, a derivative thereof, or a variant thereof. In some instances, the ROCK inhibitor is at a concentration ranging from about 1 μM to about 10 μM.

In some embodiments, the first culture medium and/or second culture medium are absent of animal serum.

In some embodiments, the method further comprises isolating the population of hypoimmune RPE cells from non-RPE cells. In some embodiments, the method further comprises cryopreserving the isolated population of hypoimmune RPE cells.

In one aspect, human pluripotent stem cells (PSCs) resist ADCC or CDC by CD16, CD32, or CD64-overexpression. In some embodiments, they are hypoimmune pluripotent stem cells (hiPSC). They are rendered hypo-immunogenic by a) the disruption of the B2M gene at each allele (e.g. B2M −/−), b) the disruption of the CIITA gene at each allele (e.g. CIITA −/−), and c) by the overexpression of the CD47 gene (CD47+, e.g. through introducing one or more additional copies of the CD47 gene or activating the genomic gene). This renders the hiPSC population B2M−/− CIITA −/− CD47tg. In a preferred aspect, the cells are non-immunogenic. In another embodiment, the HIP cells are rendered non-immunogenic B2M−/− CIITA −/− CD47tg as described above but are further modified by including an inducible suicide gene that is induced to kill the cells in vivo when required. In other aspects, CD16, CD32, or CD64-overexpressing HIPO cells are created when HIP cells are rendered blood type O by by knocking out the ABO gene Exon 7 or silencing the SLC14A1 (JK) gene and the cells are rendered Rh− by knocking out the C and E antigens of the Rh blood group system (RH), K in the Kell system (KEL), Fya and Fy3 in the Duffy system (FY), Jkb in the Kidd system (JK), or U and S in the MNS blood group system.

Alpha-1 antitrypsin deficiency (A1AD) is a genetic disorder that may result in lung disease or liver disease and is caused by a mutation in the SERPINA1 gene. The deficiency in A1AT leads to an imbalance with high neutrophil elastase activity, an enzyme that can disrupt connective tissue in the lung. Individuals with A1AD may develop chronic obstructive pulmonary disease or emphysema. Treatment of advanced disease includes intravenous infusions of the A1AT protein derived from donated human plasma or lung transplantation. The invention provides a cell therapy product to replace the missing A1AT and prevent progression of the disease. In some embodiments, the A1AT therapy maintains physiologic A1AT levels and prevents morphologic and functional diseases, e.g. in the lungs.

Thus, the invention provides an isolated, engineered hypoimmune cell that expresses a therapeutic protein. In some aspects of the invention, that therapeutic protein is A1AT. In other aspects, the therapeutic protein, e.g. A1AT, is transplanted into a subject in combination with a PMN-inhibitory strategy. In other aspects, the hypoimmune cell expressing the therapeutic protein is, or is differentiated from, a HIP cell, a HIPO− cell, or overexpresses CD16, CD32, or CD64.

F. Maintenance of Pluripotent Cells

Once generated, the pluripotent cells, such as HIP, HIPO−, or CD16, CD32, or CD64 cells, can be maintained in an undifferentiated state as is known for maintaining iPSCs. For example, HIP cells are cultured on Matrigel using culture media that prevents differentiation and maintains pluripotency.

G. Differentiation of Pluripotent Cells

The invention provides pluripotent cells, such as HIP, HIPO−, or CD16, CD32, or CD64 cells, that are differentiated into different cell types for subsequent transplantation into subjects in combination with a PMN-inhibitory strategy. As will be appreciated by those in the art, the methods for differentiation depend on the desired cell type using known techniques. The cells are differentiated in suspension and then put into a gel matrix form, such as matrigel, gelatin, or fibrin/thrombin forms to facilitate cell survival. Differentiation is assayed as is known in the art, generally by evaluating the presence of cell-specific markers.

In some embodiments, the pluripotent cells are differentiated into hepatocytes to address loss of the hepatocyte functioning or cirrhosis of the liver. There are a number of techniques that can be used to differentiate HIPO− cells into hepatocytes; see for example Pettinato et al., doi:10.1038/spre32888, Snykers et al., *Methods Mol Biol* 698:305-314 (2011), Si-Tayeb et al, *Hepatology* 51:297-305 (2010) and Asgari et al., *Stem Cell Rev* (:493-504 (2013), all of which are hereby expressly incorporated by reference in their entirety and specifically for the methodologies and reagents for differentiation. Differentiation is assayed as is known in the art, generally by evaluating the presence of hepatocyte associated and/or specific markers, including, but not limited to, albumin, alpha fetoprotein, and fibrinogen. Differentiation can also be measured functionally, such as the metabolization of ammonia, LDL storage and uptake, ICG uptake and release and glycogen storage.

In some embodiments, the pluripotent cells are differentiated into beta-like cells or islet organoids for transplantation to address type I diabetes mellitus (T1DM). Cell systems are a promising way to address T1DM, see, e.g., Ellis et al., doi/10.1038/nrgastro.2017.93, incorporated herein by reference. Additionally, Pagliuca et al. reports on the successful differentiation of β-cells from hiPSCs (see doi/10.106/j.cell.2014.09.040, hereby incorporated by reference in its entirety and in particular for the methods and reagents outlined there for the large-scale production of functional human β cells from human pluripotent stem cells). Furthermore, Vegas et al. shows the production of human β cells from human pluripotent stem cells followed by encapsulation to avoid immune rejection by the host; (doi:10.1038/nm.4030, hereby incorporated by reference in its entirety and in particular for the methods and reagents outlined there for the large-scale production of functional human β cells from human pluripotent stem cells).

Differentiation is assayed as is known in the art, generally by evaluating the presence of β cell associated or specific markers, including but not limited to, insulin. Differentiation can also be measured functionally, such as measuring glucose metabolism, see generally Muraro et al, doi:10.1016/j.cels.2016.09.002, hereby incorporated by reference in its entirety, and specifically for the biomarkers outlined there.

Once the differentiated beta cells are generated, they can be transplanted (either as a cell suspension or within a gel matrix as discussed herein) into the portal vein/liver, the omentum, the gastrointestinal mucosa, the bone marrow, a muscle, or subcutaneous pouches.

In some embodiments, the pluripotent cells are differentiated into retinal pigment epithelium (RPE) to address sight-threatening diseases of the eye. Human pluripotent stem cells have been differentiated into RPE cells using the techniques outlined in Kamao et al., *Stem Cell Reports*

2014:2:205-18, hereby incorporated by reference in its entirety and in particular for the methods and reagents outlined there for the differentiation techniques and reagents; see also Mandai et al., doi:10.1056/NEJMoa1608368, also incorporated in its entirety for techniques for generating sheets of RPE cells and transplantation into patients.

Differentiation can be assayed as is known in the art, generally by evaluating the presence of RPE associated and/or specific markers or by measuring functionally. See for example Kamao et al., doi:10.1016/j.stemcr.2013.12.007, hereby incorporated by reference in its entirety and specifically for the markers outlined in the first paragraph of the results section.

In some embodiments, the pluripotent cells are differentiated into cardiomyocytes to address cardiovascular diseases. Techniques are known in the art for the differentiation of hiPSCs to cardiomyocytes and discussed in the Examples. Differentiation can be assayed as is known in the art, generally by evaluating the presence of cardiomyocyte associated or specific markers or by measuring functionally; see for example Loh et al., doi:10.1016/j.cell.2016.06.001, hereby incorporated by reference in its entirety and specifically for the methods of differentiating stem cells including cardiomyocytes.

In some embodiments, the pluripotent cells are differentiated into endothelial colony forming cells (ECFCs) to form new blood vessels to address peripheral arterial disease. Techniques to differentiate endothelial cells are known. See, e.g., Prasain et al., doi:10.1038/nbt.3048, incorporated by reference in its entirety and specifically for the methods and reagents for the generation of endothelial cells from human pluripotent stem cells, and also for transplantation techniques. Differentiation can be assayed as is known in the art, generally by evaluating the presence of endothelial cell associated or specific markers or by measuring functionally.

In some embodiments, the pluripotent cells are differentiated into thyroid progenitor cells and thyroid follicular organoids that can secrete thyroid hormones to address autoimmune thyroiditis. Techniques to differentiate thyroid cells are known the art. See, e.g. Kurmann et al., doi:10.106/j.stem.2015.09.004, hereby expressly incorporated by reference in its entirety and specifically for the methods and reagents for the generation of thyroid cells from human pluripotent stem cells, and also for transplantation techniques. Differentiation can be assayed as is known in the art, generally by evaluating the presence of thyroid cell associated or specific markers or by measuring functionally.

H. Transplantation of Differentiated Pluripotent Cells

As will be appreciated by those in the art, the differentiated pluripotent cell derivatives are transplanted using techniques known in the art that depends on both the cell type and the ultimate use of these cells. In general, the cells of the invention are transplanted either intravenously or by injection at particular locations in the patient. When transplanted at particular locations, the cells may be suspended in a gel matrix to prevent dispersion while they take hold.

In order that the invention described herein may be more fully understood, the following examples are set forth. It should be understood that these examples are for illustrative purposes only and are not to be construed as limiting this invention in any manner.

VIII. EXAMPLES

HIP, HIPO−, and CD16/CD32/CD64 cells are generated as disclosed in WO2018/132783, PCT/US19/42123, PCT/US19/42117, and Prov. Appl. Nos. 62/698,973, 62/698,978, 62/698,981, 62/698,984, 62/846,399, 62/855,499, and 62/915,601 each of which are incorporated by reference herein in their entirety.

A. Example 1: Activated Polymorphonuclear (PMN) Cells Kill Transplanted Cells Allogeneic HIP cells are killed in a pro-inflammatory environment. A comprehensive human immune assay was established using the XCelligence in vitro impedance system that obtains real-time kinetics of target cell killing. (ACEA BioSciences, San Diego, CA, Catalog No. 00380601040). Wild-type (wt) and engineered iPSCs were differentiated into endothelial cells for this assay. All components of the human immune system found in blood were included into an effector mix combining serum (contains antibodies, complement, and soluble factors like cytokines and growth factors), peripheral blood mononuclear cells (PBMCs, contains all lymphocytes, monocytes, and NK cells) and PMNs (contains mainly neutrophils and few basophils and eosinophils). Notably, the serum was taken from blood type AB donors and thus did not contain blood type antibodies. The detrimental effect of blood type antibodies has previously been established. Some experimental groups were treated with IL-2 (1 ng/ml), which is a central cytokine involved in allograft rejection. The assays were run for a duration of 90 h which is the maximum time period iECs can be cultured in this system before the monolayer breaks down spontaneously.

FIG. 3 shows that viable human wt or dKO iECs were rejected in vitro by an allogeneic effector mix containing all components of the immune system even in the absence of the pro-inflammatory cytokine IL-2. HIP cells were rejected only in the presence of IL-2. This points to the fact that HIP iECs are still susceptible to immune killing in a pro-inflammatory environment. The addition of IL-2 also accelerated killing of wt and dKO iECs. Thus, there still is a previously unidentified immune barrier for the transplantation of HIP cell derivatives.

The XCelligence assays were repeated without serum to evaluate contributions of soluble factors to the target cell killing. FIG. 4 shows that HIP cells were killed by a mixture of allogeneic PBMCs and PMNs in the presence of the proinflammatory cytokine IL-2 with similar kinetics as shown in FIG. 3. Thus, serum factors besides blood type antibodies did not affect allogeneic target cell killing if the recipient does not have preformed anti-HLA antibodies. The results conclude that HIP cells were killed by a cellular component.

Individual XCelligence assays in FIGS. 5A and 5B were run with purified CD3+ lymphocytes or NK cells (FIG. 5A) or macrophages or PMNs (FIG. 5B) to assess their individual interactions with the target cells. The assays showed that PMNs were the only cell population able to kill HIP cells, but they required inflammatory activation.

CD3+ lymphocytes killed allogeneic wt iECs but spared dKO and HIP cells; IL-2 accelerated the killing. Unstimulated NK cells exerted no killing, but IL-2 activated them to vigorously kill dKO iECs. Macrophages (Macs) needed no stimulation and very effectively killed only dKO iECs. HIP were spared by all PBMC populations. Resting PMNs did not attack any of the target cells, but IL-2 activated PMNs did kill all target cells with the same kinetics irrespective of HLA or CD47 engineering. Thus, PMNs were the only cell population that could kill the HIP cells but they required inflammatory activation.

B. Example 2: Necrotic Cells Activate PMNs and Jeopardize Transplanted Cells

The immune system not only distinguishes between "self" and "non-self", but also reacts to "danger" signals: released by autologous cells in distress. Matzinger, *Ann. Rev. Immunol.* 12:991-1045 (1994), incorporated by reference herein in its entirety. Intracellular components, released by damaged cells, can act as adjuvants and boost immune activation to alarm the immune system of cell death. Because apoptosis activates programmed cell death pathways aimed at digesting intracellular proteins, apoptotic cells are considered weak releasers of danger signals. Necrotic cells, however, release intracellular factors without prior modification and show more effective leakage of DAMPs. For our in vitro assays, 20,000 target cells were sonicated to disrupt their cell membrane and release DAMPs and the cell debris was added to prior grown and confluent target iEC layer in Xcelligence assays.

Thus, for DAMP-activated XCelligence assays, iECs were plated and in addition to the immune effector cells, 20,000 sonicated target cells were added at the same time. FIG. 6 shows that necrotic cells activated PMNs that in turn killed healthy target cells as collateral damage. All wt, dKO, and HIP iECs were killed at the same pace. When PBMCs were mixed with PMNs, the killing kinetics were slower. This was attributed to the 50% reduced PMN content in the mixed immune cell population. Overall, the results show a potent innate PMN killing mechanism that is independent of target cell immune features and is activated by the presence of necrotic cells.

Since DAMPs induce PMN activation in an attempt by the immune system to contain and clear damaged sites, healthy bystander cells are often collateral damage. Minimizing cell death after transplantation will minimize the release of DAMPs.

C. Example 3: Minimizing IL-2 Stimulation Reduces PMN Activation

Cyclosporine and dexamethasone reduced, but did not eliminate, PMN killing stimulated by IL-2 (FIG. 7). Unstimulated human PMNs did not show any killing of wt, dKO, or HIP cells (FIG. 5B) but IL-2 stimulation triggered killing. Thus, minimizing IL-2 release alleviated PMN activation. Cyclosporine and dexamethasone were analyzed for their efficacy to dampen a PMN killing response even after IL-2 stimulation. XCelligence assays were performed with human wt, dKO, and HIP cells against IL-2 stimulated human PMNs (FIG. 7). Cyclosporine was used in two different concentrations (400 ng/ml (high) and 40 ng/ml (low)). Both of these compounds showed some efficacy in reducing PMN killing induced by IL-2.

D. Example 4: Engaging PMN Inhibitory Receptors Reduce PMN Activation and Killing PMNs have several receptors that bind phosphatidylserines, phosphatidyl-ethanolamines, sialic acids, or syalylated proteins. They are abundant and cover the cell membranes. Some receptors also bind protein ligands. Such receptors signal through inhibitory ITIM or NPXY domains and include CD200R, PIRLα, and SIRL-1. PMN killing was reduced by engaging these receptors as shown below XCelligence assays.

Ligands for CD200R and PIRLα are CD200 and CD99, respectively. Recombinant human CD200 Fc chimera proteins (R&D Systems, Minneapolis, Minn., Catalog no. 2724-CD-050) and CD99 Fc chimera proteins (R&D Systems, Minneapolis, Minn., Catalog no. 3968-CD-050) engage these receptors. These Fc chimera proteins were added to the assays at 10 μg/ml. There is no known ligand for SIRL-1 but there is an activating monoclonal SIRL-1 antibody to trigger downstream inhibitory signaling (Steevels T A., *Eur J. Immunol.* 43(5):1297-308 (2013)). The human PMNs were activated via DAMPs or IL-2 and the killing of human wt and HIP iECs was assessed (FIG. 8). Engagement of either one of those inhibitory receptors prevented PMN killing in the presence of necrotic cells (sonicated cells). No receptor pathway, however, was efficient enough to fully prevent killing by IL-2 activated human PMNs although it was somewhat delayed. Thus, inhibitory receptor engagement is partially effective to inhibit PMN killing but may need to be combined with other strategies to improve efficacy.

E. Example 5: Neutrophil Elastase Inhibitors Reduce PMN Killing

The Neutrophil Elastase (NE) inhibitor BAY 85-8501 (MedChem Express, Monmouth Junction, NJ, Catalog No. HY-19908, 1 nM or 1 μM for in vitro Xcelligence assays), is a small-molecule inhibitor of high selectivity and potency that had recently been shown safety in a human clinical trial (von Nussbaum F., *Chem. Med. Chem.* 10:1163-73 (2015); Watz H., *Pulm. Pharmacol. Ther.* 2019; 56:86-93 (2019), each of which are incorporated by reference herein in their entirety). BAY 85-8501 was used at 1 nM or 1 μM concentrations. The effector PMNs were stimulated with sonicated cells or IL-2.

FIG. 9A shows that the higher concentration of BAY 85-8501 (1 μM) fully prevented human wt or HIP target cell killing when PMNs were activated via DAMPs from the necrotic (sonicated) cells. The same concentration of BAY 85-8501 further delayed the target cell killing in the presence of IL-2.

Alpha-1 antitrypsin (A1AT, Sigma-Aldrich, St. Louis, MO, Catalog No. A9024, 30 μM for in vitro Xcelligence assays), another Neutrophil Elastase inhibitor (Polverino E. *Chest.* 152(2):249-262 (2017)) was minorly effective in reducing PMN-mediated killing of human wt and HIP cells (FIG. 9B).

F. Example 6: Combination of PMN Inhibitory Receptor Engagement and Neutrophil Elastase Inhibitors The anti-SIRL-1 antibody (MyBioSource, San Diego, CA, Catalog No. MBS584764) in combination with BAY 85-8501 was a highly-potent PMN inhibitor regimen in XCelligence assays with human PMNs activated via DAMPs or IL-2 (FIG. 10).

The combination of the anti-SIRL-1 antibody and BAY 85-8501 was a tailored approach for PMN inhibition or overall immunosuppression. An XCelligence assay that combined all human immune system components PBMCs, PMNs, and serum in a pro-inflammatory IL-2 environment (FIG. 11) was used. This is a comprehensive and highly-stringent general in vitro immune assay. The combination of BAY 85-8501 and the anti-SIRL mAb was inefficient at preventing wt and dKO killing, which is known to be caused by allogeneic CD3+ lymphocytes (wt) or NK cells and Macs (dKO) from prior experiments (FIGS. 5A and B). The regimen is thus not generally immunosuppressive. It prevents only PMN killing as shown by the survival of HIP iECs, because those target cells are only killed by activated PMNs and killing is inhibited by anti-SIRL-1 and BAY 85-8501.

Figure 12:
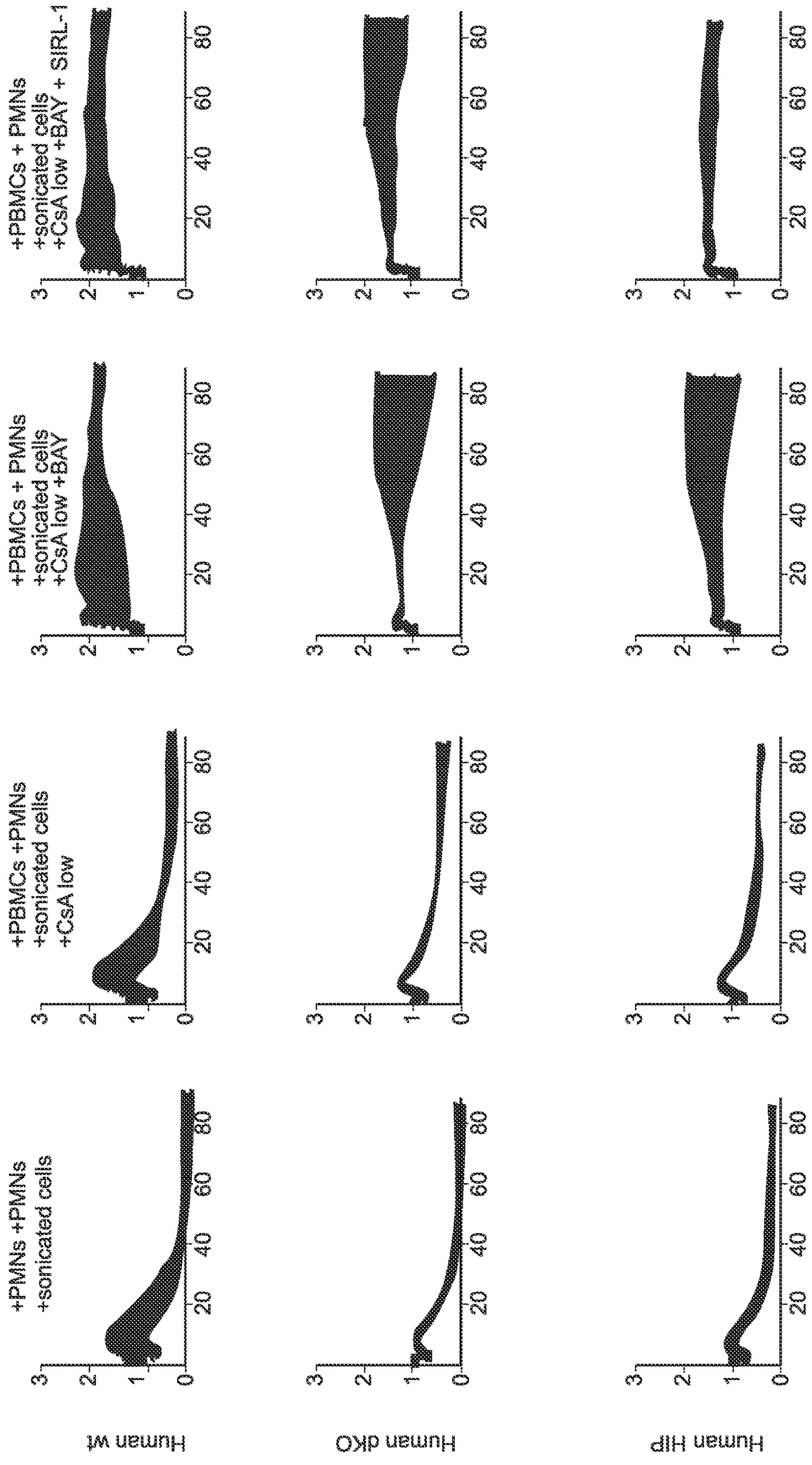

The efficacy of Cyclosporin A (CsA) combined with BAY 85-8501 was confirmed in the presence of PBMCs and DAMP-activated PMNs using the XCelligence assay (FIG. 12). Low-dose CsA (40 ng/ml) was combined with BAY 85-8501, with or without the anti-SIRL-1 mAb. The combination of low-dose CsA and BAY 85-8501 alone was highly effective in preventing killing of all target cells. CsA and BAY 85-8501 are clinically tested drugs and a translational approach into the clinic would be possible. The anti-SIRL-1 mAb is a beneficial addition to this regimen but there is no clinical grade product available at this time.

G. Example 7: PMN Killing is Diminished by Inhibiting Activating Receptors

Activating receptors include the family of toll-like receptors (TLRs) that are activated by a wide range of ligands including DAMPs. PMN activation pathways were inhibited by TAK-242 (MedChem Express, Monmouth Junction, NJ, Catalog No. HY-11109, 10 μM for in vitro Xcelligence assays), a small-molecule inhibitor of TLR-4-mediated signaling. Wild-type and HIP cells were used on the XCelligence platform using PMNs as effector cells (FIG. 13). Necrotic cells or IL-2 were used as PMN stimulators. Inhibition of TLR-4 signaling with TAK-242 diminished PMN killing. The efficacy was stronger with the somewhat weaker stimulatory signal via DAMPs. With IL-2, PMN killing was still markedly reduced.

FIG. 14 shows that PMN killing by DAMP- or IL-2 activated PMNs was mildly diminished by another inhibitor of TLR-4 signalling, Idelalisib (Idel, MedChem Express, Monmouth Junction, NJ, Catalog No. HY-13026, 10 μM for in vitro Xcelligence assays). It was similarly effective for wt and HIP iEC target cells.

FIG. 15 shows that inhibiting PMN killing by DAMP- or IL-2 activated PMNs was also diminished by CpG-52364, an inhibitor of TLR7/8/9 signaling (RayStar Biosystems, HangZhou, China, Catalog No. GY05368, 10 μM for in vitro Xcelligence assays). It was similarly effective for wt and HIP iEC target cells.

FIG. 16 shows that colchicine, an inhibitor of microtubule polymerization, was a mild inhibitor of DAMP- or IL-2 activated PMN killing (Sigma-Aldrich, St. Louis, MO, Catalog No. C9754, 1 μM for in vitro Xcelligence assays). It was again similarly effective for wt and HIP iEC target cells.

H. Example 8: PMN Killing is Diminished by Inhibiting the Release of Superoxide Apocynin is a naturally occurring methoxy-substituted catechol, experimentally used as an inhibitor of NADPH-oxidase. It can decrease the production of superoxide from activated PMNs while the ability of phagocytosis remains unaffected (Stefanska J. *Mediators Inflamm.* 2008:106507 (2008)).

FIG. 17 shows that apocynin (Apo) diminished DAMP- or IL-2 activated PMN killing (Cayman Chemical, Ann Arbor, MI, Catalog No. 11976, 10 μM for in vitro Xcelligence assays). Apocynin reduced PMN killing for wt and HIP iEC target cells.

I. Example 9: PMN Killing is Very Effectively Diminished by Combining Agents with Different Modes of Action Since PMNs are very complex effector cells that can be activated via numerous different activation pathways and can exert different killing mechanisms. The combination of drugs or approaches with different modes of action showed synergistic effects on PMN inhibition.

Colchicine was combined with either BAY 85-8501, TAK-242, or both to maximize the inhibitory effect on PMNs. FIG. 18A shows XCelligence assays with PMNs activated via DAMPs and FIG. 18B used IL-2 stimulation. All combinations very effectively and completely prevented PMN killing of wt and HIP iECs.

A multi-drug combination of idelalisib, apocynin, colchicine, BAY-85-8501, and TAK-242 in FIG. 19 did not only confirm the effective inhibition of PMN killing, it also showed that such multi-drug combinations are specific for their targets and cause no toxic target cell killing.

J. Example 10: Cell Therapy for the Treatment of Alpha1-Antitrypsin Deficiency Induced endothelial cell (iEC) grafts were used as factories to replace a crucial missing factor responsible for disease in a mouse model of alpha1-antitrypsin (A1AT) deficiency that quickly develops both structural and functional changes of lung disease. In C57BL/6 (B6) mice with quintuple Serpina1a-e knockouts, a mild lipopolysaccharide (LPS) challenge that is well tolerated in wt mice leads to emphysema development due to the unabated activity of the secreted neutrophil elastase from recruited neutrophils.

Wild type B6 mouse induced pluripotent stem cells (iPSCs) were generated and underwent gene editing to make them hypoimmunogenic. The B2m and Ciita genes were targeted for disruption with Cas9 nuclease with guides to deplete MHC class I and class II expression. CD47 was overexpressed using lentiviral transfection. The wild type and hypoimmunogenic (HIP) iPSCs were transfected to express firefly luciferase (FLuc) and were differentiated into iPSC-derived iECs. Although the HIP iPSCs were used, the emphysema model described is syngeneic.

To turn iECs into enzyme factories, HIP iECs were engineered to secrete human A1AT. The mouse Serpina1e cDNA sequence (Appendix) was synthesized, cloned into a lentiviral vector with zeocin resistance, HIP iPSC clones were transduced, and antibiotic selected pools of $HIP_{SERPINE1}$ iPSCs were expanded. These iPSCs were differentiated into $HIP_{SERPINE1}$ iECs and showed the classic EC phenotype of wt and HIP iECs (FIG. 20A). A total of $1.5\times10^5$ wt, HIP, and $HIP_{SERPINE1}$ iECs were plated for 24 h and A1AT levels were measured (FIG. 20B). The $HIP_{SERPINE1}$ iECs produced approximately 50 ng A1AT in one day.

Figure 22:
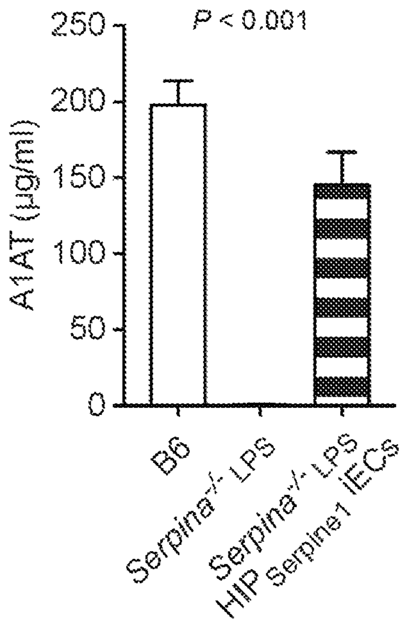

With a half-life of A1AT in mice of approx. 4.5 days, it was estimated that a cell number of $1.5\times10^8$ $HIP_{SERPINE1}$ iECs was necessary to restore and maintain physiologic A1AT serum levels (about 200 μg/ml). Seven days before induction of lung disease, $Serpina^{-/-}$ mice received $1.5\times10^8$ $HIP_{SERPINE1}$ iECs in matrigel injected into the peritoneum and the subcutaneous tissue in the lumbal area to split the cell load (FIG. 21*a*). $Serpina^{-/-}$ mice without cell injection as well as healthy B6 mice served as controls. Twenty-one days later, A1AT levels in the cell therapy group were approx. 75% of those in the healthy B6 mice and thus well in the physiologic range (FIG. 22).

Lung disease was induced in both Serpina$^{-/-}$ groups with LPS injection on day 0 (7 days after cell injection) and repeated on day 11 (FIG. 21B). On day 14, pulmonary mechanics were assessed using a computer-controlled piston ventilator for standardized measurements. Untreated Serpina$^{-/-}$ mice developed ventilation patterns consistent with developing emphysema including increased lung compliance and decreased elastance (FIG. 23). The coefficients of tissue damping and tissue elasticity were both reduced and the total lung capacity was increased. Consistent with prior reports of this model, resistance did not change. After LPS induction, all lung function parameters remained within the range of completely healthy B6 mice. Thus, $HIP_{SERPINE1}$ iEC therapy was effective in preventing the development of respiratory patterns typical of emphysematous lung disease in Serpina$^{-/-}$ mice.

The lungs were fixed for histology and serially cut for stereological assessment. Untreated B6 mice are shown in (FIG. 24). Morphometric criteria for emphysema in untreated Serpina$^{-/-}$ mice including a decrease in volume fraction of alveolar septal tissue, an increase in the fraction of alveolar volume, a decrease in surface density of alveolar septa, and an increase in the mean linear intercept (FIG. 25). $HIP_{SERPINE1}$ iEC therapy successfully prevented all structural damages to the lung tissue (FIG. 26).

Stereological lung assessment. Histology slides were scanned and assessed in a standardized way (FIG. 27). Stereological lung assessment (mean±s.d., 6 animals per group, analysis of variance (ANOVA)). Morphometric criteria for emphysema in untreated Serpina$^{-/-}$ mice were found. Parameters describing distal airspace enlargement and loss of alveoli and alveolar surface area (volume fraction of alveolar septal tissue, fraction of alveolar volume, surface density of alveolar septa), and increase in mean linear intercept (chord) length, a parameter to describe the mean free distance in the air spaces were present. $HIP_{Serpine1}$ iEC therapy was successful in preventing all structural damages to the lung tissue.

Since Serpina$^{-/-}$ mice were generated on a B6 background, allogeneic BALB/c recipients were used to separately assess graft survival. All wt B6 iEC grafts were rejected over 14 days and all $HIP_{Serpina1e}$ iEC grafts showed survival over the study period (FIG. 28). Overall, A1AT repletion via cell therapy was able to avert the development of emphysematous lung disease in Serpina$^{-/-}$ mice.

Methods

Mice: BALB/c (BALB/cAnNCrl, H2$^{d}$) and C57BL/6 (C57BL/6J, H2$^{b}$) (all 6-12 weeks) were purchased from The Jackson Laboratory (Sacramento, CA). Serpina$^{-/-}$ mice were generated by Christian Mueller as reported previously. Borel et al., *Proc Natl Acad Sci USA* 115:2788-2793 (2018), incorporated by reference herein in its entirety. The number of animals per experimental group is presented in each figure. Mice received humane care in compliance with the Guide for the Principles of Laboratory Animals. Animal experiments were approved by the University of California San Francisco (UCSF) Institutional Animal Care and Use Committee and performed according to local guidelines.

Mouse iPSC culture: Mouse iPSCs were generated from tail tip fibroblasts as reported previously[2]. On confluent MEF feeder cells, iPSCs were grown in KO DMEM 10829 with 15% KO Serum Replacement, 1% glutamine, 1% MEM-NEAA, 1% pen-strep (all Gibco, Grand Island, NY), 0.2% beta-mercaptoethanol, and 100 units LIF (both Millipore, Billerica, MA). Cells were maintained in 10 cm dishes and medium was changed daily. Cells were passaged every 2-3 days using 0.05% trypsin-EDTA (Gibco). Prior to experiments, iPSCs were cultured on gelatin (Millipore, Billerica, Mass.) without feeders using the standard media. Cell cultures were regularly screened for mycoplasma infections using the MycoAlert Kit (Lonza, Basel, Switzerland). Gene editing was performed as described previously[2].

Transduction to express firefly luciferase: One hundred thousand iPSCs were plated in gelatin coated 6-well plates and incubated overnight at 37° C. at 5% $CO_2$. Media was then changed and one vial of Fluc lentiviral particles expressing luciferase II gene under re-engineered EF1a promotor (GenTarget, San Diego, CA) was added to 1.5 ml media. After 36 h, 1 ml of cell media was added. After further 24 h, complete media change was performed. After 2 days, luciferase expression was confirmed by adding D-luciferin (Promega, Madison, WI). Signals were quantified with IVIS 200 (Perkin Elmer Waltham, MA) in maximum photons $s^{-1}$ $cm^{-2}$ per steradian.

Derivation and characterization of iPSC-derived endothelial cells (iECs): iPSC were plated on gelatin in 6-well plates and maintained in mouse iPSC media until they reached 60% confluency. To start the differentiation, media was changed to RPMI-1640 containing 2% B-27 minus Insulin (both Gibco, Grand Island, NY) and 5 μM CHIR-99021 (Selleckchem, Munich, Germany). On day 2, the media was changed to reduced media: RPMI-1640 containing 2% B-27 minus Insulin (both Gibco) and 2 μM CHIR-99021 (Selleckchem, Munich, Germany). From day 4 to day 7, cells were exposed to RPMI-1640 EC media, RPMI-1640 containing 2% B-27 minus Insulin plus 50 ng/mL mouse vascular endothelial growth factor (mVEGF; R&D Systems, Minneapolis, MN), 10 ng/mL mouse fibroblast growth factor basic (mFGFb; R&D Systems), 10 μM Y-27632 (Sigma-Aldrich, Saint Louis, MO), and 1 μM SB 431542 (Sigma-Aldrich). Endothelial cell clusters were visible from day 7 and cells were maintained in EGM-2 SingleQuots media (Lonza, Basel, Switzerland) plus 10% FCS hi (Gibco), 25 ng/mL mVEGF, 2 ng/mL mFGFb, 10 μM Y-27632 (Sigma-Aldrich), and 1 μM SB 431542. The differentiation process was completed after 21 days and undifferentiated cells detached during the differentiation process. For purification, cells went through MACS purification according the manufactures' protocol using anti-CD15 mAb-coated magnetic microbeads (Miltenyi, Auburn, CA) for negative selection. The highly purified miECs in the flow-through were cultured in EGM-2 SingleQuots media plus supplements and 10% FCS hi. TrypLE was used for passaging the cells 1:3 every 3 to 4 days. Their phenotype was confirmed by immunofluorescence (IF) for CD31 (ab28364, Abcam), and VE-cadherin (sc-6458, Santa Cruz Biotechnology, Santa Cruz, CA). Briefly, cells were fixed with 4% paraformaldehyde in PBS for 15 min. Cell membranes were permeabilized with Permeabilization solution (ASB-0102, Applied StemCell, Milpitas, CA), followed by Blocking solution (ASB-0103, Applied StemCell) and incubation with the primary antibodies. For visualization, cells were incubated with secondary antibody conjugated with AF488 or AF555 (Invitrogen, Carlsbad, CA). After nuclei staining with DAPI, images were obtained and analyzed with a Leica SP5 laser confocal microscope (Leica, Wetzlar, Germany). For the tube formation assay, $2.5\times10^{5}$ iECs were stained with 5 μM CFSE and 0.1 μg/mL Hoechst (both Thermo Fisher, Waltham, MA) for 10 min at RT and plated on 10 mg/mL undiluted Matrigel (356231, Corning, Corning, NY) in 24-well plates. After 48 h, tube formations were visualized by IF. PCR was performed as described above. The following primers were used: VE-cadherin (Cdh5): forward: 5'-GGATGCAGAGGCTCACAGAG-3' (SEQ ID NO: 18, reverse: 5'-CTGGCGGTTCACGTTGGACT-3' (SEQ ID NO: 19). All other primers were included in the Mouse ES/iPS cell Pluripotency RT-PCR Kit (Cat #ASK-6001, Applied StemCell).

Gene editing to generate $HIP_{Serpina1e}$ iPSCs: the Serpina1e gene sequence (NM_009247.2) was synthesized and cloned into a lentivirus with zeocin resistance, which was used to transduce HIP iPSCs, followed by antibiotic selection and expansion of $HIP_{Serpina1e}$ iPSCs. Clones were picked and expanded and their Serpina1e mRNA levels were quantified. Of 3 clones with stably high Serpina1e expression and confirmed pluripotency markers Nanog, Oct4, and Sox2, the clone with the highest Serpina1e expression was chosen for this study.

Graft survival by BLI: D-luciferin firefly potassium salt (375 mg/kg; Biosynth AG, Staad, Switzerland) was dissolved in PBS (pH 7.4) (Gibco, Invitrogen) and was injected i.p. (250 μL per mouse) into anesthetized mice. Animals were imaged using the Ami HT system (Spectral Instruments Imaging). Region of interest (ROI) bioluminescence was quantified in units of maximum photons $s^{-1}$ $cm^{-2}$ per steradian. The maximum signal from an ROI was measured using Aura Image software (Spectral Instruments Imaging, Tucson, AZ).

Mouse lung emphysema model: B6 or $Serpina^{-/-}$ mice received two sequential orotracheal doses of LPS to induce lung disease. Mice were anesthetized with an i.p. dose of a ketamine/xylazine mixture (90 mg/kg of ketamine and 4.5 mg/kg of xylazine) and were placed in dorsal recumbency on a rodent work stand (Braintree Scientific, Braintree, MA) and intubated. Following instillation, mice received three ventilations with 0.2 mL of air.

FlexiVent: Mice were anesthetized as outlined above. A tracheotomy was performed and a pre-calibrated cannula was introduced into the trachea. The mouse was then placed on a computer-controlled piston-ventilator flexiVent system (Scireq, Montreal, Canada) and ventilated at a tidal volume of 10 mL/kg, rate of 150 breaths per minute and a positive end expiratory pressure of 3 mmHg. Neuromuscular blockade with pancuronium bromide (2.5 mg/kg) was given to prevent spontaneous respiratory effort. Measurements were obtained as previously described.

Lung stereology: Immediately following measurements of lung mechanics (flexiVent), lungs were harvested for stereologic analysis. The chest was opened, and the pulmonary circulation flushed via right ventricular puncture with 10 mL cold PBS. The degassed lung was inflated with 1% ultra-low temperature gel agarose (Sigma-Aldrich) in neutral buffered formalin (10%) to 25 cm pressure. Once fixed, lung volume was measure by water displacement. Subsequently, lung tissues were oriented randomly in cassettes and embedded in paraffin, followed by sectioning started at random depth at a uniform thickness (10 μm). Slides were stained with hematoxylin and eosin and 10 randomly oriented nonoverlapping fields from each section were photographed. Lung morphology was quantified using the Stepanizer software (www.stepanizer.com). Surrogate markers for lung morphology were calculated as follows: Volume fraction of alveolar septal tissue:

$$Vv(sept/par)=\Sigma P(sept)/\Sigma P(par),$$

Fraction of Alveolar Volume:

$$Vv(alv/par)=\Sigma P(alv)/\Sigma P(par)$$

Surface Density of Alveolar Septa:

$$Sv(sept/par)=(2\times\Sigma I)/\Sigma P(par)\times l/p)$$

Mean Linear Intercept:

$$Lm=2\cdot k\cdot d\cdot P(asp)/I(A).$$

K. Example 11: PMN Inhibition Promotes Human HIP $iEC_{SERPINA1}$ Survival

Human HIP iPSCs were differentiated into HIP iECs. Using lentiviral particles, plasmids carrying the SERPINA1 cDNA were introduced into HIP iECs for the generation of HIP $iEC_{SERPINA1}$. A clone with high SERPINA1 expression was picked for XCelligence assays. FIG. 29 shows that HIP $iEC_{SERPINA1}$ were not killed after incubation with unstimulated PMNs but did so when the PMNs were stimulated with either sonicated target cells or IL-2. This confirms that cell products are at risk of PMN killing after transplantation when cells die and release DAMPs or trigger some inflammatory environment.

Four different PMN inhibitory strategies were tested for their efficacy to prevent target cell killing by activated PMNs. The regimens CpG-52364+colchicine and TAK-242+BAY 85-8501 (FIG. 30) as well as CpG-52364+BAY 85-8501 and Idelalisib+Apocynin+colchicine (FIG. 31) showed that PMN killing was effectively inhibited.

Methods

Human HIP iPSC differentiation into HIP iECs: Human gene edited HIP iPSC were plated on diluted Matrigel (356231, Corning) in 6-well plates and maintained in Essential 8 Flex media (Thermo Fisher Scientific, Carlsbad, CA). The differentiation was started at 60% confluency, and media was changed to RPMI-1640 containing 2% B-27 minus insulin (both Gibco) and 5 μM CHIR-99021 (Selleckchem). On day 2, the media was changed to reduced media: RPMI-1640 containing 2% B-27 minus insulin (Gibco) and 2 μM CHIR-99021 (Selleckchem). From day 4 to day 7, cells were exposed to RPMI-1640 EC media, RPMI-1640 containing 2% B-27 minus insulin plus 50 ng/mL human vascular endothelial growth factor (VEGF; R&D Systems), 10 ng/mL human fibroblast growth factor basic (FGFb; R&D Systems), 10 μM Y-27632 (Sigma-Aldrich), and 1 μM SB 431542 (Sigma-Aldrich). Endothelial cell clusters were visible from day 7 and cells were maintained in EGM-2 SingleQuots media (Lonza) plus 10% FCS hi (Gibco), 25 ng/mL VEGF, 2 ng/mL FGFb, 10 μM Y-27632 (Sigma-Aldrich), and 1 μM SB 431542 (Sigma-Aldrich). The differentiation process was completed after 14 days and undifferentiated cells detached during the differentiation process. For purification, cells were treated with 20 μM PluriSln-1 (StemCell Technologies, Vancouver, BC, Canada) for 48 h. The highly purified HIP iECs were cultured in EGM-2 SingleQuots media (Lonza) plus supplements and 10% FCS hi (Gibco). TrypLE Express was used for passaging the cells 1:3 every 3 to 4 days.

Lentiviral overexpression of SERPINA1: HIP iECs were transduced with lentiviral particles carrying a plasmid with the Serpina1 cDNA (RC202082L2V, Origene, Rockville, MD). The pool of cells was expanded and clones were picked and clonally expanded. The clone with the highest SERPINA1 mRNA expression was chosen.

IX. EXEMPLARY SEQUENCES

SEQ ID NO:1 - Human β-2-Microglobulin
MSRSVALAVLALLSLSGLEAIQRTPKIQVYSRHPAENGKSNFLNCYVSG
FHPSDIEVDLLKNGERIEKVEHSDLSFSKDWSFYLLYYTEFTPTEKDEY
ACRVNHVTLSQPKIVKWDRDI SEQ ID NO:2 - Human CIITA protein, 160 amino acid N-terminus
MRCLAPRPAGSYLSEPQGSSQCATMELGPLEGGYLELLNSDADPLCLYH
FYDQMDLAGEEEIELYSEPDTDTINCDQFSRLLCDMEGDEETREAYANI
AELDQYVFQDSQLEGLSKDIFKHIGPDEVIGESMEMPAEVGQKSQKRPF
PEELPADLKHWKP SEQ ID NO:3 - Human CD47
MWPLVAALLLGSACCGSAOLLFNKTKSVEFTFCNDTVVIPCFVTNMEAQ
NTTEVYVKWKFKGRDIYTFDGALNKSTVPTDFSSAKIEVSQLLKGDASL
KMDKSDAVSHTGNYTCEVTELTREGETIIELKYRVVSWFSPNENILIVI
FPIFAILLFWGQFGIKTLKYRSGGMDEKTIALLVAGLVITVIVIVGAIL
FVPGEYSLKNATGLGLIVTSTGILILLHYYVFSTAIGLTSFVIAILVIQ
VIAYILAVVGLSLCIAACIPMHGPLLISGLSILALAQLLGLVYMKFVE SEQ ID NO:4 - Herpes Simplex Virus Thimidine Kinase (HSV-tk)
MASYPCHQHASAFDQAARSRGHSNRRTALRPRRQQEATEVRLEQKMPTL
LRVYIDGPHGMGKTTTTQLLVALGSRDDIVYVPEPMTYWQVLGASETIA
NIYTTQHRLDQGEISAGDAAWMTSAQITMGMPYAVTDAVLAPHVGGEAG
SSHAPPPALTLIFDRHPIAALLCYPAARYLMGSMTPQAVLAFVALIPPT
LPGTNIVLGALPEDRHIDRLAKRQRPGERLDLAMLAAIRRVYGLLANTV
RYLQGGGSWWEDWGQLSGTAVPPQGAEPQSNAGPRPHIGDTLFTLFRAP
ELLAPNGDLYNVFAWALDVLAKRLRPMHVFILDYDQSPAGCRDALLQLT
SGMVQTHVTTPGSIPTICDLARTFAREMGEAN SEQ ID NO:5 - *Escherichia coli* Cytosine Deaminase (EC-CD)
MSNNALQTIINARLPGEEGLWQIHLQDGKISAIDAQSGVMPITENSLDA
EQGLVIPPFVEPHIHLDTTQTAGQPNWNQSGTLFEGIERWAERKALLTH
DDVKQRAWQTLKWQIANGIQHVRTHVDVS DATLTALKAMLEVKQEVAP
WIDLQIVAFPQEGILSYPNGEALLEEALRLGADVVGAIPHFEFTREYGV
ESLHKTFALAQKYDRLIDVHCDEIDDEQSRFVETVAALAHHEGMGARVT
ASHTTAMHSYNGAYTSRLFRLLKMSGINFVANPLVNIHLQGRFDTYPKR
RGITRVKEMLESGINVCFGHDDVFDPWYPLGTANMLQVLHMGLHVCQLM
GYGQINDGLNLITHHSARTLNLQDYGIAAGNSANLIILPAENGFDALRR
QVPVRYSVRGGKVIASTQPAQTTVYLEQPEAIDYKR SEQ ID NO:6 - Truncated human Caspase 9
GFGDVGALESLRGNADLAYILSMEPCGHCLIINNVNFCRESGLRTRTGS
NIDCEKLRRRFSSLHFMVEVKGDLTAKKMVLALLELAQQDHGALDCCVV
VILSHGCQASHLQFPGAVYGTDGCPVSVEKIVNIFNGTSCPSLGGKPKL
FFIQACGGEQKDHGFEVASTSPEDESPGSNPEPDATPFQEGLRTFDQLD
AISSLPTPSDIFVSYSTFPGFVSWRDPKSGSWYVETLDDIFEQWAHSED
LQSLLLRVANAVSVKGIYKQMPGCFNFLRKKLFFKTS SEQ ID NO:7 - Human CD64
NM_000566
MWFLTTLLLWVPVDGQVDTTKAVITLQPPWVSVFQEETVTLHCEVLHLP
GSSSTQWFLNGTATQTSTPSYRITSASVNDSGEYRCQRGLSGRSDPIQL
EIHRGWLLLQVSSRVFTEGEPLALRCHAWKDKLVYNVLYYRNGKAFKFF
HWNSNLTILKTNISHNGTYHCSGMGKHRYTSAGISVTVKELFPAPVLNA
SVTSPLLEGNLVTLSCETKLLLQRPGLQLYFSFYMGSKTLRGRNTSSEY
QILTARREDSGLYWCEAATEDGNVLKRSPELELQVLGLQLPTPVWFHVL
FYLAVGIMFLVNTVLWVTIRKELKRKKKWDLEISLDSGHEKKVISSLQE
DRHLEEELKCQEQKEEQLQEGVHRKEPQGAT SEQ ID NO:8 - Human CD52
NM_001803
MKRFLFLLLTISLLVMVQIQTGLSGQNDTSQTSSPSASSNISGGIFLFF
VANAIIHLFCFS SEQ ID NO:9 - Human CD16 FCGR3A
NM_001803
MAEGTLWQILCVSSDAQPQTFEGVKGADPPTLPPGSFLPGPVLWWGSLA
RLQTEKSDEVSRKGNWWVTEMGGGAGERLFTSSCLVGLVPLGLRISLVT
CPLQCGIMWQLLLPTALLLLVSAGMRTEDLPKAVVFLEPQWYRVLEKDS
VTLKCQGAYSPEDNSTQWFHNESLISSQASSYFIDAATVDDSGEYRCQT
NLSTLSDPVQLEVHIGWLLLQAPRWVFKEEDPIHLRCHSWKNTALHKVT
YLQNGKGRKYFHHNSDFYIPKATLKDSGSYFCRGLFGSKNVSSETVNIT
ITQGLAVSTISSEFPPGYQVSFCLVMVLLFAVDTGLYFSVKTNIRSSTR
DWKDHKFKWRKDPQDK -continued SEQ ID NO: 10 - Human CD16 FCGR3B
NM_001803
MWQLLLPTALLLLVSAGMRTEDLPKAVVFLEPQWYSVLEKDSVTLKCQG
AYSPEDNSTQWFHNENLISSQASSYFIDAATVNDSGEYRCQTNLSTLSD
PVQLEVHIGWLLLQAPRWVFKEEDPIHLRCHSWKNTALHKVTYLQNGKD
RKYFHHNSDFHIPKATLKDSGSYFCRGLVGSKNVSSETVNITITQGLAV
STISSFSPPGYQVSFCLVMVLLFAVDTGLYFSVKTNI SEQ ID NO: 11 - Human CD32 FCGR2A
NM_001803
MTMETQMSQNVCPRNLWLLQPLTVLLLLASADSQAAAPPKAVLKLEPPW
INVLQEDSVTLTCQGARSPESDSIQWFHNGNLIPTHTQPSYRFKANNND
SGEYTCQTGQTSLSDPVHLTVLSEWLVLQTPHLEFQEGETIMLRCHSWK
DKPLVKVTFFQNGKSQKFSHLDPTFSIPQANHSHSGDYHCTGNIGYTLF
SSKPVTITVQVPSMGSSSPMGIIVAVVIATAVAAIVAAVVALIYCRKKR
ISANSTDPVKAAQFEPPGRQMIAIRKRQLEETNNDYETADGGYMTLNPR
APTDDDKNIYLTLPPNDHVNSNN SEQ ID NO: 12 - Human CD32 FCGR2B
NM_001803
MGILSFLPVLATESDWADCKSPQPWGHMLLWTAVLFLAPVAGTPAAPPK
AVLKLEPQWINVLQEDSVTLTCRGTHSPESDSIQWFHNGNLIPTHTQPS
YRFKANNNDSGEYTCQTGQTSLSDPVHLTVLSEWLVLQTPHLEFQEGET
IVLRCHSWKDKPLVKVTFFQNGKSKKFSRSDPNFSIPQANHSHSGDYHC
TGNIGYTLYSSKPVTITVQAPSSSPMGIIVAVVTGIAVAAIVAAVVALI
YCRKKRISALPGYPECREMGETLPEKPANPTNPDEADKVGAENTITYSL
LMHPDALEEPDDQNRI SEQ ID NO: 13 - Human CD32 FCGR2C
NM_001803
MGILSFLPVLATESDWADCKSPQPWGHMLLWTAVLFLAPVAGTPAAPPK
AVLKLEPQWINVLQEDSVTLTCRGTHSPESDSIPWFHNGNLIPTHTQPS
YRFKANNNDSGEYTCQTGQTSLSDPVHLTVLSEWLVLQTPHLEFQEGET
IVLRCHSWKDKPLVKVTFFQNGKSKKFSRSDPNFSIPQANHSHSGDYHC
TGNIGYTLYSSKPVTITVQAPSSSPMGIIVAVVTGIAVAAIVAAVVALI
YCRKKRISANSTDPVKAAQFEPPGRQMIAIRKRQPEETNNDYETADGGY
MTLNPRAPTDDDKNIYLTLPPNDHVNSNN SEQ ID NO: 14 - Human CD99
NP_002405.1
MARGAALALL LFGLLGVLVA APDGGFDLSD ALPDNENKKP
TAIPKKPSAG DDFDLGDAVV DGENDDPRPP NPPKPMPNPN
PNHPSSSGSF SDADLADGVS GGEGKGGSDG GGSHRKEGEE
ADAPGVIPGI VGAVVVAVAG AISSFIAYQK KKLCFKENAE
QGEVDMESHR NANAEPAVQR TLLEK SEQ ID NO: 15 - Human CD200
NP_001352780.1
MERLVIRMPF SHLSTYSLVW VMAAVVLCTA QVQWTQDER
EQLYTPASLK CSLQNAQEAL IVTWQKKKAV SPENMVTFSE
NHGWIQPAY KDKINITQLG LQNSTITFWN ITLEDEGCYMC
LFNTFGFGK ISGTACLTVY VQPIVSLHYK FSEDHLNITC
SATARPAPMV FWKVPRSGIENSTVTLSHPN GTTSVTSILH
IKDPKNQVGK EVICQVLHLG TVTDFKQTVN KGYWFSVPLL
LSIVSLVILL VLISILLYWK RHRNQDRGEL SQGVQKMT SEQ ID NO:16 - Murine Alpha-1 Antitrypsin (AIAT) >NP_033273.1 alpha-1-antitrypsin 1-5 precursor [Mus musculus]
MTPSISWCLLLLAGLCCLVPSFLAEDVQETDTSQKDQSPASHEIATNLG
DFAISLYRELVHQSNTSNIFFSPVSIATAFAMLSLGSKGDTHTQILEGL
QFNLTQTSEADIHNSFQHLLQTLNRPDSELQLSTGNGLFVNNDLKLVEK
FLEEAKNHYQAEVFSVNFAESEEAKKVINDFVEKGTQGKIVEAVKKLEQ
DTVFVLANYILFKGKWKKPFDPENTKQAEFHVDESTTVKVPMMTLSGML
DVHHCSTLSSWVLLMDYAGNATAVFLLPDDGKMQHLEQTLNKELISKFL
LNRRRRLAQIHIPRLSISGNYNLETLMSPLGITRIFNSGADLSGITEEN
APLKLSQAVHKAVLTIDETGTEAAAATVLQGGFLSMPPILHFNRPFLFI
IFEEHSQSPLFVGKVVDPTHK SEQ ID NO:17 - Human Alpha-1 Antitrypsin (AIAT) >NP_001002236.1 alpha-1-antitrypsin precursor [Homo sapiens]
MPSSVSWGILLLAGLCCLVPVSLAEDPQGDAAQKTDTSHHDQDHPTFNK
ITPNLAEFAFSLYRQLAHQSNSTNIFFSPVSIATAFAMLSLGTKADTHD
EILEGLNFNLTEIPEAQIHEGFQELLRTLNQPDSQLQLTTGNGLFLSEG
LKLVDKFLEDVKKLYHSEAFTVNFGDTEEAKKQINDYVEKGTQGKIVDL
VKELDRDTVFALVNYIFFKGKWERPFEVKDTEEEDFHVDQVTTVKVPMM
KRLGMFNIQHCKKLSSWLLMKYLGNATAIFFLPDEGKLQHLENELTHDI -continued

```
ITKFLENEDRRSASLHLPKLSITGTYDLKSVLGQLGITKVFSNGADLSG
VTEEAPLKLSKAVHKAVLTIDEKGTEAAGAMFLEAIPMSIPPEVKFNKP
FVFLMIEONTKSPLF
```

All publications and patent documents disclosed or referred to herein are incorporated by reference in their entirety. The foregoing description has been presented only for purposes of illustration and description. This description is not intended to limit the invention to the precise form disclosed. It is intended that the scope of the invention be defined by the claims appended hereto.

What is claimed:

1. A pharmaceutical composition, comprising a modified therapeutic cell, comprising an increased cell surface CD200 receptor (CD200R) ligand and cell surface CD99 receptor (CD99R) ligand when compared to an equivalent therapeutic cell that has not been modified, wherein said modified therapeutic cell comprises:

a. a reduced or eliminated cell-surface Major Histocompatibility Antigen Class I (MHC-I) when compared to said equivalent therapeutic cell that has not been modified;

b. a reduced or eliminated cell-surface Major Histocompatibility Antigen Class II MHC-II) when compared to said equivalent therapeutic cell that has not been modified; and c. an increased CD47 expression from a transgene or from a modified chromosomal expression sequence when compared to said equivalent therapeutic cell that has not been modified;

wherein said CD200R ligand is a polymorphonuclear cell (PMN) inhibitor.

2. The pharmaceutical composition of claim 1, wherein said modified therapeutic cell is a pancreatic islet cell that was differentiated from a hypoimmune pluripotent (HIP) cell that is ABO blood group O and Rhesus Factor negative (HIPO−) wherein said therapeutic cell retains a reduced or eliminated cell-surface MHC-I, reduced or eliminated cell-surface MHC-II, and increased CD47 expression.

3. The pharmaceutical composition of claim 1, wherein said modified therapeutic cell is a pancreatic islet cell.

4. The pharmaceutical composition of claim 1, wherein said modified therapeutic cell is human.

5. The pharmaceutical composition of claim 1, wherein said modified therapeutic cell is from a pig.

6. The pharmaceutical composition of claim 1, wherein said CD200R ligand has at least 90% sequence identity with SEQ ID NO:15.

7. The pharmaceutical composition of claim 6, wherein said CD200R ligand has the sequence of SEQ ID NO:15.

8. The pharmaceutical composition of claim 1, wherein said CD99R ligand has at least 90% sequence identity with SEQ ID NO: 14.

9. The pharmaceutical composition of claim 8, wherein said CD99R ligand has the sequence of SEQ ID NO:14.

10. The pharmaceutical composition of claim 1, wherein said modified therapeutic cell is ABO blood group type O and Rhesus factor negative (Rh−).

11. The pharmaceutical composition of claim 1, wherein said modified therapeutic cell is a chimeric antigen receptor (CAR) cell, an endothelial cell, a dopaminergic neuron, a cardiomyocyte, or a retinal pigment endothelium cell.

12. The pharmaceutical composition of claim 1, wherein said modified therapeutic cell is derived or differentiated from a hypoimmune cell, a hypoimmune pluripotent (HIP) cell, a hypoimmune or HIP cell that is AB blood group O, a Rhesus Factor negative (Rh−) cell, a hypoimmune or HIP cell that is blood group O and Rh−, an induced pluripotent stem cell (iPSC), or an embryonic stem cell (ESC) wherein said therapeutic cell retains a reduced or eliminated cell-surface MHC-I, reduced or eliminated cell-surface MHC-II, and increased CD47 expression.

13. The pharmaceutical composition of claim 1, further comprising a CD64 molecule on its cell surface.

14. The pharmaceutical composition of claim 1, wherein said modified therapeutic cell is differentiated from a hypoimmune pluripotent (HIP) cell, a HIP cell that is AB blood group O, an induced pluripotent stem cell (iPSC), or an embryonic stem cell (ESC).

15. The pharmaceutical composition of claim 1, wherein said modified therapeutic cell is from a species selected from the group consisting of a monkey, cow, pig, chicken, turkey, horse, sheep, goat, donkey, mule, duck, goose, buffalo, camel, yak, llama, alpaca, mouse, rat, dog, cat, hamster, and guinea pig.

* * * * *

```
                         SEQUENCE LISTING


<160> NUMBER OF SEQ ID NOS: 19

<210> SEQ ID NO 1
<211> LENGTH: 119
<212> TYPE: PRT
<213> ORGANISM: Homo sapiens

<400> SEQUENCE: 1

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Ile
        115


<210> SEQ ID NO 2
<211> LENGTH: 160
<212> TYPE: PRT
<213> ORGANISM: Homo sapiens

<400> SEQUENCE: 2

Met Arg Cys Leu Ala Pro Arg Pro Ala Gly Ser Tyr Leu Ser Glu Pro
1               5                   10                  15

Gln Gly Ser Ser Gln Cys Ala Thr Met Glu Leu Gly Pro Leu Glu Gly
            20                  25                  30

Gly Tyr Leu Glu Leu Leu Asn Ser Asp Ala Asp Pro Leu Cys Leu Tyr
        35                  40                  45

His Phe Tyr Asp Gln Met Asp Leu Ala Gly Glu Glu Glu Ile Glu Leu
    50                  55                  60

Tyr Ser Glu Pro Asp Thr Asp Thr Ile Asn Cys Asp Gln Phe Ser Arg
65                  70                  75                  80

Leu Leu Cys Asp Met Glu Gly Asp Glu Glu Thr Arg Glu Ala Tyr Ala
                85                  90                  95

Asn Ile Ala Glu Leu Asp Gln Tyr Val Phe Gln Asp Ser Gln Leu Glu
            100                 105                 110

Gly Leu Ser Lys Asp Ile Phe Lys His Ile Gly Pro Asp Glu Val Ile
        115                 120                 125

Gly Glu Ser Met Glu Met Pro Ala Glu Val Gly Gln Lys Ser Gln Lys
    130                 135                 140

Arg Pro Phe Pro Glu Glu Leu Pro Ala Asp Leu Lys His Trp Lys Pro
```

```
145                 150                 155                 160


<210> SEQ ID NO 3
<211> LENGTH: 293
<212> TYPE: PRT
<213> ORGANISM: Homo sapiens

<400> SEQUENCE: 3

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Glu
    290


<210> SEQ ID NO 4
<211> LENGTH: 376
<212> TYPE: PRT
<213> ORGANISM: Human alphaherpesvirus 1

<400> SEQUENCE: 4

Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
```

-continued

```
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Val Gly
    130                 135                 140

Gly Glu Ala Gly Ser Ser His Ala Pro Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Trp
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375


<210> SEQ ID NO 5
<211> LENGTH: 427
<212> TYPE: PRT
<213> ORGANISM: Escherichia coli

<400> SEQUENCE: 5

Met Ser Asn Asn Ala Leu Gln Thr Ile Ile Asn Ala Arg Leu Pro Gly
1               5                   10                  15
```

```
Glu Glu Gly Leu Trp Gln Ile His Leu Gln Asp Gly Lys Ile Ser Ala
            20                  25                  30

Ile Asp Ala Gln Ser Gly Val Met Pro Ile Thr Glu Asn Ser Leu Asp
        35                  40                  45

Ala Glu Gln Gly Leu Val Ile Pro Pro Phe Val Glu Pro His Ile His
    50                  55                  60

Leu Asp Thr Thr Gln Thr Ala Gly Gln Pro Asn Trp Asn Gln Ser Gly
65                  70                  75                  80

Thr Leu Phe Glu Gly Ile Glu Arg Trp Ala Glu Arg Lys Ala Leu Leu
                85                  90                  95

Thr His Asp Asp Val Lys Gln Arg Ala Trp Gln Thr Leu Lys Trp Gln
            100                 105                 110

Ile Ala Asn Gly Ile Gln His Val Arg Thr His Val Asp Val Ser Asp
        115                 120                 125

Ala Thr Leu Thr Ala Leu Lys Ala Met Leu Glu Val Lys Gln Glu Val
    130                 135                 140

Ala Pro Trp Ile Asp Leu Gln Ile Val Ala Phe Pro Gln Glu Gly Ile
145                 150                 155                 160

Leu Ser Tyr Pro Asn Gly Glu Ala Leu Leu Glu Glu Ala Leu Arg Leu
                165                 170                 175

Gly Ala Asp Val Val Gly Ala Ile Pro His Phe Glu Phe Thr Arg Glu
            180                 185                 190

Tyr Gly Val Glu Ser Leu His Lys Thr Phe Ala Leu Ala Gln Lys Tyr
        195                 200                 205

Asp Arg Leu Ile Asp Val His Cys Asp Glu Ile Asp Asp Glu Gln Ser
    210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
                245                 250                 255

Ala Tyr Thr Ser Arg Leu Phe Arg Leu Leu Lys Met Ser Gly Ile Asn
            260                 265                 270

Phe Val Ala Asn Pro Leu Val Asn Ile His Leu Gln Gly Arg Phe Asp
        275                 280                 285

Thr Tyr Pro Lys Arg Arg Gly Ile Thr Arg Val Lys Glu Met Leu Glu
    290                 295                 300

Ser Gly Ile Asn Val Cys Phe Gly His Asp Asp Val Phe Asp Pro Trp
305                 310                 315                 320

Tyr Pro Leu Gly Thr Ala Asn Met Leu Gln Val Leu His Met Gly Leu
                325                 330                 335

His Val Cys Gln Leu Met Gly Tyr Gly Gln Ile Asn Asp Gly Leu Asn
            340                 345                 350

Leu Ile Thr His His Ser Ala Arg Thr Leu Asn Leu Gln Asp Tyr Gly
        355                 360                 365

Ile Ala Ala Gly Asn Ser Ala Asn Leu Ile Ile Leu Pro Ala Glu Asn
    370                 375                 380

Gly Phe Asp Ala Leu Arg Arg Gln Val Pro Val Arg Tyr Ser Val Arg
385                 390                 395                 400

Gly Gly Lys Val Ile Ala Ser Thr Gln Pro Ala Gln Thr Thr Val Tyr
                405                 410                 415

Leu Glu Gln Pro Glu Ala Ile Asp Tyr Lys Arg
            420                 425
```

<210> SEQ ID NO 6
<211> LENGTH: 282
<212> TYPE: PRT
<213> ORGANISM: Homo sapiens

<400> SEQUENCE: 6

```
Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Gln Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
    210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
        275                 280
```

<210> SEQ ID NO 7
<211> LENGTH: 374
<212> TYPE: PRT
<213> ORGANISM: Homo sapiens

<400> SEQUENCE: 7

```
Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
```

```
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
    370


<210> SEQ ID NO 8
<211> LENGTH: 61
<212> TYPE: PRT
<213> ORGANISM: Homo sapiens

<400> SEQUENCE: 8

Met Lys Arg Phe Leu Phe Leu Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Ala Ser Ser Asn Ile Ser Gly Gly Ile Phe Leu Phe
        35                  40                  45
```

```
Phe Val Ala Asn Ala Ile Ile His Leu Phe Cys Phe Ser
    50                  55                  60


<210> SEQ ID NO 9
<211> LENGTH: 359
<212> TYPE: PRT
<213> ORGANISM: Homo sapiens

<400> SEQUENCE: 9

Met Ala Glu Gly Thr Leu Trp Gln Ile Leu Cys Val Ser Ser Asp Ala
1               5                   10                  15

Gln Pro Gln Thr Phe Glu Gly Val Lys Gly Ala Asp Pro Pro Thr Leu
            20                  25                  30

Pro Pro Gly Ser Phe Leu Pro Gly Pro Val Leu Trp Trp Gly Ser Leu
        35                  40                  45

Ala Arg Leu Gln Thr Glu Lys Ser Asp Glu Val Ser Arg Lys Gly Asn
    50                  55                  60

Trp Trp Val Thr Glu Met Gly Gly Gly Ala Gly Glu Arg Leu Phe Thr
65                  70                  75                  80

Ser Ser Cys Leu Val Gly Leu Val Pro Leu Gly Leu Arg Ile Ser Leu
                85                  90                  95

Val Thr Cys Pro Leu Gln Cys Gly Ile Met Trp Gln Leu Leu Leu Pro
            100                 105                 110

Thr Ala Leu Leu Leu Leu Val Ser Ala Gly Met Arg Thr Glu Asp Leu
        115                 120                 125

Pro Lys Ala Val Val Phe Leu Glu Pro Gln Trp Tyr Arg Val Leu Glu
    130                 135                 140

Lys Asp Ser Val Thr Leu Lys Cys Gln Gly Ala Tyr Ser Pro Glu Asp
145                 150                 155                 160

Asn Ser Thr Gln Trp Phe His Asn Glu Ser Leu Ile Ser Ser Gln Ala
                165                 170                 175

Ser Ser Tyr Phe Ile Asp Ala Ala Thr Val Asp Asp Ser Gly Glu Tyr
            180                 185                 190

Arg Cys Gln Thr Asn Leu Ser Thr Leu Ser Asp Pro Val Gln Leu Glu
        195                 200                 205

Val His Ile Gly Trp Leu Leu Leu Gln Ala Pro Arg Trp Val Phe Lys
    210                 215                 220

Glu Glu Asp Pro Ile His Leu Arg Cys His Ser Trp Lys Asn Thr Ala
225                 230                 235                 240

Leu His Lys Val Thr Tyr Leu Gln Asn Gly Lys Gly Arg Lys Tyr Phe
                245                 250                 255

His His Asn Ser Asp Phe Tyr Ile Pro Lys Ala Thr Leu Lys Asp Ser
            260                 265                 270

Gly Ser Tyr Phe Cys Arg Gly Leu Phe Gly Ser Lys Asn Val Ser Ser
        275                 280                 285

Glu Thr Val Asn Ile Thr Ile Thr Gln Gly Leu Ala Val Ser Thr Ile
    290                 295                 300

Ser Ser Phe Phe Pro Pro Gly Tyr Gln Val Ser Phe Cys Leu Val Met
305                 310                 315                 320

Val Leu Leu Phe Ala Val Asp Thr Gly Leu Tyr Phe Ser Val Lys Thr
                325                 330                 335

Asn Ile Arg Ser Ser Thr Arg Asp Trp Lys Asp His Lys Phe Lys Trp
            340                 345                 350

Arg Lys Asp Pro Gln Asp Lys
        355
```

<210> SEQ ID NO 10
<211> LENGTH: 233
<212> TYPE: PRT
<213> ORGANISM: Homo sapiens

<400> SEQUENCE: 10

```
Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Asn Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230
```

<210> SEQ ID NO 11
<211> LENGTH: 317
<212> TYPE: PRT
<213> ORGANISM: Homo sapiens

<400> SEQUENCE: 11

```
Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95
```

```
Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Val Leu Gln Thr
        115                 120                 125

Pro His Leu Glu Phe Gln Glu Gly Glu Thr Ile Met Leu Arg Cys His
    130                 135                 140

Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
                165                 170                 175

Ala Asn His Ser His Ser Gly Asp Tyr His Cys Thr Gly Asn Ile Gly
            180                 185                 190

Tyr Thr Leu Phe Ser Ser Lys Pro Val Thr Ile Thr Val Gln Val Pro
        195                 200                 205

Ser Met Gly Ser Ser Ser Pro Met Gly Ile Ile Val Ala Val Val Ile
    210                 215                 220

Ala Thr Ala Val Ala Ala Ile Val Ala Ala Val Val Ala Leu Ile Tyr
225                 230                 235                 240

Cys Arg Lys Lys Arg Ile Ser Ala Asn Ser Thr Asp Pro Val Lys Ala
                245                 250                 255

Ala Gln Phe Glu Pro Pro Gly Arg Gln Met Ile Ala Ile Arg Lys Arg
            260                 265                 270

Gln Leu Glu Glu Thr Asn Asn Asp Tyr Glu Thr Ala Asp Gly Gly Tyr
        275                 280                 285

Met Thr Leu Asn Pro Arg Ala Pro Thr Asp Asp Asp Lys Asn Ile Tyr
    290                 295                 300

Leu Thr Leu Pro Pro Asn Asp His Val Asn Ser Asn Asn
305                 310                 315


<210> SEQ ID NO 12
<211> LENGTH: 310
<212> TYPE: PRT
<213> ORGANISM: Homo sapiens

<400> SEQUENCE: 12

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
```

```
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Leu Pro
                245                 250                 255

Gly Tyr Pro Glu Cys Arg Glu Met Gly Glu Thr Leu Pro Glu Lys Pro
            260                 265                 270

Ala Asn Pro Thr Asn Pro Asp Glu Ala Asp Lys Val Gly Ala Glu Asn
        275                 280                 285

Thr Ile Thr Tyr Ser Leu Leu Met His Pro Asp Ala Leu Glu Glu Pro
    290                 295                 300

Asp Asp Gln Asn Arg Ile
305                 310


<210> SEQ ID NO 13
<211> LENGTH: 323
<212> TYPE: PRT
<213> ORGANISM: Homo sapiens

<400> SEQUENCE: 13

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Pro Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205
```

```
Pro Val Thr Ile Thr Val Gln Ala Pro Ser Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Ser
                245                 250                 255

Thr Asp Pro Val Lys Ala Ala Gln Phe Glu Pro Pro Gly Arg Gln Met
            260                 265                 270

Ile Ala Ile Arg Lys Arg Gln Pro Glu Glu Thr Asn Asn Asp Tyr Glu
        275                 280                 285

Thr Ala Asp Gly Gly Tyr Met Thr Leu Asn Pro Arg Ala Pro Thr Asp
    290                 295                 300

Asp Asp Lys Asn Ile Tyr Leu Thr Leu Pro Pro Asn Asp His Val Asn
305                 310                 315                 320

Ser Asn Asn


<210> SEQ ID NO 14
<211> LENGTH: 185
<212> TYPE: PRT
<213> ORGANISM: Homo sapiens

<400> SEQUENCE: 14

Met Ala Arg Gly Ala Ala Leu Ala Leu Leu Leu Phe Gly Leu Leu Gly
1               5                   10                  15

Val Leu Val Ala Ala Pro Asp Gly Gly Phe Asp Leu Ser Asp Ala Leu
            20                  25                  30

Pro Asp Asn Glu Asn Lys Lys Pro Thr Ala Ile Pro Lys Lys Pro Ser
        35                  40                  45

Ala Gly Asp Asp Phe Asp Leu Gly Asp Ala Val Val Asp Gly Glu Asn
    50                  55                  60

Asp Asp Pro Arg Pro Pro Asn Pro Pro Lys Pro Met Pro Asn Pro Asn
65                  70                  75                  80

Pro Asn His Pro Ser Ser Ser Gly Ser Phe Ser Asp Ala Asp Leu Ala
                85                  90                  95

Asp Gly Val Ser Gly Gly Glu Gly Lys Gly Gly Ser Asp Gly Gly Gly
            100                 105                 110

Ser His Arg Lys Glu Gly Glu Glu Ala Asp Ala Pro Gly Val Ile Pro
        115                 120                 125

Gly Ile Val Gly Ala Val Val Val Ala Val Ala Gly Ala Ile Ser Ser
    130                 135                 140

Phe Ile Ala Tyr Gln Lys Lys Lys Leu Cys Phe Lys Glu Asn Ala Glu
145                 150                 155                 160

Gln Gly Glu Val Asp Met Glu Ser His Arg Asn Ala Asn Ala Glu Pro
                165                 170                 175

Ala Val Gln Arg Thr Leu Leu Glu Lys
            180                 185


<210> SEQ ID NO 15
<211> LENGTH: 278
<212> TYPE: PRT
<213> ORGANISM: Homo sapiens

<400> SEQUENCE: 15

Met Glu Arg Leu Val Ile Arg Met Pro Phe Ser His Leu Ser Thr Tyr
1               5                   10                  15

Ser Leu Val Trp Val Met Ala Ala Val Val Leu Cys Thr Ala Gln Val
```

20 25 30

Gln Val Val Thr Gln Asp Glu Arg Glu Gln Leu Tyr Thr Pro Ala Ser
35 40 45

Leu Lys Cys Ser Leu Gln Asn Ala Gln Glu Ala Leu Ile Val Thr Trp
50 55 60

Gln Lys Lys Lys Ala Val Ser Pro Glu Asn Met Val Thr Phe Ser Glu
65 70 75 80

Asn His Gly Val Val Ile Gln Pro Ala Tyr Lys Asp Lys Ile Asn Ile
85 90 95

Thr Gln Leu Gly Leu Gln Asn Ser Thr Ile Thr Phe Trp Asn Ile Thr
100 105 110

Leu Glu Asp Glu Gly Cys Tyr Met Cys Leu Phe Asn Thr Phe Gly Phe
115 120 125

Gly Lys Ile Ser Gly Thr Ala Cys Leu Thr Val Tyr Val Gln Pro Ile
130 135 140

Val Ser Leu His Tyr Lys Phe Ser Glu Asp His Leu Asn Ile Thr Cys
145 150 155 160

Ser Ala Thr Ala Arg Pro Ala Pro Met Val Phe Trp Lys Val Pro Arg
165 170 175

Ser Gly Ile Glu Asn Ser Thr Val Thr Leu Ser His Pro Asn Gly Thr
180 185 190

Thr Ser Val Thr Ser Ile Leu His Ile Lys Asp Pro Lys Asn Gln Val
195 200 205

Gly Lys Glu Val Ile Cys Gln Val Leu His Leu Gly Thr Val Thr Asp
210 215 220

Phe Lys Gln Thr Val Asn Lys Gly Tyr Trp Phe Ser Val Pro Leu Leu
225 230 235 240

Leu Ser Ile Val Ser Leu Val Ile Leu Leu Val Leu Ile Ser Ile Leu
245 250 255

Leu Tyr Trp Lys Arg His Arg Asn Gln Asp Arg Gly Glu Leu Ser Gln
260 265 270

Gly Val Gln Lys Met Thr
275

<210> SEQ ID NO 16
<211> LENGTH: 413
<212> TYPE: PRT
<213> ORGANISM: Mus musculus

<400> SEQUENCE: 16

Met Thr Pro Ser Ile Ser Trp Cys Leu Leu Leu Leu Ala Gly Leu Cys
1 5 10 15

Cys Leu Val Pro Ser Phe Leu Ala Glu Asp Val Gln Glu Thr Asp Thr
20 25 30

Ser Gln Lys Asp Gln Ser Pro Ala Ser His Glu Ile Ala Thr Asn Leu
35 40 45

Gly Asp Phe Ala Ile Ser Leu Tyr Arg Glu Leu Val His Gln Ser Asn
50 55 60

Thr Ser Asn Ile Phe Phe Ser Pro Val Ser Ile Ala Thr Ala Phe Ala
65 70 75 80

Met Leu Ser Leu Gly Ser Lys Gly Asp Thr His Thr Gln Ile Leu Glu
85 90 95

Gly Leu Gln Phe Asn Leu Thr Gln Thr Ser Glu Ala Asp Ile His Asn
100 105 110

```
Ser Phe Gln His Leu Leu Gln Thr Leu Asn Arg Pro Asp Ser Glu Leu
        115                 120                 125

Gln Leu Ser Thr Gly Asn Gly Leu Phe Val Asn Asn Asp Leu Lys Leu
    130                 135                 140

Val Glu Lys Phe Leu Glu Glu Ala Lys Asn His Tyr Gln Ala Glu Val
145                 150                 155                 160

Phe Ser Val Asn Phe Ala Glu Ser Glu Glu Ala Lys Lys Val Ile Asn
                165                 170                 175

Asp Phe Val Glu Lys Gly Thr Gln Gly Lys Ile Val Glu Ala Val Lys
            180                 185                 190

Lys Leu Glu Gln Asp Thr Val Phe Val Leu Ala Asn Tyr Ile Leu Phe
        195                 200                 205

Lys Gly Lys Trp Lys Lys Pro Phe Asp Pro Glu Asn Thr Lys Gln Ala
    210                 215                 220

Glu Phe His Val Asp Glu Ser Thr Thr Val Lys Val Pro Met Met Thr
225                 230                 235                 240

Leu Ser Gly Met Leu Asp Val His His Cys Ser Thr Leu Ser Ser Trp
                245                 250                 255

Val Leu Leu Met Asp Tyr Ala Gly Asn Ala Thr Ala Val Phe Leu Leu
            260                 265                 270

Pro Asp Asp Gly Lys Met Gln His Leu Glu Gln Thr Leu Asn Lys Glu
        275                 280                 285

Leu Ile Ser Lys Phe Leu Leu Asn Arg Arg Arg Arg Leu Ala Gln Ile
    290                 295                 300

His Ile Pro Arg Leu Ser Ile Ser Gly Asn Tyr Asn Leu Glu Thr Leu
305                 310                 315                 320

Met Ser Pro Leu Gly Ile Thr Arg Ile Phe Asn Ser Gly Ala Asp Leu
                325                 330                 335

Ser Gly Ile Thr Glu Glu Asn Ala Pro Leu Lys Leu Ser Gln Ala Val
            340                 345                 350

His Lys Ala Val Leu Thr Ile Asp Glu Thr Gly Thr Glu Ala Ala Ala
        355                 360                 365

Ala Thr Val Leu Gln Gly Gly Phe Leu Ser Met Pro Pro Ile Leu His
    370                 375                 380

Phe Asn Arg Pro Phe Leu Phe Ile Ile Phe Glu Glu His Ser Gln Ser
385                 390                 395                 400

Pro Leu Phe Val Gly Lys Val Val Asp Pro Thr His Lys
                405                 410
```

<210> SEQ ID NO 17
<211> LENGTH: 418
<212> TYPE: PRT
<213> ORGANISM: Homo sapiens

<400> SEQUENCE: 17

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80
```

```
Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys
```

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
ggatgcagag gctcacagag 20

-continued

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

ctggcggttc acgttggact                                              20
```